US008716245B2

(12) United States Patent
Cerami et al.

(10) Patent No.: US 8,716,245 B2
(45) Date of Patent: May 6, 2014

(54) TISSUE PROTECTIVE PEPTIDES AND USES THEREOF

(75) Inventors: Anthony Cerami, New York, NY (US); Michael Brines, Woodbridge, CT (US); Thomas Coleman, Mount Kisco, NY (US)

(73) Assignee: Araim Pharmaceuticals, Inc., Tarrytown, NY (US)

(*) Notice: Subject to any disclaimer, the term of this patent is extended or adjusted under 35 U.S.C. 154(b) by 30 days.

(21) Appl. No.: 13/278,131

(22) Filed: Oct. 20, 2011

(65) Prior Publication Data
US 2012/0142595 A1    Jun. 7, 2012

Related U.S. Application Data

(63) Continuation of application No. 11/997,898, filed as application No. PCT/US2006/031061 on Aug. 7, 2006, now Pat. No. 8,071,554.

(60) Provisional application No. 60/705,741, filed on Aug. 5, 2005, provisional application No. 60/706,276, filed on Aug. 8, 2005, provisional application No. 60/831,737, filed on Jul. 18, 2006.

(51) Int. Cl.
C07K 7/08      (2006.01)
A61K 38/10    (2006.01)
A61K 48/00    (2006.01)

(52) U.S. Cl.
USPC .......... 514/21.5; 530/327; 530/333; 514/44 R

(58) Field of Classification Search
None
See application file for complete search history.

(56) References Cited

U.S. PATENT DOCUMENTS 5,700,909 A    12/1997  O'Brien
8,071,554 B2 *  12/2011  Cerami et al. ............... 514/21.6

FOREIGN PATENT DOCUMENTS

| EP | 0 116 446 | | 8/1984 |
|---|---|---|---|
| EP | 0 410 246 | | 1/1991 |
| EP | 1 736 481 | | 12/2006 |
| WO | WO 95/21919 | * | 8/1995 |
| WO | WO/00/61164 A1 | | 10/2000 |
| WO | WO/02/053580 A2 | | 7/2002 |
| WO | WO/2004/003176 A2 | | 1/2004 |
| WO | WO/2004/004656 A2 | | 1/2004 |
| WO | WO/2004/096148 A2 | | 11/2004 |
| WO | WO/2005/025606 A1 | | 3/2005 |
| WO | WO/2005/032467 A2 | | 4/2005 |
| WO | WO 2006/091727 A2 | | 8/2006 |
| WO | WO 2006/119767 | | 11/2006 |
| WO | WO 2006/127910 A2 | | 11/2006 |
| WO | WO 2007/010552 A2 | | 1/2007 |
| WO | WO 2007/019545 A2 | | 2/2007 |

OTHER PUBLICATIONS

Congote, BBRC., 2004, 324, 673-678.*
Skelton, J. Mol. Biol., 2002, 316, 1111-1125.*
European Search Report dated Jun. 22, 2009, for European Application No. 06801051.1, filed Aug. 7, 2006.
ISA/US International Search Report dated Jul. 28, 2008, for International Application No. PCT/US2006/031061, filed Aug. 7, 2006.
Noli, N., 1997, "Design, Synthesis and Conformational Analysis of hGM-CSF(13-31)-Gly-Pro-Gly-(103-116)," Journal of Peptide Science, vol. 3:323-335.
Wolfert, M.A., 1998, "Chloroquine and Amphipathic Peptide Helices Show Synergistic Transfection In Vitro," Gene Therapy, vol. 5:409-411.
Barlow, "Peptide Drug Design," *Smith and William's Introduction to the Principles of Drug Design and Action*, 4th Edition, Taylor & Francis Group, USA, 327-354 (2006).
Beffy et al., "An immunodominant epitope in a functional domain near the N-terminus of human granulocyte-macrophage colony-stimulating factor identified by cross-reaction of synthetic peptides with neutralizing anti-protein and anti-peptide antibodies," *Hybridoma*, 13(6):457-468 (1994).
Brines et al., "Erythropoietin mediates tissue protection through an erythropoietin and common β-subunit heteroreceptor," *Proc. Natl. Acad. Sci. U.S.A.*, 101(41):14907-14912 (2004).
Brines et al., "Nonerythropoietin, tissue-protective peptides derived from the tertiary structure of erythropoietin," *Proc. Natl. Acad. Sci, USA*, 105(31): 10925-10930 (2008).
Elliott et al., "Fine-structure epitope mapping of antierythropoietin monoclonal antibodies reveals a model of recombinant human erythropoietin structure," *Blood*, 87(7):2702-2713 (1996).
Elliott et al., "Mapping of the acrtive site of recombinant human erythropoietin," *Blood*, 89(2):493-502 (1997).
Elliott et al., "Structural requirements for additional N-linked carboydrate on recombinant human erthropeoietin," *J. Biol. Chem.*, 279(16):16854-16862 (2004).
Ghezzi et al., "Erythropoietin as an antiapoptotic, tissue protective cytokine," *Cell Death & Differentiation*,11(S1):S37-S44 (2004).
IPEA/EP, PCT International Preliminary Report on Patentability dated May 18, 2010 for International Application No. PCT/US2009/00424.
ISA/EP PCT International Search Report and Written Opinion dated Oct. 27, 2009, for International Application No. PCT/US2009/00424.
Kaiser et al., "Recombinant human erythropoietin prevents the death of mice during cerebral malaria," *J. Infectious Diseases*, 193(7):987-995 (2006).
Konstantinopoulos et al., "Selective modulation of the erythropoietic and tissue-protective effects of erythropoietin: Time to reach the full therapeutic potential of erythropoietin," *BBA Reviews on Cancer*, 1776(1):1-9 (2007).

(Continued)

*Primary Examiner* — Satyanarayana R Gudibande
(74) *Attorney, Agent, or Firm* — Jones Day

(57) ABSTRACT

Provided herein are tissue protective peptides derived from or sharing consensus sequences with portions of cytokine receptor ligands, including Erythropoietin (EPO), that are generally located on or within the region of the cytokine receptor ligand that faces away from a receptor complex while the ligand is bound to the receptor. Also provide herein are fragments, chimeras, as well as peptides designed to mimic the spatial localization of key amino acid residues within the tissue protective receptor ligands, e.g., EPO; methods for treating or preventing a disease or disorder using tissue protective peptides; and methods for enhancing excitable tissue function using tissue protective peptides.

14 Claims, 13 Drawing Sheets

(56) References Cited

OTHER PUBLICATIONS

Leist et al., "Derivatives of erythropoietin that are tissue protective but not erythropoietic," *Science*, 305:239-243 (2004).

Park et al., "Identification of functionally important residues of human thrombopoietin," *J. Biol. Chem.*, 273(1):256-261 (1998).

Peggion et al., "Design, synthesis, and conformational strudies of the hGM-CSF derived peptide (13-27)-Gly-(75-87)," *Biopolymers*, 50(5):545-554 (1999).

Sun, et al., "Redox Regulation of Cell Signaling by Selenocysteine in Mammalian Thioredoxin Reductases," *J. Biol. Chem.*, 274(35):24522-24530 (1999).

Tahara et al., "Neutralization of biological activity and inhibition of receptor binding by antibodies against human thrombopoietin," *Stem Cells* 16(1):54-60 (1998).

Takashi et al., "Protein characteristics of thrombopoietin," *Stem Cells*, 14(S1):139-147 (1996).

Von Feldt et al., "Development of GM-CSF antagonist peptides," *Peptide Res.*, 8(1):20-27, 30-32 (1995).

Website: http://www.merckmanuals.com/professional/neurologic_disorders/peripheral_nervous_system_and_motor_unit_disorders/overview_of_peripheral_nervous_system_disorders.html, 8 pages, retrieved on Mar. 7, 2013.

Website: http://www.nlm.nih.gov/medlineplus/peripheralnervesdisorders.html, 4 pages, retrieved on Mar. 7, 2013.

Wen et al., "Erythropoietin structure-function relationships," *J. Biol. Chem.*, 269(36):22839-22846 (1994).

\* cited by examiner

SEQUENCE LISTING

<160> NUMBER OF SEQ ID NOS: 58

<210> SEQ ID NO 1
<211> LENGTH: 165
<212> TYPE: PRT
<213> ORGANISM: Artificial Sequence
<220> FEATURE:
<223> OTHER INFORMATION: Erythropoietin peptide

<400> SEQUENCE: 1

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 6
<212> TYPE: PRT
<213> ORGANISM: Artificial Sequence
<220> FEATURE:
<223> OTHER INFORMATION: EPO amino Acids 44-49 associated with a high
      affinity receptor binding site 1

<400> SEQUENCE: 2

Thr Lys Val Asn Phe Tyr
 1               5

<210> SEQ ID NO 3
<211> LENGTH: 6
<212> TYPE: PRT
<213> ORGANISM: Artificial Sequence
<220> FEATURE:
<223> OTHER INFORMATION: EPO amino acids 146-151 associated with a high
      affinity receptor binding site 1

<400> SEQUENCE: 3

Ser Asn Phe Leu Arg Gly
 1               5

<210> SEQ ID NO 4
<211> LENGTH: 5
<212> TYPE: PRT
<213> ORGANISM: Artificial Sequence

```
<220> FEATURE:
<223> OTHER INFORMATION: EPO amino acids 11-15  interacting with a low
      affinity receptor binding Site 2

<400> SEQUENCE: 4

Val Leu Glu Arg Tyr
 1               5

<210> SEQ ID NO 5
<211> LENGTH: 5
<212> TYPE: PRT
<213> ORGANISM: Artificial Sequence
<220> FEATURE:
<223> OTHER INFORMATION: EPO amino acids 100-104 interacting with a low
      affinity receptor binding site 2

<400> SEQUENCE: 5

Ser Gly Leu Arg Ser
 1               5

<210> SEQ ID NO 6
<211> LENGTH: 4
<212> TYPE: PRT
<213> ORGANISM: Artificial Sequence
<220> FEATURE:
<223> OTHER INFORMATION: Isolated polypeptides comprising amino acid
      structural motif A
<220> FEATURE:
<221> NAME/KEY: VARIANT
<222> LOCATION: 1,4
<223> OTHER INFORMATION: Xaa = any hydrophobic amino acid (same or
      different)
<220> FEATURE:
<221> NAME/KEY: VARIANT
<222> LOCATION: 2,3
<223> OTHER INFORMATION: Xaa = any negatively charged amino acid (same
      or different)

<400> SEQUENCE: 6

Xaa Xaa Xaa Xaa
 1

<210> SEQ ID NO 7
<211> LENGTH: 5
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1,5
<223> OTHER INFORMATION: Xaa = Any hydrophobic amino acid (same or
      different)
<220> FEATURE:
<221> NAME/KEY: VARIANT
<222> LOCATION: 2, 4
<223> OTHER INFORMATION: Xaa = Any negatively charged amino acid (same
      or different)
<220> FEATURE:
<221> NAME/KEY: VARIANT
<222> LOCATION: 3
<223> OTHER INFORMATION: Xaa = Any amino acid

<400> SEQUENCE: 7

Xaa Xaa Xaa Xaa Xaa
 1               5

<210> SEQ ID NO 8
<211> LENGTH: 6
<212> TYPE: PRT
<213> ORGANISM: Artificial Sequence
```

```
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1, 6
<223> OTHER INFORMATION: Xaa = Any hydrophobic amino acid (same or
      different)
<220> FEATURE:
<221> NAME/KEY: VARIANT
<222> LOCATION: 2,5
<223> OTHER INFORMATION: Xaa = Any negatively charged animo acid (same
      or different)
<220> FEATURE:
<221> NAME/KEY: VARIANT
<222> LOCATION: 3,4
<223> OTHER INFORMATION: Xaa = Any amino acid (same or different)

<400> SEQUENCE: 8

Xaa Xaa Xaa Xaa Xaa Xaa
 1               5

<210> SEQ ID NO 9
<211> LENGTH: 7
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1, 7
<223> OTHER INFORMATION: Xaa = Any hydrophobic amino acid (same or
      different)
<220> FEATURE:
<221> NAME/KEY: VARIANT
<222> LOCATION: 2,6
<223> OTHER INFORMATION: Xaa = Any negatively charged amino acid (same
      or different)
<220> FEATURE:
<221> NAME/KEY: VARIANT
<222> LOCATION: 3,4,5
<223> OTHER INFORMATION: Xaa = Any amino acid (same or different)

<400> SEQUENCE: 9

Xaa Xaa Xaa Xaa Xaa Xaa Xaa
 1               5

<210> SEQ ID NO 10
<211> LENGTH: 8
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1,8
<223> OTHER INFORMATION: Xaa = Any hydrophobic amino acid (same or
      different)
<220> FEATURE:
<221> NAME/KEY: VARIANT
<222> LOCATION: 2, 7
<223> OTHER INFORMATION: Xaa = Any negatively charged amino acid (same
      or different)
<220> FEATURE:
<221> NAME/KEY: VARIANT
<222> LOCATION: 3,4,5,6
<223> OTHER INFORMATION: Xaa = Any amino acid (same or different)

<400> SEQUENCE: 10

Xaa Xaa Xaa Xaa Xaa Xaa Xaa Xaa
 1               5
```

```
<210> SEQ ID NO 11
<211> LENGTH: 9
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1, 9
<223> OTHER INFORMATION: Xaa = Any hydrophobic amino acid (same or
      different)
<220> FEATURE:
<221> NAME/KEY: VARIANT
<222> LOCATION: 2, 8
<223> OTHER INFORMATION: Xaa = Any negatively charged amino acid (same
      or different)
<220> FEATURE:
<221> NAME/KEY: VARIANT
<222> LOCATION: 3,4,5,6,7
<223> OTHER INFORMATION: Xaa = Any amino acid (same or different)

<400> SEQUENCE: 11

Xaa Xaa Xaa Xaa Xaa Xaa Xaa Xaa Xaa
 1               5

<210> SEQ ID NO 12
<211> LENGTH: 4
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any hydrophobic amino acid
<220> FEATURE:
<221> NAME/KEY: VARIANT
<222> LOCATION: 2, 3
<223> OTHER INFORMATION: Xaa = Any negatively charged amino acid (same
      or different)
<220> FEATURE:
<221> NAME/KEY: VARIANT
<222> LOCATION: 4
<223> OTHER INFORMATION: Xaa = Any polar amino acid

<400> SEQUENCE: 12

Xaa Xaa Xaa Xaa
 1

<210> SEQ ID NO 13
<211> LENGTH: 5
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any hydrophobic amino acid
<220> FEATURE:
<221> NAME/KEY: VARIANT
<222> LOCATION: 2,4
<223> OTHER INFORMATION: Xaa = Any negatively charged amino acid
<220> FEATURE:
<221> NAME/KEY: VARIANT
<222> LOCATION: 3
<223> OTHER INFORMATION: Xaa = Any amino acid
<220> FEATURE:
<221> NAME/KEY: VARIANT
<222> LOCATION: 5
<223> OTHER INFORMATION: Xaa = Any polar amino acid

<400> SEQUENCE: 13
```

-continued

```
Xaa Xaa Xaa Xaa Xaa
 1               5

<210> SEQ ID NO 14
<211> LENGTH: 6
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any hydrophobic amino acid
<220> FEATURE:
<221> NAME/KEY: VARIANT
<222> LOCATION: 2,5
<223> OTHER INFORMATION: Xaa = Any negatively charged amino acid (same
      or different)
<220> FEATURE:
<221> NAME/KEY: VARIANT
<222> LOCATION: 3,4
<223> OTHER INFORMATION: Xaa = Any amino acid (same or different)
<220> FEATURE:
<221> NAME/KEY: VARIANT
<222> LOCATION: 6
<223> OTHER INFORMATION: Xaa = Any polar amino acid

<400> SEQUENCE: 14

Xaa Xaa Xaa Xaa Xaa Xaa
 1               5

<210> SEQ ID NO 15
<211> LENGTH: 7
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any hydrophobic amino acid
<220> FEATURE:
<221> NAME/KEY: VARIANT
<222> LOCATION: 2, 6
<223> OTHER INFORMATION: Xaa = Any negatively charged amino acid (same
      or different)
<220> FEATURE:
<221> NAME/KEY: VARIANT
<222> LOCATION: 3,4,5
<223> OTHER INFORMATION: Xaa = Any amino acid (same or different)
<220> FEATURE:
<221> NAME/KEY: VARIANT
<222> LOCATION: 7
<223> OTHER INFORMATION: Xaa = Any polar amino acid

<400> SEQUENCE: 15

Xaa Xaa Xaa Xaa Xaa Xaa Xaa
 1               5

<210> SEQ ID NO 16
<211> LENGTH: 8
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any hydrophobic amino acid
<220> FEATURE:
<221> NAME/KEY: VARIANT
```

```
<222> LOCATION: 2, 7
<223> OTHER INFORMATION: Xaa = Any negatively charged amino acid (same
      or different)
<220> FEATURE:
<221> NAME/KEY: VARIANT
<222> LOCATION: 3,4,5,6
<223> OTHER INFORMATION: Xaa = Any amino acid (same or different)
<220> FEATURE:
<221> NAME/KEY: VARIANT
<222> LOCATION: 8
<223> OTHER INFORMATION: Xaa = Any polar amino acid

<400> SEQUENCE: 16

Xaa Xaa Xaa Xaa Xaa Xaa Xaa Xaa
 1               5

<210> SEQ ID NO 17
<211> LENGTH: 9
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any hydrophobic amino acid
<220> FEATURE:
<221> NAME/KEY: VARIANT
<222> LOCATION: 2, 8
<223> OTHER INFORMATION: Xaa = Any negatively charged amino acid (same
      or different)
<220> FEATURE:
<221> NAME/KEY: VARIANT
<222> LOCATION: 3,4,5,6,7
<223> OTHER INFORMATION: Xaa = Any amino acid (same or different)
<220> FEATURE:
<221> NAME/KEY: VARIANT
<222> LOCATION: 9
<223> OTHER INFORMATION: Xaa = Any polar amino acid

<400> SEQUENCE: 17

Xaa Xaa Xaa Xaa Xaa Xaa Xaa Xaa Xaa
 1               5

<210> SEQ ID NO 18
<211> LENGTH: 4
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any polar amino acid
<220> FEATURE:
<221> NAME/KEY: VARIANT
<222> LOCATION: 2,3
<223> OTHER INFORMATION: Xaa = Any negatively charged amino acid (same
      or different)
<220> FEATURE:
<221> NAME/KEY: VARIANT
<222> LOCATION: 4
<223> OTHER INFORMATION: Xaa = Any hydrophobic amino acid

<400> SEQUENCE: 18

Xaa Xaa Xaa Xaa
 1

<210> SEQ ID NO 19
<211> LENGTH: 5
<212> TYPE: PRT
<213> ORGANISM: Artificial Sequence
```

```
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any polar amino acid
<220> FEATURE:
<221> NAME/KEY: VARIANT
<222> LOCATION: 2,4
<223> OTHER INFORMATION: Xaa = Any negatively charged amino acid (same
      or different)
<220> FEATURE:
<221> NAME/KEY: VARIANT
<222> LOCATION: 3
<223> OTHER INFORMATION: Xaa = Any amino acid
<220> FEATURE:
<221> NAME/KEY: VARIANT
<222> LOCATION: 5
<223> OTHER INFORMATION: Xaa = Any hydrophobic amino acid

<400> SEQUENCE: 19

Xaa Xaa Xaa Xaa Xaa
 1               5

<210> SEQ ID NO 20
<211> LENGTH: 6
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any polar amino acid
<220> FEATURE:
<221> NAME/KEY: VARIANT
<222> LOCATION: 2, 5
<223> OTHER INFORMATION: Xaa = Any negatively charged amino acid (same
      or different)
<220> FEATURE:
<221> NAME/KEY: VARIANT
<222> LOCATION: 3,4
<223> OTHER INFORMATION: Xaa = Any amino acid (same or different)
<220> FEATURE:
<221> NAME/KEY: VARIANT
<222> LOCATION: 6
<223> OTHER INFORMATION: Xaa = Any hydrophobic amino acid

<400> SEQUENCE: 20

Xaa Xaa Xaa Xaa Xaa Xaa
 1               5

<210> SEQ ID NO 21
<211> LENGTH: 7
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any polar amino acid
<220> FEATURE:
<221> NAME/KEY: VARIANT
<222> LOCATION: 2,6
<223> OTHER INFORMATION: Xaa = Any negatively charged amino acid (same
      or different)
<220> FEATURE:
<221> NAME/KEY: VARIANT
<222> LOCATION: 3,4,5
<223> OTHER INFORMATION: Xaa = Any amino acid (same or different)
<220> FEATURE:
<221> NAME/KEY: VARIANT
```

```
<222> LOCATION: 7
<223> OTHER INFORMATION: Xaa = Any hydrophobic amino acid

<400> SEQUENCE: 21

Xaa Xaa Xaa Xaa Xaa Xaa Xaa
 1               5

<210> SEQ ID NO 22
<211> LENGTH: 8
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any polar amino acid
<220> FEATURE:
<221> NAME/KEY: VARIANT
<222> LOCATION: 2,7
<223> OTHER INFORMATION: Xaa = Any negatively charged amino acid (same
      or different)
<220> FEATURE:
<221> NAME/KEY: VARIANT
<222> LOCATION: 3,4,5,6
<223> OTHER INFORMATION: Xaa = Any amino acid (same or different)
<220> FEATURE:
<221> NAME/KEY: VARIANT
<222> LOCATION: 8
<223> OTHER INFORMATION: Xaa = Any hydrophobic amino acid

<400> SEQUENCE: 22

Xaa Xaa Xaa Xaa Xaa Xaa Xaa Xaa
 1               5

<210> SEQ ID NO 23
<211> LENGTH: 9
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1
<223> OTHER INFORMATION: Xaa = Any polar amino acid
<220> FEATURE:
<221> NAME/KEY: VARIANT
<222> LOCATION: 2,8
<223> OTHER INFORMATION: Xaa = Any negatively charged amino acid (same
      or different)
<220> FEATURE:
<221> NAME/KEY: VARIANT
<222> LOCATION: 3,4,5,6,7
<223> OTHER INFORMATION: Xaa = Any amino acid (same or different)
<220> FEATURE:
<221> NAME/KEY: VARIANT
<222> LOCATION: 9
<223> OTHER INFORMATION: Xaa = Any hydrophobic amino acid

<400> SEQUENCE: 23

Xaa Xaa Xaa Xaa Xaa Xaa Xaa Xaa Xaa
 1               5

<210> SEQ ID NO 24
<211> LENGTH: 4
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
```

```
<222> LOCATION: 1,4
<223> OTHER INFORMATION: Xaa = Any hydrophobic amino acid (same or
      different)
<220> FEATURE:
<221> NAME/KEY: VARIANT
<222> LOCATION: 2
<223> OTHER INFORMATION: Xaa = Any negatively charged amino acid
<220> FEATURE:
<221> NAME/KEY: VARIANT
<222> LOCATION: 3
<223> OTHER INFORMATION: Xaa = Any positively charged amino acid

<400> SEQUENCE: 24

Xaa Xaa Xaa Xaa
 1

<210> SEQ ID NO 25
<211> LENGTH: 5
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1,5
<223> OTHER INFORMATION: Xaa = Any hydrophobic amino acid
<220> FEATURE:
<221> NAME/KEY: VARIANT
<222> LOCATION: 2
<223> OTHER INFORMATION: Xaa = Any negatively charged amino acid
<220> FEATURE:
<221> NAME/KEY: VARIANT
<222> LOCATION: 3
<223> OTHER INFORMATION: Xaa = Any polar amino acid
<220> FEATURE:
<221> NAME/KEY: VARIANT
<222> LOCATION: 4
<223> OTHER INFORMATION: Xaa = Any positively charged amino acid

<400> SEQUENCE: 25

Xaa Xaa Xaa Xaa Xaa
 1               5

<210> SEQ ID NO 26
<211> LENGTH: 4
<212> TYPE: PRT
<213> ORGANISM: Artificial Sequence
<220> FEATURE:
<223> OTHER INFORMATION: Variant of isolated EPO polypeptides comprising
      amino acid structural motif A
<220> FEATURE:
<221> NAME/KEY: VARIANT
<222> LOCATION: 1,4
<223> OTHER INFORMATION: Xaa = Any hydrophobic amino acid
<220> FEATURE:
<221> NAME/KEY: VARIANT
<222> LOCATION: 2
<223> OTHER INFORMATION: Xaa = Any positively charged amino acid
<220> FEATURE:
<221> NAME/KEY: VARIANT
<222> LOCATION: 3
<223> OTHER INFORMATION: Xaa = Any negatively charged amino acid

<400> SEQUENCE: 26

Xaa Xaa Xaa Xaa
 1

<210> SEQ ID NO 27
<211> LENGTH: 5
<212> TYPE: PRT
<213> ORGANISM: Artificial Sequence
<220> FEATURE:
<223> OTHER INFORMATION: Variant of isolated EPO polypeptides comprising
```

```
                amino acid structural motif A
<220> FEATURE:
<221> NAME/KEY: VARIANT
<222> LOCATION: 1,5
<223> OTHER INFORMATION: Xaa = Any hydrophobic amino acid
<220> FEATURE:
<221> NAME/KEY: VARIANT
<222> LOCATION: 2
<223> OTHER INFORMATION: Xaa = Any positively charged amino acid
<220> FEATURE:
<221> NAME/KEY: VARIANT
<222> LOCATION: 3
<223> OTHER INFORMATION: Xaa = Any polar amino acid
<220> FEATURE:
<221> NAME/KEY: VARIANT
<222> LOCATION: 4
<223> OTHER INFORMATION: Xaa = Any negatively charged amino acid

<400> SEQUENCE: 27

Xaa Xaa Xaa Xaa Xaa
1               5

<210> SEQ ID NO 28
<211> LENGTH: 11
<212> TYPE: PRT
<213> ORGANISM: Artificial Sequence
<220> FEATURE:
<223> OTHER INFORMATION: Amphipathic helix from pancreatic polypeptide

<400> SEQUENCE: 28

Leu Arg Arg Tyr Ile Asn Met Leu Thr Arg Pro
1               5                   10

<210> SEQ ID NO 29
<211> LENGTH: 20
<212> TYPE: PRT
<213> ORGANISM: Artificial Sequence
<220> FEATURE:
<223> OTHER INFORMATION: Peptide C - loop AB and N-terminal portion of
      helix B corresponding to EPO amino acids 38-57

<400> SEQUENCE: 29

Asn Ile Thr Val Pro Asp Thr Lys Val Asn Phe Tyr Ala Trp Lys Arg
1               5                   10                  15

Met Glu Val Gly
            20

<210> SEQ ID NO 30
<211> LENGTH: 25
<212> TYPE: PRT
<213> ORGANISM: Artificial Sequence
<220> FEATURE:
<223> OTHER INFORMATION: Peptide D - the C-terminal portion of helix B
      corresponding to EPO amino acids 58-82

<400> SEQUENCE: 30

Gln Gln Ala Val Glu Val Trp Gln Gly Leu Ala Leu Leu Ser Glu Ala
1               5                   10                  15

Val Leu Arg Gly Gln Ala Leu Leu Val
            20                  25

<210> SEQ ID NO 31
<211> LENGTH: 20
<212> TYPE: PRT
<213> ORGANISM: Artificial Sequence
<220> FEATURE:
<223> OTHER INFORMATION: Peptide E - a portion of the A-B loop
      consisting of a small cysteine loop and a Beta-pleated sheet
      corresponding to EPO amino acids 28-47
```

-continued

```
<400> SEQUENCE: 31

Gly Cys Ala Glu His Cys Ser Leu Asn Glu Asn Ile Thr Val Pro Asp
1               5                   10                  15

Thr Lys Val Asn
            20

<210> SEQ ID NO 32
<211> LENGTH: 23
<212> TYPE: PRT
<213> ORGANISM: Artificial Sequence
<220> FEATURE:
<223> OTHER INFORMATION: Peptide A - consists of the N-terminal portion
      of Helix A corresponding to EPO amino acids 1-23

<400> SEQUENCE: 32

Ala Pro Pro Arg Leu Ile Cys Asp Ser Arg Val Leu Glu Arg Tyr Leu
1               5                   10                  15

Leu Glu Ala Lys Glu Ala Glu
            20

<210> SEQ ID NO 33
<211> LENGTH: 16
<212> TYPE: PRT
<213> ORGANISM: Artificial Sequence
<220> FEATURE:
<223> OTHER INFORMATION: Peptide F - consists of EPO amino acids 14-19

<400> SEQUENCE: 33

Arg Tyr Leu Leu Glu Ala Lys Glu Ala Glu Asn Ile Thr Thr Gly Cys
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: Peptide B - consists of EPO amino acids 24-37

<400> SEQUENCE: 34

Asn Ile Thr Thr Gly Cys Ala Glu His Cys Ser Leu Asn Glu
1               5                   10

<210> SEQ ID NO 35
<211> LENGTH: 14
<212> TYPE: PRT
<213> ORGANISM: Artificial Sequence
<220> FEATURE:
<223> OTHER INFORMATION: GM-CSF helix A fragment

<400> SEQUENCE: 35

Trp Glu His Val Asn Ala Ile Gln Glu Ala Arg Arg Leu Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: TPO helix A fragment

<400> SEQUENCE: 36

Leu Ser Lys Leu Leu Arg Asp Ser His Val Leu His
1               5                   10

<210> SEQ ID NO 37
<211> LENGTH: 16
```

```
<212> TYPE: PRT
<213> ORGANISM: Artificial Sequence
<220> FEATURE:
<223> OTHER INFORMATION: CNTF helix A fragment

<400> SEQUENCE: 37

Lys Ile Arg Ser Asp Leu Thr Ala Leu Thr Glu Ser Tyr Val Lys His
 1               5                  10                  15

<210> SEQ ID NO 38
<211> LENGTH: 17
<212> TYPE: PRT
<213> ORGANISM: Artificial Sequence
<220> FEATURE:
<223> OTHER INFORMATION: LIF helix B fragment

<400> SEQUENCE: 38

Gly Thr Glu Lys Ala Lys Leu Val Glu Leu Tyr Arg Ile Val Val Tyr
 1               5                  10                  15

Leu

<210> SEQ ID NO 39
<211> LENGTH: 18
<212> TYPE: PRT
<213> ORGANISM: Artificial Sequence
<220> FEATURE:
<223> OTHER INFORMATION: Interleukin 3 (IL-3) helix A fragment

<400> SEQUENCE: 39

Ser Ile Met Ile Asp Glu Ile Ile His His Leu Lys Arg Pro Pro Asn
 1               5                  10                  15

Pro Leu

<210> SEQ ID NO 40
<211> LENGTH: 11
<212> TYPE: PRT
<213> ORGANISM: Artificial Sequence
<220> FEATURE:
<223> OTHER INFORMATION: Peptide G - All exterior-presenting amino acids
      of helix B of EPO

<400> SEQUENCE: 40

Gln Glu Gln Leu Glu Arg Ala Leu Asn Ser Ser
 1               5                  10

<210> SEQ ID NO 41
<211> LENGTH: 23
<212> TYPE: PRT
<213> ORGANISM: Artificial Sequence
<220> FEATURE:
<223> OTHER INFORMATION: Peptide J - A chimera peptide of Peptide G
      linked to pancreatic polypeptide helix

<400> SEQUENCE: 41

Gln Glu Gln Leu Glu Arg Ala Leu Asn Ser Ser Leu Arg Arg Tyr Ile
 1               5                  10                  15

Asn Met Leu Thr Arg Thr Arg
            20

<210> SEQ ID NO 42
<211> LENGTH: 7
<212> TYPE: PRT
<213> ORGANISM: Artificial Sequence
<220> FEATURE:
<223> OTHER INFORMATION: Beta-pleated sheet found within AB loop of EPO

<400> SEQUENCE: 42
```

```
Cys Ser Leu Asn Glu Asn Ile
 1               5

<210> SEQ ID NO 43
<211> LENGTH: 18
<212> TYPE: PRT
<213> ORGANISM: Artificial Sequence
<220> FEATURE:
<223> OTHER INFORMATION: Peptide I - A chimera peptide linking the helix
      B exterior-presenting amino acids to the beta
      pleated sheet found within the AB loop of the EPO

<400> SEQUENCE: 43

Cys Ser Leu Asn Glu Asn Ile Gln Glu Gln Leu Glu Arg Ala Leu Asn
 1               5                   10                  15

Ser Ser

<210> SEQ ID NO 44
<211> LENGTH: 5
<212> TYPE: PRT
<213> ORGANISM: Artificial Sequence
<220> FEATURE:
<223> OTHER INFORMATION: Terminal portion of helix C corresponding to
      amino acids 111,112,113,116, and 118 of EPO

<400> SEQUENCE: 44

Ala Leu Gly Lys Ala
 1               5

<210> SEQ ID NO 45
<211> LENGTH: 22
<212> TYPE: PRT
<213> ORGANISM: Artificial Sequence
<220> FEATURE:
<223> OTHER INFORMATION: Loop CD-partial corresponding to amino acids
      112-133 of EPO

<400> SEQUENCE: 45

Leu Gly Ala Gln Lys Glu Ala Ile Ser Pro Pro Asp Ala Ala Ser Ala
 1               5                   10                  15

Ala Pro Leu Arg Thr Ile
            20

<210> SEQ ID NO 46
<211> LENGTH: 4
<212> TYPE: PRT
<213> ORGANISM: Artificial Sequence
<220> FEATURE:
<223> OTHER INFORMATION: amino acid fragment of Peptide F

<400> SEQUENCE: 46

Glu Ala Lys Glu
 1

<210> SEQ ID NO 47
<211> LENGTH: 6
<212> TYPE: PRT
<213> ORGANISM: Artificial Sequence
<220> FEATURE:
<223> OTHER INFORMATION: Peptide H - consists of EPO amino acids 61, 72,
      75, 76, 77

<400> SEQUENCE: 47

Ser Glu Leu Arg Gly Gln
 1               5
```

```
<210> SEQ ID NO 48
<211> LENGTH: 12
<212> TYPE: PRT
<213> ORGANISM: Artificial Sequence
<220> FEATURE:
<223> OTHER INFORMATION: Calcitonin

<400> SEQUENCE: 48

Ala Leu Ser Ile Leu Val Leu Leu Gln Ala Gly Ser
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Corticotrophin Releasing Hormone

<400> SEQUENCE: 49

Val Ala Leu Leu Pro Cys Pro Pro Cys Arg Ala
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Beta Endorphin

<400> SEQUENCE: 50

Asn Ala Ile Ile Lys Asn Ala Tyr Lys Lys Gly
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Glucagon

<400> SEQUENCE: 51

Gly Ser Trp Gln Arg Ser Leu Gln Asp Thr Glu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Secretin

<400> SEQUENCE: 52

Gly Gly Ser Ala Ala Arg Pro Ala Pro Pro
1               5                   10

<210> SEQ ID NO 53
<211> LENGTH: 11
<212> TYPE: PRT
<213> ORGANISM: Artificial Sequence
<220> FEATURE:
<223> OTHER INFORMATION: VIP

<400> SEQUENCE: 53

Asn Ala Leu Ala Glu Asn Asp Thr Pro Tyr Tyr
1               5                   10

<210> SEQ ID NO 54
<211> LENGTH: 11
```

```
<212> TYPE: PRT
<213> ORGANISM: Artificial Sequence
<220> FEATURE:
<223> OTHER INFORMATION: NP-Y

<400> SEQUENCE: 54

Gly Ala Leu Ala Glu Ala Tyr Pro Ser Lys Pro
1               5                   10

<210> SEQ ID NO 55
<211> LENGTH: 11
<212> TYPE: PRT
<213> ORGANISM: Artificial Sequence
<220> FEATURE:
<223> OTHER INFORMATION: GNRH

<400> SEQUENCE: 55

Gly Cys Ser Ser Gln His Trp Ser Tyr Gly Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Parathyroid Hormone

<400> SEQUENCE: 56

Val Met Ile Val Met Leu Ala Ile Cys Phe Leu
1               5                   10

<210> SEQ ID NO 57
<211> LENGTH: 11
<212> TYPE: PRT
<213> ORGANISM: Artificial Sequence
<220> FEATURE:
<223> OTHER INFORMATION: CGRP

<400> SEQUENCE: 57

Leu Ala Leu Ser Ile Leu Val Leu Tyr Gln Ala
1               5                   10

<210> SEQ ID NO 58
<211> LENGTH: 5
<212> TYPE: PRT
<213> ORGANISM: Artificial Sequence
<220> FEATURE:
<223> OTHER INFORMATION: A motif located proximal to the transmembrane
      domain of the Erythropoietin Receptor ("EPOR")
      protein
<220> FEATURE:
<221> NAME/KEY: VARIANT
<222> LOCATION: 3
<223> OTHER INFORMATION: Xaa = any amino acid

<400> SEQUENCE: 58

Trp Ser Xaa Trp Ser
1               5
```

TISSUE PROTECTIVE PEPTIDES AND USES THEREOF

RELATED APPLICATIONS

This application is a continuation of U.S. application Ser. No. 11/997,898, filed Oct. 29, 2008, which is a U.S. National Stage under 35 U.S.C. 371 of International Patent Application No. PCT/US2006/031061, filed Aug. 7, 2006, which claims the benefit under 35 U.S.C. 119(e) of U.S. Provisional Application No. 60/705,741, filed Aug. 5, 2005, U.S. Provisional Application No. 60/706,276, filed Aug. 8, 2005 and U.S. Provisional Application No. 60/831,737, filed Jul. 18, 2006. The contents of all the above cited patents and patent applications are hereby incorporated by reference herein in their entireties.

1. INTRODUCTION

The present invention is directed to novel tissue protective peptides. The tissue protective peptides of the invention may bind to a tissue protective receptor complex. In particular, the present invention is drawn to tissue protective peptides derived from or sharing consensus sequences with portions of cytokine receptor ligands, including Erythropoietin (EPO), that are not involved in the binding of the ligand to the receptor complex, e.g., to the EPO receptor homodimer. Accordingly, the tissue protective peptides of the invention are derived from the amino acid sequences of regions of cytokine receptor ligands that are generally located on or within the region of the ligand protein that is opposite of the receptor complex, i.e., are generally derived from amino acid sequences of regions of the ligand protein that face away from the receptor complex while the ligand is bound to the receptor. The invention is further directed to the consensus sequences for use in engineering a synthetic tissue protective peptide. These tissue protective peptides also include fragments, chimeras, as well as peptides designed to mimic the spatial localization of key amino acid residues within the tissue protective receptor ligands, e.g., EPO.

The invention also encompasses methods for treating, preventing or ameliorating a disease or disorder and or treating, restoring or ameliorating a tissue injury using tissue protective peptides of the current invention. The invention also encompasses methods for enhancing excitable tissue function using tissue protective peptides of the current invention.

2. BACKGROUND OF THE INVENTION

Erythropoietin ("EPO") is a glycoprotein hormone commonly associated with the maintenance of hematocrit and, more recently, tissue protection. Mature human EPO protein comprises 165 amino acids and has a molecular weight of 34 kDa, with glycosyl residues contributing about 40% of the weight of the molecule. The EPO molecule comprises four helices that interact via their hydrophobic domains to form a predominantly globular structure within an aqueous environment (Cheetham et al., 1998, Nat. Struct. Biol. 5:861-866, which is hereby incorporated by reference in its entirety). The invention derives from the discovery that certain amino acids facing the aqueous environment (i.e., away from the hydrophobic, globular central core) mediate tissue protection. Peptides can be derived or designed from an understanding of the tissue protective regions that have been identified by the Applicants.

As noted above, EPO is pluripotent. In its hormonal role, EPO regulates hematocrit through its role in the maturation of erythroid progenitor cells into erythrocytes. EPO acts as an anti-apoptotic agent during the maturation process of erythroid progenitor cells, permitting progenitor cells to mature into erythrocytes. Decreased levels of tissue oxygen (hypoxia) trigger an increased production of erythropoietin by the kidney, which results in increased erythropoiesis. Given that the kidney normally produces the majority of the serum erythropoietin, the loss of kidney function, such as in chronic renal failure, results in decreased production of EPO and often anemia. Similarly, anemia may result from other chronic conditions, such as cancer, or treatments associated with these illnesses, such as chemotherapy, which directly suppress the production of EPO. Commercially available recombinant erythropoietin has been available under the trademarks of PROCRIT, available from Ortho Biotech Inc., Raritan, N.J., and EPOGEN, available from Amgen, Inc., Thousand Oaks, Calif. and has been used to treat anemia resulting from end stage renal disease, therapy with AZT (zidovudine) in HIV-infected patients, oncology patients, and chemotherapy. Currently a hyperglycosylated erythropoietin, ARANESP™ (Amgen, Thousand Oaks, Calif.), is available for the treatment of anemia. Additionally, these compounds have been used to increase the hematocrits of patients undergoing surgery to reduce the need for allogenic blood transfusions.

Recently, several lines of evidence have suggested that EPO also functions locally in a paracrine-autocrine manner to minimize tissue damage. For example, EPO improves an hypoxic cellular microenvironment and decreases programmed cell death caused by metabolic stress. Both of these activities are moderated, in part, through EPO's interaction with a specific cell surface receptor comprised, in part, by the erythropoietin receptor ("EPOR") protein. EPOR is an approximately 66 kDa protein and is a member of the Type-1 cytokine receptor family. This family comprises receptors that are grouped together based on the shared homology of their extracellular domains and includes receptors for interleukin IL-2, IL3, IL4, IL5, IL6, IL7, IL9, IL11, granulocyte macrophage—colony stimulating factor (GM-CSF), granulocyte colony stimulating factor (G-CSF), leukemia inhibiting factor (LIF), ciliary neurotrophic factor (CNTF), thrombopoietin, growth hormone and prolactin. The conserved extracellular domain of these receptors has a length of approximately 200 amino acids, comprises four positionally conserved cysteine residues in the amino-terminal region (Cys 294, Cys 283, Cys 248, and Cys 238, which appear to be critical to the maintenance and the structural integrity of the receptors (Murray, 1996, Harpers Biochemistry $24^{th}$ ed. pp. 524-526, Appilion & Lange, Ltd.; Caravella et al., 1996, Protein: Struct. Funct. Gen. 24:394-401, each of which is hereby incorporated by reference in its entirety)), and a Trp-Ser-X-Trp-Ser (SEQ ID NO:58) motif located proximal to the transmembrane domain.

In connection with erythropoiesis, EPOR functions in a manner similar to other receptors within the Type-1 cytokine receptor family. First, the receptor ligand, e.g., EPO, binds to a preformed dimer of EPOR, $(EPOR)_2$. It has been determined that EPO interacts with the extracellular domain of the classic $(EPOR)_2$ homodimer receptor via two distinct regions on the ligand surface: a high affinity receptor binding site (site 1) and a low affinity receptor binding site (site 2). The amino acid sequences of EPO associated with site 1 are TKVNFY, SEQ NO:2, corresponding to amino acids 44-49 of SEQ ID NO:1, and SNFLRG, SEQ ID NO:3, corresponding to amino acids 146-151 of SEQ ID NO:1; the sequences associated with site 2 are VLERY, SEQ ID NO:4, corresponding to amino acids 11-15 of SEQ ID NO:1, and SGLRS, SEQ ID NO:5, corresponding to amino acids 100-104 of SEQ NO:1 (Cheetham et al., 1998, Nature Structural Biology 5:861-866, hereby incorporated by reference in its entirety). EPOR homodimer activation leads to tyrosine phosphorylation of signaling proteins that are associated with EPOR, e.g., Jak2 tyrosine kinases, that may in turn activate several different pathways including, for example, the phosphatidylinositol (PI) 3-kinase pathway, the Ras/MAP kinase pathway, and/or the STAT pathway. These pathways trigger the anti-apoptotic functions necessary for erythropoiesis that are mediated by erythropoietin (Kirito et al., 2002, Blood 99:102-110; Livnah et al., 1999, Science 283:987-990; Naranda et al., 2002, Endocrinology 143:2293-2302; Remy et al., 1999, Science 283:990-993; and Yoshimura et al., 1996, The Oncologist 1:337-339, each of which is hereby incorporated by reference in its entirety).

Recently, Applicants have discovered that the tissue protective properties of EPO are mediated by a receptor that comprises not only EPOR but also another receptor protein, the beta common receptor ($\beta_c$). The EPOR/$\beta_c$ receptor is, in contrast to the homodimer (EPOR)$_2$, a heterocomplex (see infra) and is known to play a role in the protection of excitable tissues. See, e.g., WO 2004/096148 and PCT no. PCT/US01/49479, filed Dec. 28, 2001, U.S. patent application Ser. No. 09/753,132, filed Dec. 29, 2000, and 10/188,905, filed Jul. 3, 2002, each of which is hereby incorporated by reference in its entirety. Although Applicants had established that the $\beta_c$ receptor is central to the tissue protective pathways in these excitable tissues, the structure of the activating ligands for the receptors was still unknown.

3. SUMMARY

The present invention is drawn to isolated polypeptides that have at least one cellular protective activity in a responsive cell, tissue, or organ, which polypeptides contain amino acid motifs comprising the consensus sequence (a) $H_1$-$N_1$-$(X)_n$-$N_2$-$H_2$, wherein $_n$ is 0, 1, 2, 3, 4 or 5; (b) $H_1$-$N_1$-$(X)_n$-$N_2$-$L_1$, wherein $_n$ is 0, 1, 2, 3, 4 or 5; (c) $L_1$-$N_1$-$(X)_n$-$N_2$-$H_1$, wherein $_n$ is 0, 1, 2, 3, 4 or 5; (d) $H_1$-$N_1$-$(L)_n$-$P_1$-$H_2$, wherein $_n$ is 0 or 1; or (e) $H_1$-$P_1$-$(L)_n$-$N_1$-$H_2$, wherein $_n$ is 0 or 1, and wherein $H_1$ and $H_2$ are hydrophobic amino acids, $N_1$ and $N_2$ are negatively charged amino acids, X is any amino acid, $L_1$ is a polar amino acid, and $P_1$ is a positively charged amino acid. In certain embodiments, the peptides of the invention also lack erythoropoietic activity, e.g., do not increase hemoglobin or hematocrit in a recipient. In further embodiments, the isolated polypeptides of the invention consist of no more than 10, no more than 15, no more than 20, or no more than 30 amino acids. In other embodiments, the isolated peptide has less than 90%, less than 85%, less than 80%, less than 75%, less than 70%, less than 65%, less than 60%, less than 55%, less than 50%, less than 45%, less than 40%, less than 35%, less than 30%, or less than 20 percent sequence identity with any portion of the amino acid sequence of mature human erythropoietin ("EPO") set forth in SEQ ID NO:1, wherein said portion of EPO contains the same number of amino acid residues as said peptide.

In certain embodiments of the invention described hereinabove, wherein the isolated polypeptide comprises the structural motif (a) $H_1$-$N_1$-$(X)_n$-$N_2$-$H_2$, wherein $_n$ is 0, 1, 2, 3, 4 or 5 (embodied by sequence identifiers 6-11, respectively, discussed infra); (b) $H_1$-$N_1$-$(L)_n$-$P_1$-$H_2$, wherein $_n$ is 0 or 1 (embodied by sequence identifiers 24-25, respectively, discussed infra); or (e) $H_1$-$P_1$-$(L)_n$-$N_1$-$H_2$, wherein is 0 or 1 (embodied by sequence identifiers 26-27, respectively, discussed infra), $H_1$ and $H_2$ may be the same hydrophobic amino acid. In other embodiments of the invention described hereinabove, wherein the isolated polypeptide comprises the structural motifs (a) $H_1$-$N_1$-$(X)_n$-$N_2$-$H_2$, wherein $_n$ is 0, 1, 2, 3, 4 or 5; (d) $H_1$-$N_1$-$(L)_n$-$P_1$-$H_2$, wherein $_n$ is 0 or 1; or (e) $H_1$-$P_1$-$(L)_n$-$N_1$-$H_2$, wherein $_n$ is 0 or 1, $H_1$ and $H_2$ may be different hydrophobic amino acids. In other embodiments, the invention provides for an isolated polypeptide comprising the amino acid motif (a) $H_1$-$N_1$-$(X)_n$-$N_2$-$H_2$, wherein $_n$ is 0, 1, 2, 3, 4 or 5; (b) $H_1$-$N_1$-$(X)_n$-$N_2$-$L_1$, wherein $_n$ is 0, 1, 2, 3, 4 or 5; (c) $L_1$-$N_1$-$(X)_n$-$N_2$-$H_1$, wherein is 0, 1, 2, 3, 4 or 5, and wherein $N_1$ and $N_2$ may the same or may be different negatively charged amino acids.

The invention provides for isolated polypeptides comprising the amino acid motifs described hereinabove, wherein said motifs are formed by consecutive amino acids within the amino-acid sequence of said polypeptide. In specific examples in accordance with this embodiment, the invention provides for an isolated polypeptide comprising the amino acid motif $H_1$-$N_1$-$N_2$-$H_2$ (SEQ ID NO:6), $H_1$-$N_1$-X-$N_2$-$H_2$ (SEQ ID NO:7), $H_1$-$N_1$-X-X-$N_2$-$H_2$ (SEQ ID NO:8), $H_1$-$N_1$-X-X-X-$N_2$-$H_2$ (SEQ ID NO:9), $H_1$-$N_1$-X-X-X-X-$N_2$-$H_2$ (SEQ ID NO:10), $H_1$-$N_1$-X-X-X-X-X-$N_2$-$H_2$ (SEQ ID NO:11), $H_1$-$N_1$-$N_2$-$L_1$ (SEQ ID NO:12), $H_1$-$N_1$-X-$N_2$-$L_1$ (SEQ ID NO:13), $H_1$-$N_1$-X-X-$N_2$-$L_1$ (SEQ ID NO:14), $H_1$-$N_1$-X-X-X-$N_2$-$L_1$ (SEQ ID NO:15), $H_1$-$N_1$-X-X-X-X-$N_2$-$L_1$ (SEQ ID NO:16), $H_1$-$N_1$-X-X-X-X-X-$N_2$-$L_1$ (SEQ ID NO:17), $L_1$-$N_1$-$N_2$-$H_2$ (SEQ ID NO:18), $L_1$-$N_1$-X-$N_2$-$H_2$ (SEQ ID NO:19), $L_1$-$N_1$-X-X-$N_2$-$H_2$ (SEQ ID NO:20), $L_1$-$N_1$-X-X-X-$N_2$-$H_2$ (SEQ ID NO:21), $L_1$-$N_1$-X-X-X-X-$N_2$-$H_2$ (SEQ ID NO:22), $L_1$-$N_1$-X-X-X-X-X-$N_2H_2$ (SEQ ID NO:23), $H_1$-$N_1$-$P_1$-$H_2$ (SEQ ID NO:24), $H_1$-$N_1$-$L_1$-$P_1$-$H_2$ (SEQ ID NO:25), $H_1$-$P_1$-$N_1$-$H_2$(SEQ ID NO:26), or $H_1$-$P_1$-$L_1$-$N_1$-$H_2$ (SEQ ID NO:27), wherein $H_1$ and $H_2$ are hydrophobic amino acids, $N_1$ and $N_2$ are negatively charged amino acids, X is any amino acid, $L_1$ is a polar amino acid, and $P_1$ is a positively charged amino acid. In certain aspects consistent with this embodiment, wherein the isolated polypeptide comprises a motif having the amino acid residues $H_1$ and $H_2$, $H_1$ and $H_2$ may the same or may be different hydrophobic amino acids. In other aspects consistent with this embodiment, wherein the isolated polypeptide comprises a motif having the amino acid residues $N_1$ and $N_2$, $N_1$ and $N_2$ may the same or may be different negatively charged amino acids.

In other embodiments, the invention provides isolated polypeptides wherein the amino acid motif is formed due to the spatial organization of amino acids within the tertiary structure of a polypeptide, i.e., the amino acids forming the motif are spatially adjacent to one another in the three dimensional structure, i.e. tertiary structure, of the polypeptide but may be separated by 1 or more amino acids within the primary amino acid sequence of the polypeptide chain. In a specific example in accordance with this embodiment, the amino acid motif comprising amino acid residues $H_1$, $N_1$, $N_2$, and $H_2$ analogous to SEQ ID NO:6, discussed supra, may form as a result of the tertiary structure adopted by, i.e., protein folding of peptides comprising, e.g., SEQ ID NO:7, SEQ ID NO:8, SEQ ID NO:9, SEQ ID NO:10 or SEQ ID NO:11, wherein the amino acid residues between $N_1$ and $N_2$, e.g. $(X)_n$, fold such that $N_1$ and $N_2$ become linearly adjacent. Accordingly, the invention encompasses isolated peptides comprising the amino acid motif $H_1N_1N_2H_2$; $H_1N_1N_2L_1$; $L_1N_1N_2H_1$; $H_1N_1(L)_nP_1H_2$, wherein n is 0 or 1; or $H_1P_1(L)_nN_1H_2$, wherein n is 0 or 1, which motifs are formed as a result of the tertiary structure of said polypeptide. In related embodiments, wherein the amino acid motif comprises $N_1$ and $N_2$, the tertiary structures form such that the distance between the carbonyl carbons of $N_1$ and $N_2$ is about 3 Å to about 5 Å, preferably about 4 Å to about 5 Å, and more preferably about 4.4 Å to about 4.8 Å. In other embodiments, wherein the amino acid motif comprises $N_1$ and $N_2$, the tertiary structures form such that the distance between $N_1$ and $N_2$ are confined spatially such that the charge separation, e.g., the charged side chains, of the two is between about 6.5 Å to about 9 Å. In a related embodiment, $N_1$ and $N_2$ are thus spatially confined as a result of being in an amino acid sequence that forms all or a portion of an alpha helix, and may be separated by 1, 2, or more than 2 amino acids in the sequence of said amino acids forming said helix. In other related embodiments, wherein the amino acid motif comprises $N_1$ and $P_1$, the tertiary structures form such that the distance between the carbonyl carbons of $N_1$ and $P_1$ is about 3 Å to about 5 Å, preferably about 4 Å to about 5 Å, and more preferably about 4.4 Å to about 4.8 Å. In other embodiments, wherein the amino acid motif comprises $N_1$ and $P_1$, the tertiary structures form such that the distance between $N_1$ and $P_1$ are confined spatially such that the charge separation, e.g., the charged side chains, of the two is between about 6.5 Å to about 9 Å. In a related embodiment, $N_1$ and $P_1$ are spatially confined as a result of being in an amino acid sequence that forms all or a portion of an alpha helix, and may be separated by 1, 2, or more than 2 amino acids in the sequence of said amino acids forming said helix. In certain embodiments, the amino acids forming the motif within the tertiary structure of said polypeptide are separated from each other by an equal number of intervening amino acid residues in the linear amino acid sequence of said polypeptide. In yet other embodiments, the amino acids forming the motif within the tertiary structure of said polypeptide are separated from each other by a different number of intervening amino acid residues in the linear amino acid sequence of said polypeptide. In certain embodiments, the isolated polypeptide of the inventions forms a regular tertiary structure, e.g., α-helix or β-pleated sheet, such that the surface of said structure presents the amino acids comprising said motif, and thus the motif itself, to the interface of the protein structure and the aqueous environment, i.e., presents the motif on the surface of folded the polypeptide. In preferred embodiments, the tertiary structures of the polypeptides of the invention form in an aqueous environment at physiological conditions, e.g., PBS (13 mM $NaH_2PO_4$, 137 mM NaCl, pH 7.4) at 37° C.

In specific embodiments, the invention provides for isolated polypeptides comprising the amino acid motifis described herein above, e.g., peptide A (APPRLICDSRVLE-RYLLEAKEAE, SEQ ID NO:32), peptide C (NITVPDT-KVNFYAWKRMEVG, SEQ ID NO:29), peptide D (QQAVEVWQGLALLSEAVLRGQALLV, SEQ ID NO:30), peptide E (GCAEHCSLNENITVPDTKVN, SEQ ID NO:31), peptide F (RYLLUNITTGC, SEQ ID NO:33), peptide G (QEQLERALNSS, SEQ ID NO:40), peptide I (CSL-NENIQEQLERALNSS, SEQ ID NO:43), peptide J (QEQLERALNSSLRRYINMLTRTR, SEQ ID NO:41), peptide K (WEHVNAIQEARRLL, SEQ ID NO:35), or peptide L (KIRSDLTALTESYVKH, SEQ ID NO:37).

In certain embodiments, the invention provides isolated polypeptides comprising 1 or more, 2 or more, 3 or more, 4 or more, 5 or more, 6 or more, or more than 6 amino acid motifs described herein. In specific aspects of the invention in accordance with this embodiment, wherein the isolated polypeptide comprises at least two of the amino acid motifs described herein above, said at least two motifs may be the same motif or they may be different motifs.

In certain aspects, the invention provides for isolated polypeptides lacking an erythropoietic activity, e.g., increasing hemoglobin in a recipient. Preferably, the isolated polypeptides lack other activities including, but not limited to, vasoactive action (e.g., vasoconstriction), hyperactivating platelets, pro-coagulant activities and stimulating proliferation and/or production of thrombocytes and/or erythropoietic-dependent cells (see, Coleman et al., 2006, PNAS 103: 5965-5970, hereby incorporated by reference in its entirety). In other aspects, the invention provides isolated polypeptides that comprise at least one cellular protective activity. Such cellular protective activity includes, but is not limited to, protecting, maintaining, enhancing or restoring the function or viability of a responsive mammalian cell, tissue, or organ. Accordingly, in one aspect, the present invention is directed to the use of an isolated polypeptide described herein for the preparation of pharmaceutical compositions for protecting, maintaining, enhancing, or restoring the function or viability of responsive mammalian cells and their associated cells, tissues, and organs. In related embodiments, the compositions are for administration to a subject in need thereof. In preferred embodiments, said subject is a mammal and, preferably, a human.

In other aspects, the present invention is directed to the use of an isolated polypeptide described herein for the preparation of a pharmaceutical composition for the protection against and/or prevention of a responsive tissue injury, for the restoration of, or for the rejuvenation of responsive tissue and/or responsive tissue function in a subject in need thereof. In one particular aspect, the responsive mammalian cells and their associated cells, tissues, or organs are distal to the vasculature by virtue of a tight endothelial cell barrier. In another particular aspect, the cells, tissues, organs or other bodily parts are isolated from a mammalian body, such as those intended for transplant. By way of non-limiting examples, a responsive cell or tissue may be neuronal, eye (e.g., retinal), adipose, connective, hair, teeth, mucosal, pancreas, endocrine, ear, epithelial, skin, muscle, heart, lung, liver, kidney, intestine, adrenal (e.g., adrenal cortex, adrenal medulla), capillary, endothelial, testes, ovary, bone, skin, or endometrial cells or tissue. Further, non-limiting examples of responsive cells include photoreceptor (rods and cones), ganglion, bipolar, horizontal, amacrine, Müller, Purkinje, myocardium, pace maker, sinoatrial node, sinus node, junction tissue, atrioventricular node, bundle of His, hepatocytes, stellate, Kupffer, mesangial, renal epithelial, tubular interstitial, goblet, intestinal gland (crypts), enteral endocrine, glomerulosa, fasciculate, reticularis, chromaffin, pericyte, Leydig, Sertoli, sperm, Graffian follicle, primordial follicle, islets of Langerhans, α-cells, β-cells, γ-cells, F-cells, osteoprogenitor, osteoclasts, osteoblasts, endometrial stroma, endometrial, stem and endothelial cells. These examples of responsive cells are merely illustrative. In one aspect, the responsive cell or its associated cells, tissues, or organs are excitable cells, tissues, or organs, or predominantly comprise excitable cells or tissues. In certain aspects of the invention, the excitable tissue is central nervous system tissue, peripheral nervous system tissue, cardiac tissue or retinal tissue. In another aspect, the responsive cell or its associated cells, tissues, or organs are not excitable cells, tissues, or organs, nor do they predominantly comprise excitable cells or tissues.

The erythropoietic and/or cellular protective activity of the isolated polypeptide of the invention in responsive cells may be evaluated and/or determined by any method described herein and or known in the art. In certain embodiments, the erythropoietic and/or cellular protective activity is determined in an in vitro assay. In other embodiments, the erythropoietic and/or cellular protective activity is determined in an in vivo assay. In a related embodiment, wherein the cellular protective activity is neuroprotection, the invention provides for a method of evaluating said activity in vitro by (a) contacting a test culture of primary hippocampal neurons with N-methyl-D-aspartate and said peptide; and (b) determining the cell viability at 48 hours post said contact, such that if the cell viability determined in step (b) is greater than that of a control culture in the absence of said peptide, the peptide possesses cellular protective activity.

In a particular embodiment, the mammalian cell, tissue, or organ for which an aforementioned isolated peptide is used are those that have expended or will expend a period of time under at least one condition adverse to the viability of the cell, tissue, or organ. In accordance with this embodiment, the isolated peptides of the invention provide protection against and/or prevention of a tissue injury resulting from such conditions, provide for the restoration of, or provide for the rejuvenation of tissue and/or tissue function in a subject in need thereof before, during or after such conditions arise. Such conditions include traumatic in situ hypoxia or metabolic dysfunction, surgically-induced in situ hypoxia or metabolic dysfunction, or in situ toxin exposure, the latter may be associated with chemotherapy or radiation therapy. In other embodiments, the isolated peptides of the invention provide protection against and/or prevention of a tissue injury resulting from a disease or disorder, provide for the restoration of, or provide for the rejuvenation of tissue and/or tissue function in a subject in need thereof before, during or after such conditions arise. In related embodiments said injury is caused by a seizure disorder, multiple sclerosis, stroke, hypotension, cardiac arrest, ischemia, myocardial infarction, inflammation, age-related loss of cognitive function, radiation damage, cerebral palsy, neurodegenerative disease, Alzheimer's disease, Parkinson's disease, mitochondrial disease, AIDS dementia, memory loss, amyotrophic lateral sclerosis, alcoholism, mood disorder, anxiety disorder, attention deficit disorder, autism, Creutzfeld-Jakob disease, brain or spinal cord trauma or ischemia, heart-lung bypass, chronic heart failure, macular degeneration, diabetic neuropathy, diabetic retinopathy, hepatitis, pancreatitis, glaucoma, retinal ischemia, retinal trauma, cardiovascular disease, cardiopulmonary disease, respiratory disease, kidney disease, disease of the urinary system, disease of the reproductive system, bone disease, skin disease, connective tissue disease, gastrointestinal disease, endocrine abnormality, metabolic abnormality, or a disease or disorder of the central or peripheral nervous system. In still other embodiments, the adverse conditions are a result of cardio-pulmonary bypass (heart-lung machine), as is used for certain surgical procedures. In still other embodiments, said injury is cognitive dysfunction. In a particular embodiment, the mammalian cell, tissue, or organ for which an aforementioned isolated peptide is used express the βc receptor.

In certain embodiments, the invention is also directed to pharmaceutical compositions comprising the aforementioned isolated polypeptides for administration to a subject in need thereof. In specific aspects in accordance with this embodiment, the pharmaceutical composition of the invention further comprises a pharmaceutically acceptable carrier. Such pharmaceutical compositions may be formulated for oral, intranasal, ocular, inhalational, transdermal, rectal, sublingual, vaginal, or parenteral administration, or in the form of a perfusate solution for maintaining the viability of cells, tissues, or organs ex vivo. In related embodiments of the invention the subject is a mammalian animal, preferably a human.

In other aspects, the invention provides a method for facilitating the transcytosis of a molecule across an endothelial cell barrier in a subject in need thereof comprising administration to said subject a composition comprising said molecule in association with an isolated peptide of the invention described hereinabove. In a related embodiment, association is a labile covalent bond, a stable covalent bond, or a non-covalent association with a binding site for said molecule.

According to another aspect of the invention, the isolated peptide of the invention, as described herein above, is capable of traversing an endothelial cell barrier. In a related embodiment, the endothelial cell barrier comprises the blood-brain barrier, the blood-eye barrier, the blood-testis barrier, the blood-ovary barrier, blood-placenta, blood-heart, blood-kidney, blood-nerve, or blood-spinal cord barrier.

According to one aspect of the invention, there is provided an isolated nucleic acid molecule that comprises a nucleotide sequence which encodes a polypeptide comprising the isolated polypeptide as described herein above.

In another embodiment of the invention, there is provided an isolated nucleic acid molecule that comprises a nucleotide sequence (i.e., a cDNA, a nucleotide sequence interrupted by introns, or uninterrupted by introns), which encodes a polypeptide comprising or consisting of the isolated polypeptide of the invention as described herein above. In one embodiment, the nucleotide sequence, encoding the isolated polypeptide of the invention, is synthesized using preferred codons that facilitate optimal expression in a particular host cell. Such preferred codons can be optimal for expression in cells of a species of plant, bacterium, yeast, mammal, fungus, or insect.

The invention also provides for a vector comprising the nucleic acid molecule. The invention also provides for an expression vector comprising the nucleic acid molecule and at least one regulatory region operably linked to the nucleic acid molecule. In another embodiment, the invention provides for a cell comprising the expression vector. In yet another embodiment, there is provided a genetically-engineered cell which comprises the nucleic acid molecule.

In another embodiment, the invention provides for a method of recombinantly producing the isolated peptide of the invention, described herein above, comprising culturing in a medium a host cell containing a nucleic acid molecule comprising a nucleotide sequence encoding a polypeptide of the invention, under conditions suitable for the expression of said peptide, and recovering and/or isolating the expressed polypeptide from said medium.

3.1 Terminology

As used herein, the terms "about" or "approximately" when used in conjunction with a number refer to any number within 1, 5, or 10% of the referenced number.

The term "administered in conjunction with" in the context of the methods of the invention means administering a compound prior to, at the same time as, and/or subsequent to the onset of a disease, disorder, or condition.

The term "amino acid" or any reference to a specific amino acid is meant to include naturally occurring proteogenic amino acids as well as non-naturally occurring amino acids such as amino acid analogs. Those skilled in the art would know that this definition includes, unless otherwise specifically noted, includes naturally occurring protogenic (L)-amino acids, their optical (D)-isomers, chemically modified amino acids, including amino acid analogs such as penicillamine (3-mercapto-D-valine), naturally occurring non-proteogenic amino acids such as norleucine and chemically synthesized proteins that have properties known in the art to be characteristic of an amino acid. As used herein, amino acids will be represented wither by their three letter acronym or one letter symbol as follows: alanine=Ala or A, arginine=Arg or R, asparagine=Asn or N, aspartic acid=Asp or D, cysteine=Cys or C, glutamic acid=Glu or E, glutamine=Gln or Q, glycine Gly or G, histidine=His or H, isoleucine=Ile or I, leucine=Leu or L, lysine=Lys or K, methionine=Met or M, phenylalanine=Phe or F, proline=Pro or P, serine=Ser or S, threonine Thr or T, tryptophan=Trp or W, tyrosine=Tyr or Y, and valine=Val or V. Additionally, the term "amino acid equivalent" refers to compounds that depart from the structure of the naturally occurring amino acids, but which have substantially the structure of an amino acid, such that they can be substituted within a peptide, which retains its biological activity despite the substitution. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents. Amino acids may also be classified into the following groups as is commonly known in the art: (1) hydrophobic amino acids: His, Trp, Tyr, Phe, Met, Leu, Ile, Val, Ala; (2) neutral hydrophilic amino acids: Cys, Ser, Thr; (3) polar amino acids: Ser, Thr, Asn, Gln; (4) acidic/negatively charged amino acids: Asp, Glu; (5) charged amino acids: Asp, Glu, Arg, Lys, His; (6) positively charged amino acids: Arg, Lys, His; and (7) basic amino acids: His, Lys, Arg.

As used herein, "excitable tissue" means tissue that contains excitable cells. Excitable cells are cells that respond actively to an electric stimulus and have an electrical charge differential across their cellular membranes. Excitable cells are generally capable of undergoing an action potential. Such cells typically express channels, such as voltage-gated, ligand-gated, and stretch channels, which allow flow of ions (potassium, sodium, calcium, chloride, etc.) across the membrane. Excitable tissue includes neuronal tissue, muscle tissue, and glandular tissue. Excitable tissue includes, but is not limited to, neuronal tissues such as tissue of the peripheral nervous system (ear and retina) and central nervous system (brain and spinal cord); cardiovascular tissue such as the cells of the heart and associated nerves; and glandular tissue such as the pancreas where T-type calcium channels along with cell-to-cell gap junctions participate in secretion of insulin. An exemplary list of excitable tissue includes organs and tissues that include nerves, skeletal muscle, smooth muscle, cardiac muscle, uterus, central nervous system, spinal cord, brain, retina, olfactory system, auditory system, etc.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

An "isolated" or "purified" polypeptide is substantially free of cellular material or other contaminating proteins from the cell or tissue source from which the protein or polypeptide is derived, or substantially free of chemical precursors or other chemicals when chemically synthesized. The language "substantially free of cellular material" includes preparations of a polypeptide in which the polypeptide is separated from cellular components of the cells from which it is isolated or recombinantly produced. Thus, a polypeptide that is substantially free of cellular material includes preparations of polypeptides having less than about 30%, 20%, 10%, or 5% (by dry weight) of heterologous protein (also referred to herein as a "contaminating protein"). When the polypeptide is recombinantly produced, it is also preferably substantially free of culture medium, i.e., culture medium represents less than about 20%, 10%, or 5% of the volume of the protein preparation. When the polypeptide is produced by chemical synthesis, it is preferably substantially free of chemical precursors or other chemicals, i.e., it is separated from chemical precursors or other chemicals which are involved in the synthesis of the protein. Accordingly such preparations of the polypeptide have less than about 30%, 20%, 10%, 5% (by dry weight) of chemical precursors or compounds other than the antibody of interest. In a preferred embodiment, polypeptides of the invention are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding a polypeptide of the invention is isolated or purified.

As used herein in reference to a structure within a polypeptide, the term "motif" refers either to a set of consecutive amino acids within the amino acid sequence of the polypeptide chain and/or to a set of linearly adjacent amino acids within the tertiary structure of said polypeptide. Because the motif may be formed all or in part as a result of protein folding, amino acids that are adjacent in the described motif may be separated by 0, 1 or more, 5 or more, 10 or more, 15 or more or 20 or more amino acids within the linear amino acid sequence of the polypeptide.

As used herein, the terms "peptide," "polypeptide" and "protein" are used interchangeably and in their broadest sense to refer to constrained (that is, having some element of structure as, for example, the presence of amino acids which initiate a β turn or β pleated sheet, or for example, cyclized by the presence of disulfide bonded Cys residues) or unconstrained (e.g., linear) amino acid sequences. In certain embodiments, the peptide of the invention consists of less than 30 amino acids. However, upon reading the instant disclosure, the skilled artisan will recognize that it is not the length of a particular peptide but its ability to bind a tissue protective receptor complex and/or compete with the binding of a peptide described herein that distinguishes the peptide of the invention. The terms "peptide," "polypeptide," d "protein" also refer to compounds containing amino acid equivalents or other non-amino acid groups, while still retaining the desired functional activity of a peptide. Peptide equivalents can differ from conventional peptides by the replacement of one or more amino acids with related organic acids (such as PABA), amino acids or the like or the substitution or modification of side chains or functional groups.

The term "preventing a disease, disorder, or condition" means delaying the onset, hindering the progress, hindering the appearance, protection against, inhibiting or eliminating the emergence, or reducing the incidence, of such disease, disorder, or condition. Use of the term "prevention" is not meant to imply that all patients in a patient population administered a preventative therapy will never develop the disease, disorder, or condition targeted for prevention, but rather that the patient population will exhibit a reduction in the incidence of the disease, disorder, or condition. For example, many flu vaccines are not 100% effective at preventing flu in those administered the vaccine. One skilled in the art can readily identify patients and situations for whom preventative therapy would be beneficial, such as, but not limited to, individuals about to engage in activities that may lead to trauma and injury (e.g., soldiers engaging in military operations, race car drivers, etc.), patients for whom surgery is planned, patients at risk for inherited diseases, disorders, or conditions, patients at risk for diseases, disorders, or conditions precipitated by environmental factors, or portions of the population at risk for particular diseases, disorders, or conditions such as the elderly, infants, or those with weakened immune systems, or those patients with genetic or other risk factors for a disease, disorder, or condition.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a non-primate (e.g., a monkey or a human), and more preferably a human.

As used herein, the term "tissue protective activity" or "tissue protection" refers to the effect of inhibiting or delaying damage or death of a cell, tissue, or organ. Unless otherwise noted, the "delay" in damage or death of a cell, tissue or organ is evaluated relative to a control condition in the absence of a peptide of the invention. The tissue protective activity is useful in various conditions, diseases, and cellular, organ, and/or tissue damage, for example, those described in section 5.3. Tissue protective activity is specific to tissue, cells, and/or organs expressing a tissue protective receptor complex (i.e., a responsive tissue cell, and.or organ, respectively), such as, but not limited to, the tissues of the central nervous system. In specific embodiments, the responsive cells are not erythrocyte progenitor cells.

The term "tissue protective receptor complex" as used herein means a complex comprising at least one erythropoietin receptor subunit and at least one beta common receptor subunit. The tissue protective receptor complex may contain multiple erythropoietin receptor subunits and/or beta common receptor subunits, as well as other types of receptors or proteins. See WO 2004/096148, which is hereby incorporated by reference herein in its entirety.

To determine the percent identity of two amino acid sequences, the sequences are aligned for optimal comparison purposes. The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical overlapping positions/total number of positions X 100%). In one embodiment, the two sequences are the same length. In an alternate embodiment, the sequences are of different length and, accordingly, the percent identity refers to a comparison of the shorter sequence to a portion of the longer sequence, wherein said portion is the same length as said shorter sequence.

4. BRIEF DESCRIPTION OF THE FIGURES

FIG. 1 depicts the results of an in vivo sciatic nerve injury model to compare the efficacy of peptide J (SEQ ID NO:41) to the tissue protective molecule carbamylated EPO (CEPO), wherein peptide J, SEQ ID NO:41, is a chimeric peptide consisting of the external facing amino acids of helix B of EPO (i.e., peptide G, SEQ ID NO:40) combined with an amphipathic helix from pancreatic polypeptide (LRRYINMLTRP, SEQ ID NO:28)

FIG. 2 depicts the tissue protective effects of peptides of the invention as tested in an in vivo sciatic nerve injury model. In the assay, the right sciatic nerve of rats (n=6 per group) was injured and the animal immediately dosed with PBS, or PBS containing equal molar concentrations of carbamylated EPO, EPO peptide A (SEQ ID NO:32, corresponding to amino acids 1-23 of SEQ ID NO:1), peptide D (SEQ ID NO:30, corresponding to amino acids 58-82 of SEQ ID NO:1), or peptide G (SEQ ID NO:40). Peptide G (SEQ ID NO:40) is based on those amino acids within Helix B of EPO that face outward from the globular center of the EPO molecule into the hydrophilic environment, i.e., present on the surface of the polypeptide. Additionally, a 20-mer constructed from a region of pigment epithelium-derived factor known to be tissue protective via another receptor was included as a negative control. The recovery from injury over the next 4 days demonstrates that peptide G, SEQ ID NO:40, and peptide D, SEQ ID NO:30, exhibit a tissue protective effect in this in vivo model assay that is equivalent to or better than carbamylated EPO (CEPO).

FIG. 3 depicts the erythropoietic effects of peptide D, SEQ ID NO:30, and CEPO, known to lack erythropoietic activity, as tested in a UT-7 assay for erythropoietic activity. The results of this in vitro assay demonstrate that neither peptide D, SEQ ID NO:30, nor CEPO exhibit erythropoietic activity at doses up to 10,000 pM.

FIG. 4 depicts the results of an in vivo assay to determine whether peptide F (SEQ ID NO:33, corresponding to amino acids 14-29 of SEQ ID NO:1) and peptide G (SEQ ID NO:40) are erythropoietic or elicit neutralizing antibodies against EPO. The results demonstrate that neither protein increased hemoglobin levels in the rats when administered at 0.8 µg/kg, 3 days/week sub-cutaneously (s.c.) over the course of 130 days. In addition, neither peptide elicits an antibody response, in contrast to the administration of EPO.

Figure 7A:
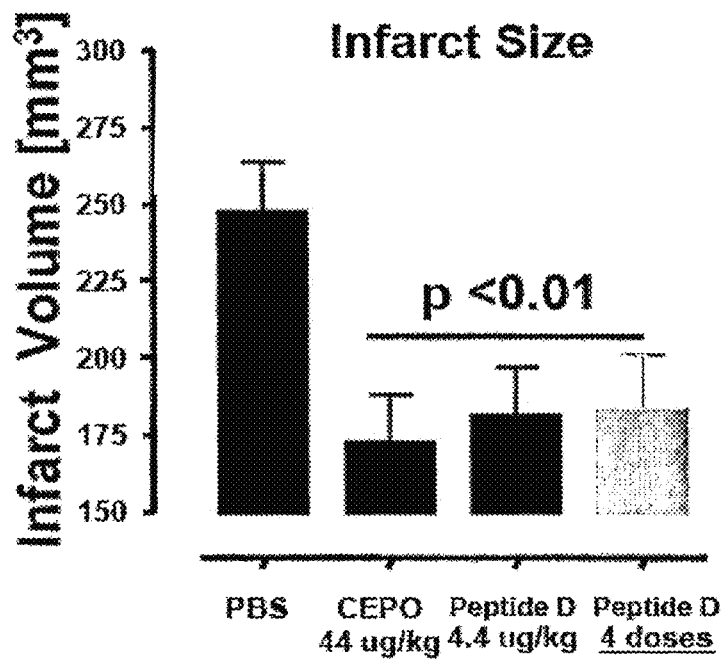
Figure 7B:
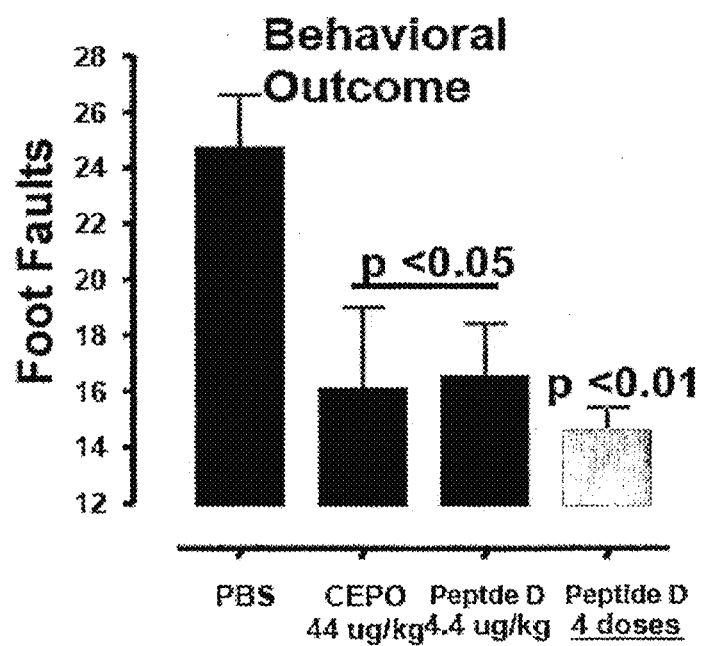

FIGS. 7 A-B depict the results of a middle cerebral artery occlusion assay in rats. FIG. 7A depicts a graph demonstrating that peptide D (SEQ ID NO:30, corresponding to amino acids 58-82 of SEQ ID NO:1) at a single dose of 4.4 ug/kg is able to reduce the volume of the infarct in the brain as robustly as four doses of 4.4 ug/kg administered 2 hours apart. FIG. 7B depicts the results of a foot fault assay to determine the behavioral deficit caused by the middle cerebral artery occlusion. FIG. 7B shows that rats demonstrated behavioral improvements when administered peptide D, SEQ ID NO:30, at both a single dose schedule (1×4.4 ug/kg) and a multiple dose schedule (4×4.4 ug/kg).

Figure 8A:
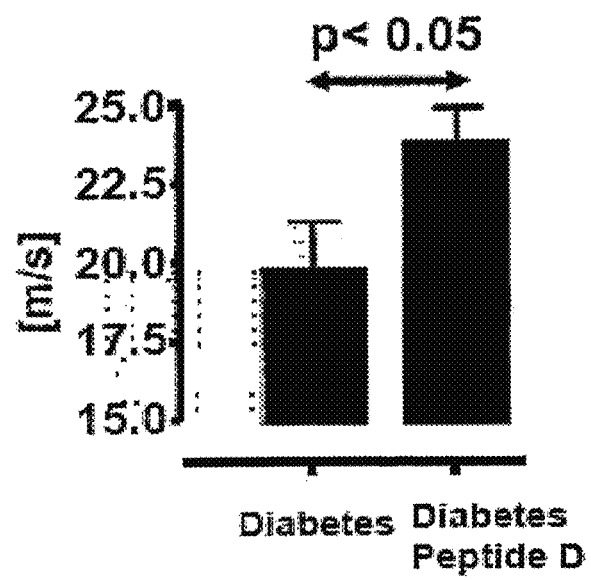
Figure 8B:
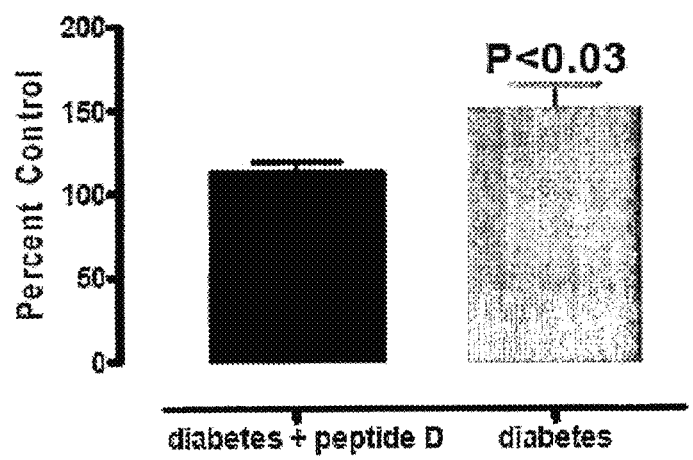

FIGS. 8 A-B depict the results of an in vivo assay of a diabetic neuropathy assay. Diabetes is induced in rats using streptozotocin. After verification of induced diabetes, the rats were treated with peptide D, SEQ ID NO:30, or PBS five times a week at a dose of 4 ug/kg-bw i.p. for a period of two weeks. Both the nerve conduction velocity and the hot plate latency of the rats were observed. FIG. 8A demonstrates that the rats treated with peptide D, SEQ ID NO:30 exhibited improved conduction velocities in comparison to the untreated rats. FIG. 8B demonstrates that hotplate latency for the treated rats was reduced relative to the untreated rats, further demonstrating the improvement in conduction velocity.

Figure 9A:
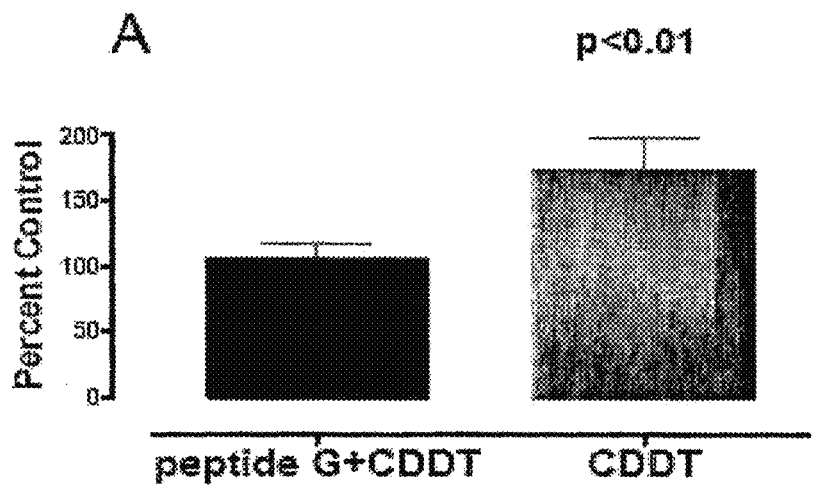
Figure 9B:
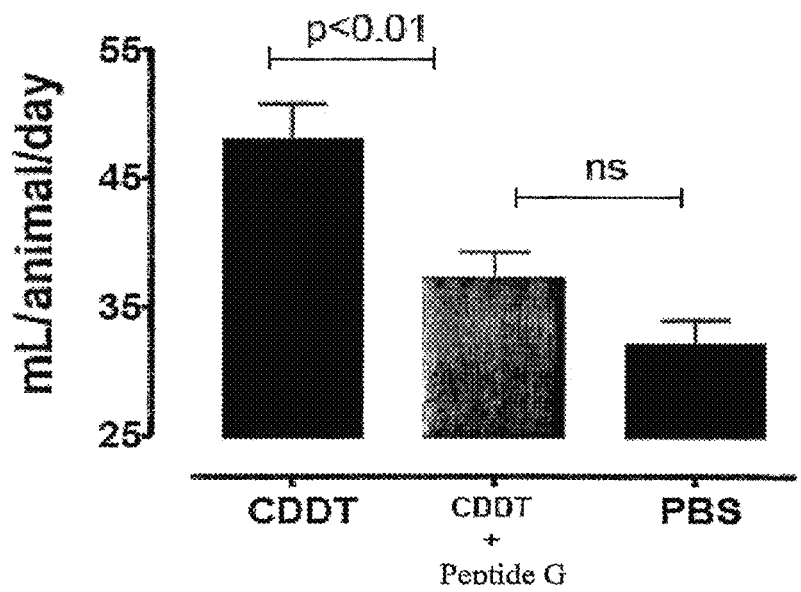

FIGS. 9 A-B depict the results of treatment of cisplatin induced neuropathy and nephropathy with EPO Helix B chimera. FIG. 9A demonstrates that the animals treated with peptide G (SEQ ID NO:40, a Helix B chimera) exhibited improved results when tested in a hotplate latency assay. FIG. 9B demonstrates that the urine production, a measure of kidney function, was maintained as normal in the peptide G (SEQ ID NO:40) treated animals.

Figure 10:
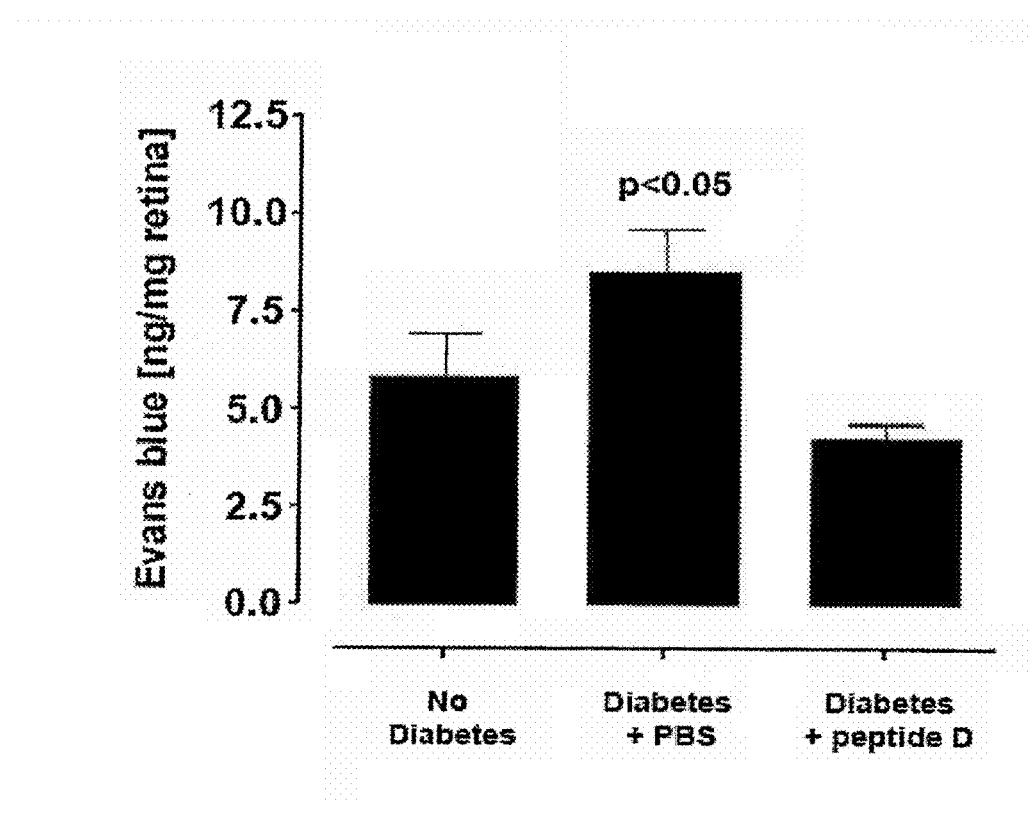

FIG. 10 depicts the effects of peptide D (SEQ ID NO:30) on retinal leakage associated with diabetic retinopathy. The figure demonstrates that peptide D (SEQ ID NO:30) was able to substantially reduce retinal leakage in the treated animals.

Figure 11:
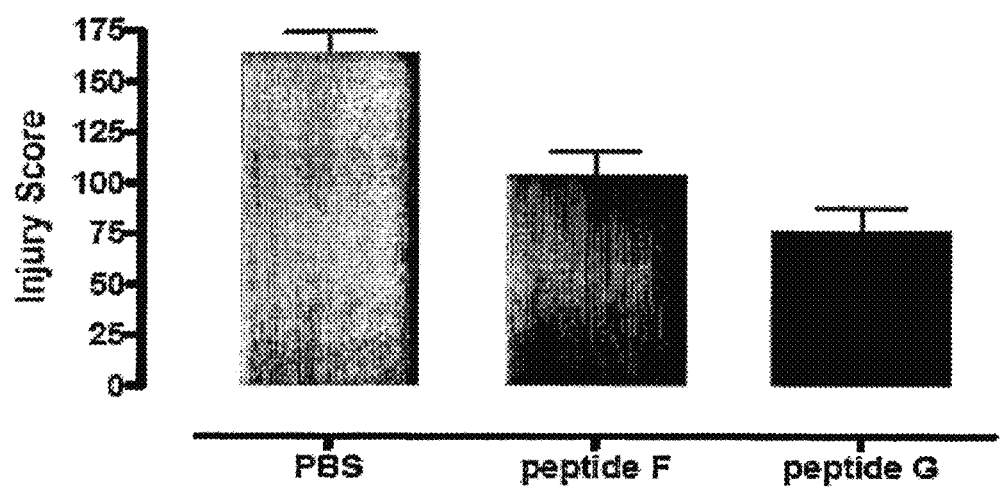
Figure 12:
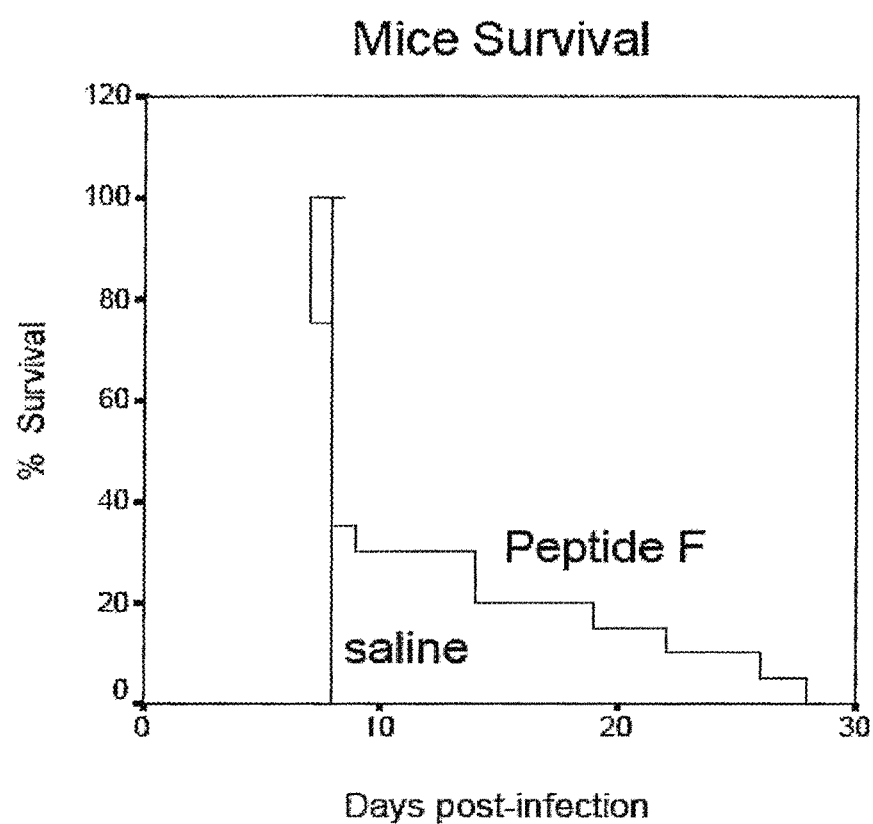

FIG. 11 depicts the results of peptide F (SEQ ID NO:33) or peptide G (SEQ ID NO:40) on a model of kidney ischemia-reperfusion. The figure demonstrates that both peptides reduced the injury score resulting from an ischemia-reperfusion injury of 60 minutes when assessed after 72 hours FIG. 12 illustrates that the administration of peptide F (SEQ ID NO:33) protects mice from experimental cerebral malaria.

Figure 13:
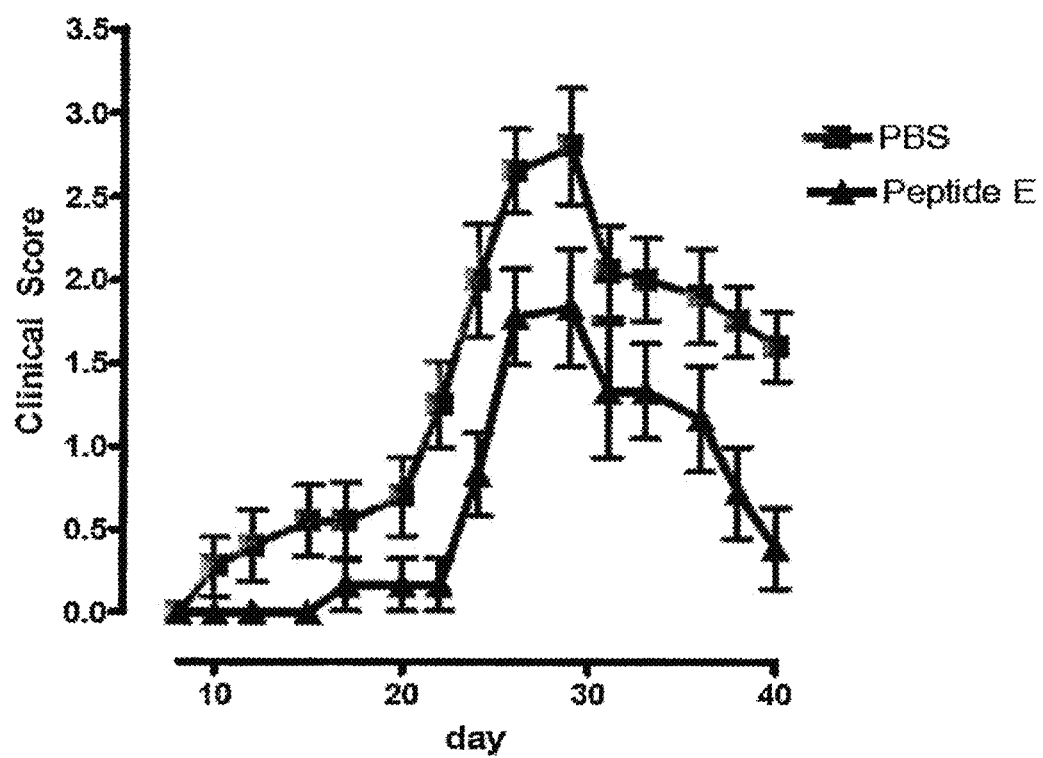

FIG. 13 Clinical Score in murine EAE model treated with Peptide E, SEQ ID NO:31. FIG. 13 depicts the clinical course of neurological function in mice with experimental autoimmune encephalomyelitis. 4.4 µg/kg Peptide E was administered i.p. daily. Administration of peptide E significantly improved neurological function relative to control. Clinical staging; 1, flaccid tail; 2, ataxia and/or hind-limb paresis, or slow righting reflex; 3, paralysis of hind limb and/or paresis of forelimbs; 4, paresis of forelimb; 5, moribund or death.

5. DETAILED DESCRIPTION OF THE INVENTION

5.1 Tissue Protective Peptides

The erythropoietic activity of erythropoietin ("EPO") has been well characterized in the art (see, e.g., Cheetham et al., 1998, Nat. Struct. Biol. 5; 861-866, herein incorporated by reference in its entirety). EPO initiates erythropoiesis by binding to the extracellular portion of a preformed erythropoietin receptor (EPOR) homodimer (i.e., $(EPOR)_2$) in a manner that bridges between specific locations on the individual EPOR subunits. When EPO binds to the $(EPOR)_2$, large portions of the globular ligand are remote from the binding regions and face outward, away from the complex of EPO and $(EPOR)_2$ into the aqueous medium. The Applicants have determined that tissue protection, as distinct from erythropoiesis, is mediated through a receptor other than $(EPOR)_2$, which consists of an EPOR monomer in conjunction with another receptor, CD131 (also known as the β-common receptor subunit ($β_c$)). EPOR and $β_c$ interact to form the receptor heterodimer, EPOR-$β_c$. Whether other proteins are involved in this interaction is currently unknown. The instant invention discloses tissue protective peptides derived from the three dimensional structure of EPO, and in particular, from the portions of EPO facing away from the EPOR binding sites, i.e., not interacting with, the classical, erythropoietic EPOR $(EPOR)_2$ homodimer. Not wishing to be bound by any particular theory, the Applicants believe that this portion of the EPO molecule interacts with the tissue protective receptor and thereby mediates tissue protection.

The three dimensional structure of EPO is accepted as described by Cheetham et al., 1998, Nat. Struct. Biol. 5; 861-866, hereby incorporated by reference in its entirety, and as set forth in SEQ ID NO:1 (also available as data deposited in the Protein Data Bank of the National Center for Biotechnology Information as entry "1BUY"). The portions of the EPO molecule that face away from the membrane-proximal portion of the EPOR homodimer when bound to said receptor (i.e., away from the cell membrane when the $(EPOR)_2$ homodimer is expressed on the surface of a cell) consist of the following secondary structures: loop AB (corresponding to amino acids 29-55 of SEQ ID NO:1), helix B (corresponding to amino acids 56-82 of SEQ ID NO:1), loop BC (corresponding to amino acids 83-92 of SEQ ID NO:1) and loop CD (corresponding to amino acids 112-138 of SEQ ID NO:1). In one embodiment of the invention, the tissue protective peptides consist of the amino acid sequences corresponding to these distinct structures of the EPO molecule.

Not wishing to be bound to any particular theory, the Applicants believe that the Tissue Protective Receptor is preformed, i.e. that the EPOR and $β_c$ protein subunits are functionally associated prior to their interaction with EPO. EPO is a member of the type I cytokine superfamily. Members of type 1 cytokine superfamily branch are characterized by four helices which interact hydrophobically to form a globular protein whose exterior surface interfaces with the aqueous medium and is termed "externally-facing". Unexpectedly, the Applicants have determined that more than one peptide derived from the externally-facing portion of the EPO molecule is tissue-protective. A further surprising discovery is that peptides derived from portions of the EPO molecule that are buried within the EPO:$(EPOR)_2$ complex and peptides that may also contain portions of erythropoiesis binding sites 1 or 2 are also be highly potent in tissue protection. To account for these discoveries, Applicants propose that successful activation of the tissue protective receptor is due to an appropriate, spatially compact charge configuration within the peptide ligand. Further, this compact charge configuration is embodied by two distinct structural motifs: (1) two negatively charged amino acids adjacent to each other, and flanked by hydrophobic amino acids; or (2) a positive and a negative (i.e., basic and acidic) amino acid immediately adjacent to one another, and flanked by single hydrophobic or polar amino acid residues. The proximity of these charges may occur via the linear structure imposed by peptide bonding, i.e., the structure may be formed by consecutive amino acids in a polypeptide chain, or alternatively, proximity can also occur via a spatial relationship between different parts of the EPO molecule (or other related type 1 cytokine molecules) imparted by the protein's tertiary structure, i.e., three dimensional structure. Not wishing to be bound to any specific theory, Applicants believe that, in general, this requirement dictates that a tissue protective peptide will have a distinct tertiary structure (e.g., helices or pleated sheets) that provides for the required spatial location of the pair of charged amino acids (i.e., the two negatively charges amino acids and/or the positive and negative amino acid). A simple exception is a linear peptide wherein the amino acid pair is immediately adjacent to each other, with the required rigidity imparted by the peptide backbone. Accordingly, the structural motif (1), is encompassed by a linear sequence of amino acid residues, e.g., $H_1$-$N_1$-$N_1$-$H_2$ (SEQ ID NO:6), or by a linear sequence of amino acid residues wherein $N_1$ and $N_2$ are separated by 1, 2, 3, 4, 5, 6, or more intervening residues, e.g., $H_1$-$N_1$-X-X-X-X-X-$N_1$-$H_2$ (SEQ ID NO:11).

For tissue protection, the pair of charged amino acids must be spatially oriented such that the carbonyl carbons are about 3 angstroms (Å) to about 5 Å apart, preferably, about 4 Å to about 5 Å apart, and more preferably about 4.4 Å to about 4.8 Å apart. This can be accomplished in a number of ways, for example, by adjacent charged amino acids in a simple linear peptide (see, e.g., Example 2 and peptide G, SEQ ID NO:40, Table 1) or for peptides that can form an alpha helix, charged amino acids separated by an intervening amino acid residue (see, e.g., Example 2 and peptide F, SEQ ID NO:33, Table 1). It is to be noted that tertiary structure (e.g., an alpha helix in amphipathic peptides) can also be imparted when the peptide is within a specific microenvironment, such as at the extracellular-cell surface membrane interface (see, Segrest, 1990, Proteins 8:103-117, hereby incorporated by reference in its entirety).

Further, tissue protective activity is predicted for peptides that contain pairs of charged amino acids such that the charged side-chains (either positive and negative or two negatives) be confined spatially to within about 6.5 Å to about 9 Å of each other. This can be provided for in an alpha helix by the charged pair being separated by one or two amino acids, which will provide for the charges to be more or less on the same side of the helix with the required about 6.5 Å to about 9 Å separation. A non-limiting example of such a peptide is found in peptide F (see, Example 2, SEQ ID NO:33, Table 1). One skilled in the art can devise a tertiary structure for the peptide that is generally required to obtain the appropriate three dimensional location of the charged amino acids, as well as the design of small molecules to mimic the charge separation within the peptide.

The spatial distances between the carbamyl carbons of any to amino acids or between the side chains of any two amino acids can be deduced by any method known in the art or described herein. For example, where the three-dimensional structure of the protein is known, the charge separation of two side chains or the spatial distance between two carbamyl carbons within a portion of interest of said protein can be calculated based on the published, or otherwise art-accepted, three-dimensional coordinates of the amino acid residues in said portion of interest. Where the three-dimensional structure of the protein and, therefore, the portion of interest is unknown, or wherein a fully synthetic peptide is constructed based on the teachings herein, whose three dimensional structure is unknown, the charge separation of two side chains or the spatial distance between two carbamyl carbons within said peptide can be estimated using the three-dimensional structure predicted by protein modeling software as is known in the art. Non-limiting examples of such software are MOE™ by Chemical Computing Group (Quebec, Canada) and Modeler by Accelrys (San Diego, Calif.). Similarly such predictive software, available from the above-noted companies as well, is also known in the art for the design of small molecules as and, accordingly, one of ordinary skill in the art, based upon the teachings herein, would be able to make small molecules that emulate the disclosed structural motifs.

Non-naturally occurring or chimeric peptides can be designed that mimic the critical spatial proximities described herein above via a linear sequence of amino acids. The present invention is, therefore, directed to novel tissue protective peptides, including those that exhibit these structural motifs that trigger tissue protection.

The present invention also relates to the use of tissue protective fragments of other type 1 cytokines, including, but not limited to, granulocyte-macrophage colony stimulating factor (GM-CSF), interleukin-3 (IL-3), Thrombopoietin (TPO), Ciliary Neurotrophic Factor (CNTF) and Leukemia Inhibitory Factor (LIF), that are structurally homologous with the above noted externally-presenting amino acid sequences of EPO and/or contain the structural motifs described above.

Further, the tissue protective peptides may be chimeric compounds based upon structural motifs described above combining non-adjacent structural elements and surface presenting amino acids solely. In particular, the applicants have determined that the addition of an amphipathic peptide helix to the above noted sequences increases the potency of the peptide.

Additionally, the tissue protective peptides of the present invention include fusion peptides resulting from the combination of two or more of the above noted peptides, or with a related or unrelated macromolecule for specific transport, such as native EPO, insulin or leptin.

5.1.1 Fragments

A. EPO-Derived Peptide Fragments

Figure 1:
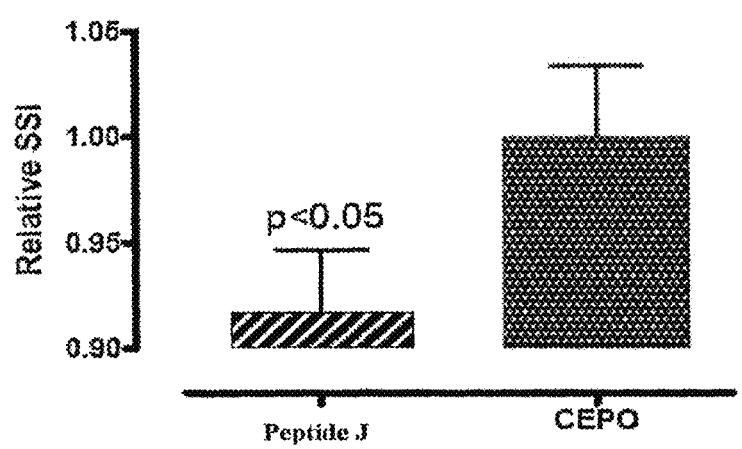

The present invention relates to novel tissue protective peptides that in one embodiment are comprised of fragments of the amino acid sequences of EPO, derived from the three dimensional structure of the EPO protein, and in particular, were derived from those regions of EPO facing away from the ligand binding sites and/or the internal portion of the EPOR homodimer. These fragments are derived from the following EPO structures: (1) loop AB and N-terminal portion of helix B (NITVPDTKVNFYAWKRMEVG, SEQ ID NO:29, corresponding to amino acids 38-57 of SEQ ID NO:1); (2) C-terminal portion of helix B (QQAVEVWQGLALLSEAVL-RGQALLV, SEQ ID NO:30, corresponding to amino acids 58-82 of SEQ ID NO:1), and (3) a portion of the A-B loop consisting of a small cysteine loop and a β-pleated sheet (GCAEHCSLNENITVPDTKVN, SEQ ID NO:31, corresponding to amino acids 28-47 of SEQ ID NO:1). These peptide fragments are all demonstrated in Example 2 (see FIG. 1 and Table 1) to exhibit tissue protective properties.

Unexpectedly, some peptides derived from other regions of the EPO molecule that are buried and other peptides that include portions of the binding sites to $(EPOR)_2$ are also tissue protective. For example, a peptide consisting of the N-terminal portion of Helix A (APPRLICDSR VLERYLLEAKEAE, SEQ ID NO:32, corresponding to amino acids 1-23 of SEQ ID NO:1) that contains a portion of EPOR binding Site 2 (underlined) is tissue protective (see Example 2 and Table 1). However, the presence of Site 2 amino acids does not account for the tissue protective activity, as a peptide consisting of amino acids 14-19 of SEQ ID NO:1 (RYLLEAKEAENITTGC, SEQ ID NO:33) and lacking amino acids 11-13 of SEQ ID NO:1 (i.e., VLE; the site 2 amino acids that are required for binding of EPO to the EPOR dimer, $(EPOR)_2$, is also tissue protective (see, Example 2 and Table 1, also Elliott et al., 1997, Blood 89:493, hereby incorporated by reference in its entirety). Applicants have previously shown that mutations within the erythropoiesis binding sites that abolish erythropoiesis do not modify the tissue protective properties of EPO (Leist et al. Science (2004) 305:239, hereby incorporated by reference in its entirety).

One of ordinary skill in the art will recognize that fragments of varying lengths can form a tissue protective peptide, although the fragment is preferably less than 30 amino acids in length. Further, judicious selection of other molecules for inclusion, e.g., D-amino acids or polyethylene glycol, will also constitute a tissue protective peptides, but with enhanced biological half-lives.

A. Structural Motifs

Specifically, the following structural motifs have been identified that trigger the Tissue Protective Receptor complex:

(a) A Negative Charge Configuration ("Structural Motif A")

In this structural motif, the peptide possesses two negatively charged amino acids, which can be separated by up to 5 amino acids, flanked by hydrophobic amino acids. Structurally this can be represented as:

(a1) HNNH;
(a2) HNXNH;
(a3) HNXXNH;
(a4) HNXXXNH;
(a5) HNXXXXNH; or
(a6) HNXXXXXNH, where H represents hydrophobic amino acids (e.g., the moderately hydrophobic amino acids: glycine, proline, cysteine, tyrosine, and tryptophan, and preferably the highly hydrophobic amino acids: alanine, valine, isoleucine, methionine, leucine, phenylalanine), N represents a negatively charged amino acid such as glutamate or aspartate, and X represents any amino acid, although preferably a hydrophilic one. In certain embodiments, the flanking hydrophobic amino acids are the same. In other embodiments, the flanking amino acids are different.

A variation of this structural motif involves a peptide where one of the flanking hydrophobic amino acids has been replaced with a polar amino acid such as serine, threonine, asparagine, or glutamine.

As an alternative to peptide linkages establishing the mutual proximity of the two negative charges in a linear sequence, the necessary charge proximity may also be accomplished by a three dimensional structure as discussed herein above, (Section 5.1). For example, the negatively charged amino acids may be spatially immediately adjacent on the external surface of a helix, but will be separated by additional amino acids in the linear peptide sequence. For example, in helix A of EPO (corresponding to amino acids 10-28 of SEQ ID NO:1), E18 and E21 are adjacent on the three dimensional structure, but have two intervening amino acids between them in the linear peptide sequence. As an additional example, in helix B (peptide D, SEQ ID NO:30; corresponding to amino acids 58-82 of SEQ ID NO:1) E62 and E72 are separated by two amino acids (Q65 and L69) on the surface of the helix, but have 9 amino acids between them within the linear peptide. Peptides constructed from helix A or helix B are tissue protective (See Example 2 and Table 1, infra). In contrast, peptide B (NITTGCAEHCSLNE, SEQ ID NO:34) a peptide with dual negative charges (underlined) at the appropriate distance but lacking a flanking hydrophobic amino acid, is not tissue protective (See Example 2 and Table 1, infra).

(b) Negative/Positive Amino Acid Configuration ("Structural Motif B")

In this structural motif, the peptide has a positive amino acid next to a negative amino acid and both charged amino acids are flanked by single hydrophobic amino acids. Structurally this can be represented as:

(b1) HNPH; or
(b2) HPNH, where P represents positively charged amino acids such as arginine, lysine or histidine and N represents the negatively charged amino acids glutamate or aspartate. As with the first motif, the mutual proximity of the two opposite charges may be accomplished by three dimensional structure. For example, a positive and a negatively charged amino acid may be spatially adjacent on the surface of a helix, but will be separated by one or more amino acids in the linear peptide sequence. For example, in helix B (corresponding to amino acids 58-82 of SEQ ID NO:1) E72 and R76 are immediately adjacent to each other on the external surface of the helix and a peptide constructed from this helix is tissue protective (see Example 2 and Table 1).

In a variation of this particular motif, the negative and positive amino acids can be separated by a polar amino acid, e.g., (b3) HNLPH;
(b4) HPLNH, wherein L represents a polar amino acids such as serine, threonine, asparagine, or Glutamine. An example of this motif is peptide E (GCAEHCSLNENITVPDTKVN, SEQ ID NO:34), which is tissue protective (see Example 2 and Table 1).

Given that the core of the above structural motif is four amino acids in length, a peptide of this core structural motif may trigger the Tissue Protective Receptor. In certain embodiments the polypeptides of the invention comprise 1 structural motif. In alternate embodiments, the polypeptides of the invention comprise more than 1, more than 2, more than 3 or more than 4 of the structural motifs. In certain embodiments, wherein the polypeptide comprises at least two structural motifs, the motifs are the same. In alternate embodiments, wherein the polypeptide comprises at least two structural motifs, the motifs are different. Preferably, the multiple peptides of the present invention that one skilled in the art can generate are less than 30 amino acids in length.

One of ordinary skill in the art will recognize that it is the above noted structural motifs, as opposed to the actual amino acid sequence of EPO that is important to the current invention. Thus one of ordinary skill in the art would recognize that the isolated peptide may have less than 90%, less than 85%, less than 80%, less than 75%, less than 70%, less than 65%, less than 60%, less than 55%, less than 50%, less than 45%, less than 40%, less than 35%, less than 30%, or less than 20 percent sequence identity with any portion of the amino acid sequence of mature human erythropoietin ("EPO") set forth in SEQ ID NO:1, wherein said portion of EPO contains the same number of amino acid residues as said peptide.

Additionally, U.S. Pat. No. 5,700,909 to O'Brien et al., hereby incorporated by reference in its entirety) discloses a 17 amino acid peptide sequence of EPO (SEQ ID NO:11 of O'Brien) which induces biological activity in NS20Y, SK-N-MC, and PC12 cells including sprouting, differentiation, neuroprotection, and prevention of neuronal cell death. SEQ ID NO:11 of O'Brien (designed epopeptide AB), although prophetically disclosed, to have erythropoietic activity, in fact lacks such erythropoietic activity and was subsequently found to lack in vivo activity. When epopeptide AB was injected into the muscle of mice, the frequency of motor end plate sprouting in the adjacent muscles increased in a mariner similar to that induced by ciliary neurotrophic factor. These data are interpreted within the concept that neuronal (but not hematological) cells respond to a peptide sequence within EPO and that EPO may have separate domains for neurotrophic and hematotrophic activity (Campana et al., Int. J. Mol. Med. (1998) 1(1):235-241; J. S. O'Brien in U.S. Pat. No. 5,700,909, issued Dec. 23, 1997; J. S. O'Brien in U.S. Pat. No. 5,571,787, issued Nov. 5, 1996; J. S. O'Brien in U.S. Pat. No. 5,714,459, issued Feb. 3, 1998; and J. S. O'Brien and Y. Kashimoto in U.S. Pat. No. 5,696,080, issued Dec. 9, 1997). However, O'Brien did not appreciate the current structural motifs based upon the proximity of charged amino acids in the tertiary structure of the peptide.

C. Type 1 Cytokine Fragments.

Given the spatially compact charge configuration able to activate the tissue protective receptor, Applicants have discovered that certain fragments of type-1 cytokines are expected to cross react with the tissue protective receptor. This cytokine family includes, but is not limited to, interleukin (IL)-2, IL-3, IL-4, IL-5, IL-6, IL-7, IL-9, IL-10, IL-11, granulocyte macrophage-colony stimulating factor (GM-CSF), leptin, granulocyte colony stimulating factor (G-CSF), leukemia inhibiting factor (LIF), ciliary neurotrophic factor (CNTF), thrombopoietin (TPO), growth hormone, macrophage colony stimulating factor (M-CSF), erythropoietin (EPO) and prolactin.

Consideration of the secondary structure of EPO provides guidance for the preparation of a candidate tissue protective peptide via the spatial arrangement of amino acids derived from homologous amino acids located within homologous secondary structures within other type-1 cytokine receptor ligands: e.g., GM-CSF and IL-3 (Kalman, 2000, Neuroimmunomod. 8:132-141, hereby incorporated by reference in its entirety), among others, have been shown to possess potent neurotrophic and neuroprotective activities, due in large part, the Applicants believe, by stimulating a tissue protective receptor. For example, considering helix B of these type I cytokines: Homologous amino acids in thrombopoietin (TPO; Protein Data Bank (PDB) accession 1V7M) comprise D62, G65, T68, L69, E72, A76 and Q80, where these amino acids are spatially adjacent to one another in a linear arrangement; homologous amino acids in leukemia inhibitory factor (LIF; PDB accession 1EMR) comprise E61, R64, Y68, S72, N75, and D79; homologous amino acids in ciliary neurotrophic factor (CNTF; PDB accession 1 CNT) comprise E71, E75. These all are examples of Motif A described above (section 5.1.1), wherein the underlined amino acids are negatively charged.

Examples of peptides derived from the Type-1 cytokines that exemplify the structural Motif B described herein above (section 5.1.1) include, but are not limited to, GM-CSF helix A fragment, WEHVNAIQEARRLL (SEQ ID NO:35); TPO helix A fragment, LSKLLRDSHVLH (SEQ ID NO:36); TPO helix B fragment: E56, K59; CNTF helix A fragment, KIRSDLTALTESYVKH (SEQ ID NO:37); CNTF helix B fragment: R89, E92. LIF helix B fragment, GTEKAKLVELYRIVVYL (SEQ ID NO:38); and interleukin 3 (IL-3) helix A fragment SIMIDEIIHHLKRPPNPL (SEQ ID NO:39).

These aforementioned amino acids are merely exemplary from some members of the cytokine superfamily that signal through Type 1 cytokine receptors, and homologous regions on other members of the cytokine superfamily will be readily identified by the skilled artisan.

5.1.2 Chimeras

"Chimeric" tissue protective peptides—linear amino acid sequences that incorporate non-linear structural elements of the externally-facing amino acids of EPO molecule exhibit the above-noted structural motifs—are also contemplated by the current invention. Chimeric tissue protective peptides of the current invention may consist of combining structural elements of separate amino acid sequences into a single peptide. In other words, a chimeric tissue protective peptide may be comprised of amino acid sequences derived from non-linear but adjacent structural elements such as a fragment derived from amino acid sequences 110-115, 133-136, and 160-165, of SEQ ID NO:1 which would allow structural elements of the C terminal portion of helix C and N-terminal portion of loop C-D, the β-pleated sheet in loop C-D, and the C-terminal portion of EPO to be contained in a single peptide. Additionally, chimeric tissue protective peptides may be used to select out the important features of a particular structure, for example the externally-facing amino acids of a particular tertiary structure. Thus, a chimeric tissue protective peptide may consist of a fragment comprised of helix B amino acids 58, 62, 65, 69, 72, 76, 79, 80, 83, 84, and 85 (e.g., peptide G, QEQLERALNSS, SEQ ID NO:40) or, in other words, all of the exterior-presenting amino acids of helix B of EPO. This peptide is shown to be tissue protective in Example 2, infra (see Table 1).

Furthermore, the potency of the current tissue protective peptides may be increased by attaching an amphipathic peptide helix. Amphipathic peptide helices are well known in the art, e.g. from peptides that signal through the Class B G-protein coupled receptors (e.g., Segrest et al., 1990, Proteins 8:103, hereby incorporated by reference in its entirety), serving to localize the peptide ligand to the cell membrane. Examples of such helices include, but are not limited to, the highly hydrophobic regions from: calcitonin (ALSILVLLQAGS, SEQ ID NO:48); corticotropin releasing hormone (VALLPCPPCRA, SEQ ID NO:49); beta endorphin (NAIIKNAYKKG, SEQ ID NO:50); glucagon (GSWQRSLQDTE, SEQ ID NO:51); secretin (GGSAARPAPP, SEQ ID NO:52); vasointestinal polypeptide (NALAENDTPYY, SEQ ID NO:53); neuropeptide Y (GALAEAYPSKP, SEQ ID NO:54); gonadotropin releasing hormone (GCSSQHWSYGL, SEQ ID NO:55); parathyroid hormone (VMIVMLAICFL, SEQ ID NO:56); pancreatic polypeptide (LRRYINMLTRP, SEQ ID NO:28); and calcitonin gene related peptide (LALSILVLYQA, SEQ ID NO:57) (disclosed in Grace et al., 2004, PNAS 101:12836, hereby incorporated by reference in its entirety). For example, a chimeric peptide made from a peptide with the surface charge motif of helix B of EPO (QEQLERALNSS, SEQ ID NO:40) joined at the carboxy terminus to the ampipathic helix of pancreatic polypeptide (LRRYINMLTRP, SEQ ID NO:28) for a chimeric peptide. Further modifications may be made to the carboxy terminus of the amphipathic helix without affecting its tissue protective properties. Thus, a further example, replacing the terminal proline of the above chimeric peptide with the sequence TR (QEQLERALNSSLRRYINMLTRTR, SEQ ID NO:41) generates a molecule with potent tissue protective activity as demonstrated in the sciatic nerve assay (see, FIG. 1).

Additionally, instead of the above-noted helices, other tertiary structures can be attached to the tissue protective peptides. For example, the helix B exterior-presenting amino acids can be linked to the beta pleated sheet (CSLNENI, SEQ ID NO:42) found within the AB loop of EPO to form a chimeric peptide having the sequence CSLNENIQEQLERALNSS (SEQ ID NO:43), which is tissue protective (see Example 2 and Table 1). Additionally, the presenting amino acids of the terminal portion of helix C (ALGKA, SEQ ID NO:44, corresponding to amino acids 111,112,113,116, and 118 of SEQ ID NO:1) may be combined with all or part of loop CD-partial (LGAQKEAISPPDAASAAPLRTI, SEQ ID NO:45, corresponding to amino acids 112-133 of SEQ ID NO:1). Preferably, a linking arm will be present between the fused peptides to provide for flexibility so that the joined peptides can assume the proper structural orientation to bind with the tissue protective receptor complex. Such fusion peptides may have a synergistic effect, obtaining a greater tissue protective effect jointly as opposed to individually possibly through enhanced binding with the tissue protective receptor complex or increased biological half life.

One of ordinary skill in the art will recognize the benefit of combining various desired structural elements in to a single peptide for maximizing the tissue protective effects of such compounds. Such chimeras may comprise amino acids peptides, and non-amino acid elements, such as linkers or bridging atoms or moieties.

5.1.3 Fusion Peptides

The present invention further contemplates that two or more of the above noted tissue protective peptides, fragment derived or chimera, may be linked to a related or unrelated protein such as erythropoietin, albumin, etc.

5.1.4 Manufacture of Tissue Protective Peptides

Tissue protective peptides of the current invention may be made using recombinant or synthetic techniques well known in the art. In particular, solid phase protein synthesis is well suited to the relatively short length of the tissue protective peptides and may provide greater yields with more consistent results. Additionally, the solid phase protein synthesis may provide additional flexibility regarding the manufacture of the tissue protective peptides. For example, desired chemical modifications may be incorporated into the tissue protective peptide at the synthesis stage: homocitrulline could be used in the synthesis of the peptide as opposed to lysine, thereby obviating the need to carbamylate the peptide following synthesis.

Synthesis

In solid-phase synthesis of a peptide an amino acid with both α-amino group and side chain protection is immobilized on a resin. See e.g. Nilsson, B., Soellner, M., and Raines, R. Chemical Synthesis of Proteins, *Annu. Rev. Biomol. Struct.* 2005. 34:91-118; Meldal M. 1997. Properties of solid supports. *Methods Enzymol.* 289:83-104 and Songster M F, Barany G. 1997. Handles for solid-phase peptide synthesis. *Methods Enzymol.* 289:126-74. Typically, two types of α-amino-protecting groups are used: an acid-sensitive tert-butoxycarbonyl (Boc) group or a base-sensitive 9-fluorenyl-methyloxycarbonyl (Fmoc) group. Wellings D A, Atherton E. 1997. Standard Fmoc protocols. *Methods Enzymol.* 289:44-67. After the quick and complete removal of these α-amino-protecting groups another protected amino acid with an activated carboxyl group can then be coupled to the unprotected resin-bound amine. By using an excess of activated soluble amino acid, the coupling reactions are forced to completion. The cycle of deprotection and coupling is repeated to complete the sequence. With side chain deprotection and cleavage, the resin yields the desired peptide. Guy C A, Fields G B. 1997. Trifluoroacetic acid cleavage and deprotection of resin-bound peptides following synthesis by Fmoc chemistry. *Methods Enzymol.* 289:67-83, and Stewart J M. 1997. Cleavage methods following Boc-based solid-phase peptide synthesis. *Methods Enzymol.* 289:29-44. Additional methods for performing solid phase protein synthesis are disclosed in Bang, D. & Kent, S. 2004. A One-Pot Total Synthesis of Crambin. *Angew. Chem. Int. Ed.* 43:2534-2538; Bang, D., Chopra, N., & Kent, S. 2004. Total Chemical Synthesis of Crambin. *J. Am. Chem. Soc.* 126:1377-1383; Dawson, P. et al. 1994. Synthesis of Proteins by Native Chemical Ligation. *Science.* 266:776-779; Kochendoerfer et al. 2003. Design and Chemical Synthesis of a Homogenous Polymer-Modified Erythropoiesis Protein. *Science.* 299: 884-887. (Each reference recited in this paragraph is hereby incorporated by reference in its entirety.)

If necessary, smaller peptides derived from solid phase peptide synthesis may be combined through peptide ligations such as native chemical ligation. In this process, the thiolate of an N-terminal cysteine residue of one peptide attacks the C-terminal thioester of a second peptide to affect transthioesterification. An amide linkage forms after rapid S→N acyl transfer. See Dawson, P. et al. 1994. Synthesis of Proteins by Native Chemical Ligation. *Science.* 266:776-779, which is hereby incorporated by reference in its entirety.

Further, one of ordinary skill in the art would recognize, that the tissue protective peptides of the current invention may encompass peptidomimetics, peptides including both naturally occurring and non-naturally occurring amino acids, such as peptoids. Peptoids are oligomers of N-substituted glycines, glycoholic acid, thiopronine, sarcosine, and thiorphan. These structures tend to have a general structure of $(-(C=O)-CH_2-NR-)_n$ with the R group acting as the side chain. Such peptoids can be synthesized using solid phase synthesis in accordance with the protocols of Simon et al., Peptoids: A molecular approach to drug discovery, *Proc. Natl. Acad. Sci. USA,* 89:9367-9371 (1992) and Li et al., Photolithographic Synthesis of Peptoids, *J. AM. CHEM. SOC.* 2004, 126, 4088-4089, each of which is hereby incorporated by reference in its entirety. Additionally, the current invention contemplates the use of peptidemimetics or peptide mimetics, non-peptide drugs with properties analogous to those of the template peptide. (Fauchere, J. (1986) Adv. Drug Res. 15.29; Veber and Friedinger (1985) TINS p. 32; and Evans et al. (1987) J. Med. Chem. 30:1229, which are incorporated by reference). Synthesis of various types of peptidomimetics has been reviewed for example in: Methods of Organic Chemistry (Houben-Weyl), Sythesis of Peptides and Peptidomimetics—Workbench Edition Volume E22c (Editor-in-Chief Goodman M.) 2004 (George Theme Verlag Stuttgart, New York, hereby incorporated by reference in its entirety).

Recombinant Techniques

A variety of host-expression vector systems may be utilized to produce the tissue protective peptides of the invention. Such host-expression systems represent vehicles by which the tissue protective peptide of interest may be produced and subsequently purified, but also represent cells that may, when transformed or transfected with the appropriate nucleotide coding sequences, exhibit the modified erythropoietin gene product in situ. These include but are not limited to, bacteria, insect, plant, mammalian, including human host systems, such as, but not limited to, insect cell systems infected with recombinant virus expression vectors (e.g., baculovirus) containing the tissue protective peptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing erythropoietin-related molecule coding sequences; or mammalian cell systems, including human cell systems, e.g., HT1080, COS, CHO, BHK, 293, 3T3, harboring recombinant expression constructs containing promoters derived from the genome of mammalian cells, e.g., metallothionein promoter, or from mammalian viruses, e.g., the adenovirus late promoter; the vaccinia virus 7.5K promoter.

In addition, a host cell strain may be chosen that modulates the expression of the inserted sequences, or modifies and processes the gene product in the specific fashion desired. Such modifications and processing of protein products may be important for the function of the protein. As known to those of ordinary skill in the art, different host cells have specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant peptides, stable expression is preferred. For example, cell lines that stably express the recombinant tissue protective cytokine-related molecule gene product may be engineered. Rather than using expression vectors that contain viral origins of replication, host cells can be transformed with DNA controlled by appropriate expression control elements, e.g., promoter, enhancer, sequences, transcription terminators, polyadenylation sites, and the like, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the tissue-protective product. Such engineered cell lines may be particularly useful in screening and evaluation of compounds that affect the endogenous activity of the EPO-related molecule gene product.

Further Modifications

Additional modifications can be made to the tissue protective peptides. For example, the peptide may be synthesized with one or more (D)-amino acids. The choice of including an (L)- or (D)-amino acid into a peptide of the present invention depends, in part, upon the desired characteristics of the peptide. For example, the incorporation of one or more (D)-amino acids can confer increasing stability on the peptide in vitro or in vivo. The incorporation of one or more (D)-amino acids can also increase or decrease the binding activity of the peptide as determined, for example, using the bioassays described herein, or other methods well known in the art.

Replacement of all or part of a sequence of (L)-amino acids by the respective sequence of entatiomeric (D)-amino acids renders an optically isomeric structure in the respective part of the polypeptide chain. Inversion of the sequence of all or part of a sequence of (L)-amino acids renders retro-analogues of the peptide. Combination of the enantiomeric (L to D, or D to L) replacement and inversion of the sequence renders retro-inverso-analogues of the peptide. It is known to those skilled in the art that enantiomeric peptides, their retro-analogues, and their retro-inverso-analogues maintain significant topological relationship to the parent peptide, and especially high degree of resemblance is often obtained for the parent and its retro-inverso-analogues. This relationship and resemblance can be reflected in biochemical properties of the peptides, especially high degrees of binding of the respective peptides and analogs to a receptor protein. The synthesis of the properties of retro-inverso anologues of peptides have been discussed for example in Methods of Organic Chemistry (Houben-Weyl), Synthesis of Peptides and Peptidomimetics—Workbench Edition Volume E22c (Editor-in-chief Goodman M.) 2004 (George Thieme Verlag Stuttgart, New York), and in references cited therein, all of which are hereby incorporated by reference herein in their entireties.

Amino acid "modification" refers to the alteration of a naturally occurring amino acid to produce a non-naturally occurring amino acid. Derivatives of the peptides of the present invention with non-naturally occurring amino acids can be created by chemical synthesis or by site specific incorporation of unnatural amino acids into polypeptides during biosynthesis, as described in Christopher J. Noren, Spencer J. Anthony-Cahill, Michael C. Griffith, Peter G. Schultz, 1989 Science, 244:182-188, hereby incorporated by reference herein in its entirety.

Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), but have one or more peptide linkages optionally replaced by a linkage selected from the group consisting of —CH$_2$—NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p 267 (1983); Spatola, A. F., Vega Data (March 1983), Vol. 1. Issue 3, "Peptide Backbone Modifications" (general review); Morely, J. S., Trends Pharma Sci (1980) pp. 463-468 (general review); Hudson, D. et al., (1979) Int J Pept Prot Re 14: 177-185 (—CH$_2$—NH—, —CH$_2$—CH$_2$—); Spatola, A. F. et al., (1986) Life Sci 38:1243-1249 (—CH$_2$—S); Hann, M. M., (1982) J Chem Soc Perkin Trans 1307-314 (—CH=CH—, cis and trans); Almquist, R. G. et al., (1980) J Med Chem 23: 1392 (—COCH$_2$—); Jennings-White, C et al., (1982) Tetrahedron Lett 23:2533 (—COCH$_2$—); Szelke, M et al., European Appln. EP 45665 (1982) CA: 97: 39405 (1982) (—CH(OH)CH$_2$—); Holladay, M. W. et al., (1983) Tetrahedron Lett 24:4401-4404 (—C(OH)CH$_2$—); and Hruby, V. J., (1982) Life Sci 31:189-199 (—Cl$_2$—S—); each of which is incorporated herein by reference.

In another embodiment, a particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

A variety of designs for peptide mimetics are possible. For example, cyclic peptides, in which the necessary conformation is stabilized by non-peptides, are specifically contemplated, U.S. Pat. No. 5,192,746 to Lobl, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred et al., J. Med. Chem. 37:3882 (1994), hereby incorporated by reference herein in its entirety) describe non-peptide antagonists that mimic the peptide sequence. Likewise, Ku et al., J. Med. Chem. 38:9 (1995) (hereby incorporated by reference herein in its entirety) further elucidates the synthesis of a series of such compounds.

Further modifications following synthesis may be implemented. For example, the tissue protective peptides may be further chemically modified, i.e. carbamylated, acetylated, succinylated, etc., in accordance with U.S. patent application Ser. No. 10/188,905, which published as 20030072737-A1 on Apr. 17, 2003 and discloses chemically modified EPO, and in accordance with U.S. patent application Ser. No. 10/612, 665, filed Jul. 1, 2003, and U.S. patent application Ser. No. 09/753,132, filed Dec. 29, 2000, which are incorporated by reference herein in their entirety.

Additionally, the tissue protective peptides may consist of recombinant tissue protective peptides—muteins. The disclosed mutations may include substitutions, deletions, including internal deletions, additions, including additions yielding fusion proteins, or conservative substitutions of amino acid residues within and/or adjacent to the amino acid sequence, but that result in a "silent" change, and non-conservative amino acid changes and larger insertions and deletions, as previously disclosed in PCT/US03/20964 entitled Recombinant Tissue Protective Cytokines and Encoding Nucleic Acids Thereof for Protection, Restoration, and Enhancement of Responsive Cells, Tissues, and Organs (which is incorporated by reference herein in its entirety)

Either conservative or non-conservative amino acid substitutions can be made at one or more amino acid residues. Both conservative and non-conservative substitutions can be made. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar (hydrophobic)=cysteine, alanine, valine, leucine, isoleucine, proline, phenylalanine, methionine, tryptophan, glycine, tyrosine; and (4) uncharged polar=asparagine, glutamine, serine, threonine. Non-polar may be subdivided into: strongly hydrophobic=alanine, valine, leucine, isoleucine, methionine, phenylalanine and moderately hydrophobic=glycine, proline, cysteine, tyrosine, tryptophan. In alternative fashion, the amino acid repertoire can be grouped as (1) acidic=aspartate, glutamate; (2) basic=lysine, arginine, histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (See, for example, Biochemistry, 4th ed., Ed. by L. Stryer, WH Freeman and Co., 1995, which is incorporated by reference herein in its entirety).

Alternatively, mutations can be introduced randomly along all or part of the coding sequence of a tissue protective peptide, such as by saturation mutagenesis, and the resultant mutants can be screened for biological activity to identify mutants that retain activity. Following mutagenesis, the encoded peptide can be expressed recombinantly and the activity of the recombinant tissue protective peptide can be determined.

In another embodiment, the tissue protective peptide may be further modified through the additions of polymers (such as polyethylene glycol), sugars, or additional proteins (such as a fusion construct) in an effort to extend the half-life of the tissue protective peptide or enhance the peptide's tissue protective effects. Examples of such modifications are disclosed within WO/04022577 A3 and WO/05025606 A1, which are incorporated herein by reference.

5.2 Assays for Testing Tissue Protective Peptides

5.2.1 Biological Screens or Assays

Tissue protective peptides in accordance with the present invention may be tested for tissue protective activity, e.g., protecting cells, tissues or organs. Protective activities may be further tested using in vitro and in vivo assays. In vitro tests that are indicative of tissue protective activity include, for example, cell proliferation assays, cell differentiation assays, or detecting the presence of proteins or nucleic acids upregulated by tissue protective receptor complex, e.g. tissue protective cytokine receptor complex, activity, e.g., nucleolin, neuroglobin, cytoglobin, or frataxin. Neuroglobin, for example, may be involved in facilitating the transport or the short-term storage of oxygen. Therefore, oxygen transport or storage assays may be used as an assay to identify or screen for compounds which modulate tissue protective activity.

Neuroglobin is expressed in cells and tissues of the central nervous system in response to hypoxia or ischemia and may provide protection from injury (S et al. 2001, PNAS 98:15306-15311; Schmid et al., 2003, J. Biol. Chem. 276: 1932-1935, each of which is incorporated by reference herein in its entirety). Cytoglobin may play a similar role in protection, but is expressed in a variety of tissues at varying levels (Pesce et al., 2002, EMBO 3:1146-1151, which is incorporated by reference herein in its entirety). In one embodiment of the invention, the levels of an upregulated protein in a cell may be measured before and after contacting the tissue protective peptide to a cell. In certain embodiments, the presence of an upregulated protein associated with tissue protective activity in a cell, may be used to confirm the tissue protective activities of a peptide.

Nucleolin may protect cells from damage. It plays numerous roles in cells including modulation of transcription processes, sequence specific RNA-binding protein, cytokinesis, nucleogensis, signal transduction, apoptosis induced by T-cells, chromatin remodelling, or replication. It can also function as a cell surface receptor DNA/RNA helicase, DNA-dependent ATPase, protein shuttle, transcription factor component, or transcriptional repressor (Srivastava and Pollard, 1999, FASEB J., 13:1911-1922; and Ginisty et al., 1999, J. Cell Sci., 112:761-772, each of which is incorporated by reference herein in its entirety).

Frataxin is a protein involved with mitochondrial iron metabolism and has previously been shown to be strongly up-regulated by EPO both in vivo and in vitro (Sturm et al. (2005) Eur J Clin Invest 35: 711, which is incorporated by reference herein in its entirety)

Expression of an upregulated protein may be detected by detecting mRNA levels corresponding to the protein in a cell. The mRNA can be hybridized to a probe that specifically binds a nucleic acid encoding the upregulated protein. Hybridization may consist of, for example, Northern blot, Southern blot, array hybridization, affinity chromatography, or in situ hybridization.

Tissue protective activity of the polypeptide of the invention can also be detected using in vitro neuroprotection assays. For example, primary neuronal cultures may be prepared from new born rat hippocampi by trypsinization, and cultured as by any method known in the art and/or described herein e.g. in MEM-II growth medium (Invitrogen), 20 mM D-glucose, 2 mM L-glutamine, 10% Nu-serum (bovine; Becton Dickinson, Franklin Lakes, N.J.), 2% B27 supplement (Invitrogen), 26.2 mM $NaHCO_3$, 100 U/ml penicillin, and 1 mg/ml streptavidin (see, e.g., Leist et al., 2004, Science 305: 239-242, hereby incorporated by reference in its entirety). One day after seeding, 1 μM cytosinearabino-furanoside is added. Thirteen day old cultures are then preincubated with increasing doses of EPO or CEPO (3-3000 pM) for 24 h. On day 14, the medium is removed and the cultures challenged with 300 μM NMDA in PBS at RT. After 5 min, pre-conditioned medium is returned to the cultures which are then returned to the incubator for 24 h. The cells are fixed in paraformaldehyde, stained by Hoechst 33342 (Molecular Probes, Eugene, Oreg.) and condensed apoptotic nuclei may be counted. NGF (50 ng/ml) and MK801 (1 μM) are included as positive controls.

Animal model systems can be used to demonstrate the tissue protective activity of a compound or to demonstrate the safety and efficacy of the compounds identified by the screening methods of the invention described above. The compounds identified in the assays can then be tested for biological activity using animal models for a type of tissue damage, disease, condition, or syndrome of interest. These include animals engineered to contain the tissue protective receptor complex coupled to a functional readout system, such as a transgenic mouse.

Animal models that can be used to test the efficacy of the cell or tissue protective activity of an identified compound include, for example, protection against the onset of acute experimental allergic encephalomyelitis (EAE; see, Example 12) in Lewis rats, restoration or protection from diminished cognitive function in mice after receiving brain trauma, cerebral ischemia ("stroke"; Example 5) or seizures stimulated by excitotoxins (Brines et al., 2000, PNAS, 97:10295-10672, which is incorporated by reference herein in its entirety), protection from induced retinal ischemia (Rosenbaum et al., 1997, Vis. Res. 37:3443-51 which is incorporated by reference herein in its entirety), protection from injury to the sciatic nerve (see, Example 2), and protection from ischemia-reperfusion injury to the heart (in vitro cardiomyocyte studies and in vivo ischemia-reperfusion injury, see, e.g., Calvillo et al., 2003, PNAS 100:4802-4806 and Fiordaliso et al., 2005, PNAS 102:2046-2051, each of which is hereby incorporated by reference in its entirety). Such assays are described in further detail in Grasso et al. (2004) Med Sci Monit 10: BR1-3 or PCT publication no. WO02/053580, each of which is incorporated by reference herein in its entirety. The in vivo methods described therein are directed towards administration of EPO, however, tissue protective proteins administered in place of EPO have been identified to also exhibit similar biologic activity, e.g., Leist et al. (2004) Science 305: 239-242, which is incorporated by reference herein in its entirety. Peptides may be substituted for testing as well. Other assays for determining tissue protective activity of a peptide are well known to those of skill in the art.

5.2.2 Cell Binding Assays

Alternatively, cell binding assays can be for evaluation of the polypeptides of the invention. For example, the tissue protective peptide of interest can be bound to a biological marker such as a fluorescent or radiolabed marker for ease of detection and tested for binding to transfected BaF3 cells expressing EPOR and/or receptor. In a 96 well plate, eight 1:2 serial dilutions of the tissue protective peptide of interest in growth medium (RPMI 1640, 10% fetal bovine serum, 1 mM sodium pyruvate, 2 mM L-glutamine) are plated, such that the final volume in each well is about 100 µl. The BaF3 parental line and BaF3 cells transfected with EPOR and/or $\beta_c$ receptor can be washed three times in growth media (see above), pellets resuspended in growth medium, and cells counted and diluted in growth media to 5,000 cells/100 µl. 100 µl of diluted cells are then added to each peptide dilution. The assay plate is then incubated in a 37° C. incubator for three to four days. The plate/cells are then washed and the plate is read on a fluorescent plate reader or by other suitable method to detect the level of biomarker associated with the biological activity of the tissue protective peptide of interest.

Similarly, a competitive assay can be utilized to determine if a tissue protective peptide is tissue protective. In the competitive assay, a compound known to be tissue protective including, but not limited to, tissue protective cytokines such as those disclosed in U.S. patent application Ser. Nos. 10/188,905 and 10/185,841 (each of which is incorporated by reference herein in its entirety), can be attached to a suitable bio marker.

In a 96 well plate eight 1:2 serial dilutions of a known tissue protective compound/biomarker in suitable growth medium, and the same dilution series of the known tissue protective compound/biomarker and an excess of the tissue protective peptide of interest are plated. The final volume of each dilution should be about 100 µl. Once again, the BaF3 cells are seeded into the plates as disclosed supra and allowed to incubate. After an appropriate amount of time, the cells are washed and the plate is read on a fluorescent plate reader or by any other suitable method known in the art to detect the biomarker. If the readout of the plates and/or wells containing the known tissue protective compound/biomarker and tissue protective peptide of interest is less than the readout of the plates containing only the known tissue protective compound/biomarker then the tissue protective peptide of interest is tissue protective.

5.2.3 Cytokine and Cell Proliferation/Differentiation Activity

Many protein factors discovered to date, including all known cytokines, have exhibited activity in one or more factor-dependent cell proliferation assays, and hence these assays serve as a convenient confirmation of cytokine activity. The activity of a tissue protective peptide can be evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK. These cells are cultured in the presence or absence of a tissue protective peptide, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, 1983, J. Immunol. Meth. 65:55-63, which is incorporated by reference herein in its entirety).

5.2.4 Other Assays

If a tissue protective peptide exhibits a tissue protective activity, one of ordinary skill in the art would recognize that it would be beneficial to verify the result using one of the neuroprotective and tissue protective assays known to those skilled in the art, such as, but not limited to, P-19 and PC-12 cell assays. Additionally, various in vivo models such as animal models related to spinal cord injury, ischemic stroke, peripheral nerve damage, heart, eyes, kidneys, etc. would be helpful in further characterizing the tissue protective peptide. Suitable in vitro and in vivo assays are disclosed in U.S. patent application Ser. Nos. 10/188,905 and 10/185,841, each of which is incorporated by reference herein in its entirety.

5.3 Therapeutic Use

One of ordinary skill in the art would recognize that the tissue protective peptides of the current invention are useful as therapeutics for treatment or prevention of various diseases, disorders, and conditions. One skilled in the art would also recognize that such peptides can be used to achieve modulation of a tissue protective receptor complex, e.g., tissue protective cytokine complex. Both in vitro and in vivo techniques that can be used for assessing the therapeutic indications of, for example, the compounds identified by the inventive assays disclosed above are disclosed in PCT Application No. PCT/US01/49479, U.S. patent application Ser. Nos. 10/188,905 and 10/185,841, incorporated herein by reference.

The aforementioned tissue protective peptides of the invention may be useful generally for the prevention, therapeutic treatment, or prophylactic treatment of human diseases or disorders of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, connective tissue diseases, gastrointestinal diseases and endocrine and metabolic abnormalities. Examples of use include, but are not limited to, protection against and repair of injury resulting from trauma and resulting inflammation to the brain (ischemic stroke, blunt trauma, subarachnoid hemorrhage), spinal cord (ischemia, blunt force trauma), peripheral nerves (sciatic nerve injury, diabetic neuropathy, carpal tunnel syndrome), retinal (macular edema, diabetic retinopathy, glaucoma), and heart (myocardial infarct, chronic heart failure). In particular, such diseases, disorders, and conditions include hypoxic conditions, which adversely affect responsive tissues, such as excitable tissues in the central nervous system tissue, peripheral nervous system tissue, or cardiac tissue or retinal tissue such as, for example, brain, heart, or retina/eye. Therefore, the tissue protective peptides of the invention can be used to treat or prevent damage to responsive tissue resulting from hypoxic conditions in a variety of conditions and circumstances. Non-limiting examples of such conditions and circumstances are provided in the table herein below.

The tissue protective polypeptides are also of interest in the modulation of stem cell activity. It has been established that cytokines exhibiting tissue protective activity, e.g. EPO, are able to mobilize stem cells, stimulating the migration to regions of injury and aiding the repair process, e.g. in a regenerative role. For example, in experimental stroke, EPO mediates the migration of neuroblasts into a region of ischemic injury to regenerate neurons during the period of recovery (Tsai et al, J. Neurosci (2006) 26:1269-74, incorporated herein by reference in its entirety). As another example, EPO and CEPO mobilize endothelial progenitor cells from the bone marrow into the circulation. These cells then home to distance regions and are involved in the formation of new blood vessels (for effect of EPO, see, Bahlmann et al, 2003, Kidney Int. 64:1648-1652, incorporated by reference herein in its entirety). While not wishing to be bound to any, particular theory, the isolated polypeptides disclosed herein are believed to have a similar effect on the migration of stem cells.

In the example of the protection of neuronal tissue pathologies treatable and preventable using tissue protective peptides of the invention, such pathologies include those which result from reduced oxygenation of neuronal tissues. Any condition which reduces the availability of oxygen to neuronal tissue, resulting in stress, damage, and finally, neuronal cell death, can be treated using tissue protective peptides of the present invention. Generally referred to as hypoxia and/or ischemia, these conditions arise from or include, but are not limited to, stroke, vascular occlusion, prenatal or postnatal oxygen deprivation, suffocation, choking, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmia, nitrogen narcosis, and neurological deficits caused by heart-lung bypass procedures.

In one embodiment, for example, the tissue protective peptides of the present invention identified using the inventive assay could be administered alone or as part of a composition to prevent injury or tissue damage resulting from risk of injury or tissue damage prior to, during, or subsequent to a surgical procedure or a medical procedure. For example, surgical procedures may include tumor resection or aneurysm repair and medical procedures may include labor or delivery. Other pathologies caused by or resulting from hypoglycemia which are treatable using tissue protective peptides of the present invention include insulin overdose, also referred to as iatrogenic hyperinsulinemia, insulinoma, growth hormone deficiency, hypocortisolism, drug overdose, and certain tumors.

Other pathologies resulting from excitable neuronal tissue damage include seizure disorders, such as epilepsy, convulsions, or chronic seizure disorders. Other treatable conditions and diseases include, but are not limited to, diseases such as stroke, multiple sclerosis, hypotension, cardiac arrest, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, optic nerve damage resulting from glaucoma, and neuronal loss.

The specific tissue protective peptides of the present invention may be used to treat or prevent inflammation resulting from disease conditions or various traumas, such as physically or chemically induced inflammation. The tissue protective peptides are also contemplated for the treatment and prevention of inflammatory conditions in one or more organs or tissues including, but not limited to, the brain, spinal cord, connective tissue, heart, lung, kidney and urinary tract, pancreas, eyes and prostate. Non-limiting examples of such trauma include tendonitis, angitis, chronic bronchitis, pancreatitis, osteomyelitis, rheumatoid arthritis, glomerulonephritis, optic neuritis, temporal arteritis, encephalitis, meningitis, transverse myelitis, dermatomyositis, polymyositis, necrotizing fascilitis, hepatitis, and necrotizing enterocolitis. Further the tissue protective cytokines may used to treat or prevent inflammation resulting from ischemic and non-ischemic conditions including, but not limited to, allergies, rheumatic diseases, sports related inuries, infections including viral, fungal, and bacterial. The inflammation may be acute or chronic. Further applications in the field of inflammation are noted within PCT/US2004/031789 filed Sep. 29, 2004 and published as WO 2005/032467, hereby incorporated by reference in its entirety.

The specific tissue protective peptides of the present invention may be used to treat central nervous and peripheral nervous system diseases resulting from demyelination or impairment of the mylin sheath. These diseases are defined as mainly involving inflammatory myelin sheath lesions of unknown origin, with the exception of myelination deficiency diseases, such as leukodystrophy, and diseases due to obvious causes. Multiple sclerosis (MS) is a typical disease among demyelinating diseases, and pathologically, it is characterized by changes, mainly, inflammatory demyelination, and gliosis. Since its etiology is unknown, its diagnosis is made based on its clinical features, i.e., spatial multiplicity and multiplicity over time of central nervous system lesions. Furthermore, acute disseminated encephalomyelitis (ADEM), inflammatory diffuse sclerosis, acute and subacute necrotizing hemorrhagic encephalomyelitis, and transverse myelitis are included in demyelinating diseases. Also, peripheral nervous tissues rely upon Schwann's cells to maintain the myelin sheath, if these cells are impaired, peripheral demyelinating disease is caused.

The tissue protective peptides of the present invention may be used to treat or prevent conditions of, and damage to the heart including any chronic or acute pathological event involving the heart and/or associated tissue (e.g., the pericardium, aorta and other associated blood vessels), including ischemia-reperfusion injury; congestive heart failure; cardiac arrest; myocardial infarction; atherosclerosis, mitral valve leakage, atrial flutter, cardiotoxicity caused by compounds such as drugs (e.g., doxorubicin, herceptin, thioridazine and cisapride); cardiac damage due to parasitic infection (bacteria, fungi, rickettsiae, and viruses, e.g., syphilis, chronic *Trypanosoma* cruzi infection); fulminant cardiac amyloidosis; heart surgery; heart transplantation; angioplasty, laparoscopic surgery, traumatic cardiac injury (e.g., penetrating or blunt cardiac injury, and aortic valve rupture), surgical repair of a thoracic aortic aneurysm; a suprarenal aortic aneurysm; cardiogenic shock due to myocardial infarction or cardiac failure; neurogenic shock and anaphylaxis. The tissue protective peptides of the current invention may also be used to treat those individuals at risk for heart disease such as cardiac failure (i.e., where the heart is not able to pump blood at a rate required by the metabolizing tissues, or when the heart can do so only with an elevated filling pressure). Such at risk patients would include patients having or being at risk of having cardiac infarction, coronary artery disease, myocarditis, chemotherapy, cardiomyopathy, hypertension, valvular heart diseases (most often mitral insufficiency and aortic stenosis) and toxin-induced cardiomyopathy (e.g. ethanol, cocaine, etc.) and the like.

The tissue protective peptides of the present invention may be used to treat or prevent conditions of, and damage to, the eyes, e.g., retinal tissue. Such disorders include, but are not limited to retinal ischemia, macular degeneration, retinal detachment, retinitis pigmentosa, arteriosclerotic retinopathy, hypertensive retinopathy, retinal artery blockage, retinal vein blockage, hypotension, and diabetic retinopathy.

In another embodiment, the tissue protective peptides of the present invention and principles of the invention may be used to prevent or treat injury resulting from radiation damage to responsive tissue. A further utility of the tissue protective peptides of the present invention is in the treatment of poisoning, such as neurotoxin poisoning (e.g., domoic acid shellfish poisoning), toxins (ethanol, cocaine, etc.), as the result of chemotherapeutic agents of radiation exposure; neurolathyrism; Guam disease; amyotrophic lateral sclerosis; and Parkinson's disease.

As mentioned above, the present invention is also directed to tissue protective peptides of the present invention for use in enhancing tissue function in responsive cells, tisses and organs in a mammal by peripheral administration of a tissue protective cytokine as described above. Various diseases and conditions are amenable to treatment using this method. For example this method is useful for enhancing function in excitable tissues resulting in an increase in cognitive function even in the absence of any condition or disease. Further, the tissue protective cytokines are useful for improving the quality of wound healing, reducing the time required to heal, improving the quality of the healed tissues and reducing the incidence of adhesions resulting from the wound. See PCT/US2004/031789 filed Sep. 29, 2004 and published as WO 2005/032467, hereby incorporated by reference in its entirety. These uses of the present invention are describe in further detail below and include enhancement of learning and training in both human and non-human mammals.

Conditions and diseases treatable or preventable using tissue protective peptides of the present invention directed to the central nervous system include but are not limited to mood disorders, anxiety disorders, depression, autism, attention deficit hyperactivity disorder, and cognitive dysfunction. These conditions benefit from enhancement of neuronal function. Other disorders treatable in accordance with the teachings of the present invention include sleep disruption, for example, sleep apnea and travel-related disorders; subarachnoid and aneurismal bleeds, hypotensive shock, concussive injury, septic shock, anaphylactic shock, and sequelae of various encephalitides and meningitides, for example, connective tissue disease-related cerebritides such as lupus. Other uses include prevention of or protection from poisoning by neurotoxins, such as domoic acid shellfish poisoning, neurolathyrism, and Guam disease, amyotrophic lateral sclerosis, Parkinson's disease; postoperative treatment for embolic or ischemic injury; whole brain irradiation; sickle cell crisis; and eclampsia.

A further group of conditions treatable or preventable using tissue protective peptides of the present invention include mitochondrial dysfunction, of either a hereditary or acquired nature, which are the cause of a variety of neurological diseases typified by neuronal injury and death. For example, Leigh disease (subacute necrotizing encephalopathy) is characterized by progressive visual loss and encephalopathy, due to neuronal drop out, and myopathy. In these cases, defective mitochondrial metabolism fails to supply enough high energy substrates to fuel the metabolism of excitable cells. A tissue protective peptide optimizes failing function in a variety of mitochondrial diseases. As mentioned above, hypoxic conditions adversely affect excitable tissues. The excitable tissues include, but are not limited to, central nervous system tissue, peripheral nervous system tissue, and heart tissue. In addition to the conditions described above, the tissue protective peptides of the present invention are useful in the treatment of inhalation poisoning such as carbon monoxide and smoke inhalation, severe asthma, adult respiratory distress syndrome, and choking and near drowning. Further conditions which create hypoxic conditions or by other means induce responsive tissue, such as excitable tissue damage include hypoglycemia that may occur in inappropriate dosing of insulin, or with insulin-producing neoplasms (insulinoma).

Various neuropsychologic disorders which are described to originate from excitable tissue damage are treatable using tissue protective peptides of the present invention. Chronic disorders in which neuronal damage is involved and for which treatment or preventable by the present invention is provided include disorders relating to the central nervous system and/or peripheral nervous system including age-related loss of cognitive function and senile dementia, chronic seizure disorders, Alzheimer's disease, Parkinson's disease, dementia, memory loss, amyotrophic lateral sclerosis, multiple sclerosis, tuberous sclerosis, Wilson's Disease, cerebral and progressive supranuclear palsy, Guam disease, Lewy body dementia, prion diseases, such as spongiform encephalopathies, e.g., Creutzfeldt-Jakob disease, Huntington's disease, myotonic dystrophy, Freidrich's ataxia and other ataxias, as well as Gilles de la Tourette's syndrome, seizure disorders such as epilepsy and chronic seizure disorder, stroke, brain or spinal cord trauma, AIDS dementia, alcoholism, autism, retinal ischemia, glaucoma, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as unipolar and bipolar affective disorders. Additional neuropsychiatric and neurodegenerative disorders include, for example, those listed in the American Psychiatric Association's Diagnostic and Statistical Manual of Mental Disorders (DSM), the most current version of which in incorporated herein by reference in its entirety.

A further group of conditions treatable or preventable using tissue protective peptides of the present invention include kidney diseases such as renal failure, acute and chronic. Blood supply to the kidneys can be cut off due to several causes including shock from infections invading the bloodstream (septicemia), internal or external hemorrhaging, loss of fluid from the body as a result of severe diarrhea or burns, reactions to transfusions, cardiac arrest or arythmias, surgical trauma and kidney transplantations. The reduced flow of blood to the kidneys resulting from the above conditions may reduced blood flow to dangerously low levels for a time period great enough to cause the development of acute renal failure. The depressed blood flow also results in necrosis, or tissue death, in the kidney, damaging the renal tubular cells. Renal failure may also result from diseases (interstitial and diabetic) nephrotic syndromes, infections, injury (CPB-induced), toxins (contrast-induced, chemotherapy-induced, cyclosporine), autoimmune inflammation (e.g. Lupus, erythrotosis, etc.) The tissue protective peptides of the current invention assist in the repair or prevention of this damage helping to ameliorate acute renal failure.

The following table lists additional exemplary, non-limiting indications as to the various conditions and diseases amenable to treatment by the aforementioned tissue protective peptides.

| Cell, tissue or organ | Dysfunction or pathology | Condition or disease | Type |
| --- | --- | --- | --- |
| Heart | Ischemia | Coronary artery disease | Acute, chronic Stable, unstable |
| | | Myocardial infarction Angina | Dressler's syndrome |
| | | Congenital heart disease | Valvular Cardiomyopathy |
| | | Prinzmetal angina | |
| | | Cardiac rupture | Aneurysmatic Septal perforation |
| | | Angiitis | |
| | Arrhythmia | Tachy-, bradyarrhythmia Supraventricular, ventricular Conduction abnormalities | Stable, unstable Hypersensitive carotid sinus node |
| | Congestive heart failure | Left, right, bi-ventricular, systolic, diastolic | Cardiomyopathies, such as idiopathic familial, infective, metabolic, storage disease, deficiencies, connective tissue disorder, infiltration and granulomas, neurovascular |
| | | Myocarditis | Autoimmune, infective, idiopathic |
| | | Cor pulmonale | |
| | Radiation injury Blunt and penetrating trauma | | |
| | Toxins | Cocaine toxicity, adriamycin | |
| Vascular | Hypertension Decompression sickness Fibromuscular hyperplasia | Primary, secondary | |
| | Aneurysm | Dissecting, ruptured, enlarging | |
| Lungs | Obstructive | Asthma Chronic bronchitis, Emphysema and airway obstruction | |
| | Ischemic lung disease | Pulmonary embolism, Pulmonary thrombosis, Fat embolism | |
| | Environmental lung diseases | | |
| | Ischemic lung disease | Pulmonary embolism Pulmonary thrombosis | |
| | Interstitial lung disease | Idiopathic pulmonary fibrosis | |
| | Congenital Cor pulmonale Trauma | Cystic fibrosis | |
| | Pneumonia and pneumonitides | Infectious, parasitic, toxic, traumatic, burn, aspiration | |
| | Sarcoidosis | | |
| Pancreas | Endocrine | Diabetes mellitus, type I and II Other endocrine cell failure of the pancreas | Beta cell failure, dysfunction Diabetic neuropathy |
| | Exocrine | Exocrine pancreas failure | pancreatitis |

-continued

| Cell, tissue or organ | Dysfunction or pathology | Condition or disease | Type |
|---|---|---|---|
| Bone | Osteopenia | Primary<br>Secondary | Hypogonadism<br>immobilisation<br>Postmenopausal<br>Age-related<br>Hyperparathyroidism<br>Hyperthyroidism<br>Calcium, magnesium, phosphorus and/or vitamin D deficiency |
| | Osteomyelitis<br>Avascular necrosis<br>Trauma<br>Paget's disease | | |
| Skin | Alopecia | Areata<br>Totalis | Primary<br>Secondary<br>Male pattern baldness |
| | Vitiligo | Localized<br>Generalized | Primary<br>secondary |
| | Ulceration | Diabetic<br>Decubitis | Pressure sores, pressure ulcers, bed sores |
| | Peripheral vascular disease<br>Surgical wounds, lacerations<br>Burn injuries | | |
| Autoimmune disorders | Lupus erythematosus, Sjogren's syndrome, Rheumatoid arthritis, Glomerulonephritis, Angiitis<br>Langerhan's histiocytosis | | |
| Eye | Optic neuritis<br>Blunt and penetrating injuries, Infections, Sarcoid, Sickle C disease, Retinal detachment, Temporal arteritis<br>Retinal ischemia, Macular degeneration, Retinitis pigmentosa, Arteriosclerotic retinopathy, Hypertensive retinopathy, Retinal artery blockage, Retinal vein blockage, Hypotension, Diabetic retinopathy, glaucoma and Macular edema | | |
| Embryonic and fetal disorders | Asphyxia<br>Ischemia | | |
| CNS | Chronic fatigue syndrome, acute and chronic hypoosmolar and hyperosmolar syndromes, AIDS Dementia, Electrocution<br>Cerebral malaria | | |
| | Encephalitis | Rabies, Herpes, | |
| | Meningitis<br>Subdural hematoma<br>Nicotine addiction | | |
| | Drag abuse and withdrawal | Cocaine, heroin, crack, marijuana, LSD, PCP, poly-drug abuse, ecstasy, opioids, sedative hypnotics, amphetamines, caffeine | |
| | Obsessive-compulsive disorders<br>Spinal stenosis, Transverse myelitis, Guillian Barre, Trauma, Nerve root compression, Tumoral compression, Heat stroke | | |

-continued

| Cell, tissue or organ | Dysfunction or pathology | Condition or disease | Type |
|---|---|---|---|
| ENT | Tinnitus | | |
| | Meuniere's syndrome | | |
| | Hearing loss | | |
| | Traumatic injury, barotraumas | | |
| Kidney | Renal failure | Acute, chronic | Vascular/ischemic, interstitial disease, diabetic kidney disease, nephrotic syndromes, infections, injury, contrast-induced, chemotherapy-induced, cyclosporine, CPB-induced, or preventive |
| | Radiation injury | | |
| | Henoch | | |
| | Schonlein purpura | | |
| Striated muscle | Autoimmune disorders | Myasthenia gravis | |
| | | Dermatomyositis | |
| | | Polymyositis | |
| | Myopathies | Inherited metabolic, endocrine and toxic | |
| | Heat stroke | | |
| | Crush injury | | |
| | Rhabdomyolysis | | |
| | Mitochondrial disease | | |
| | Infection | Necrotizing fasciitis | |
| Sexual dysfunction | Central and peripheral (e.g. erectile dysfunction) | Impotence secondary to medication, (diabetes) | |
| Liver | Hepatitis | Viral, bacterial, parasitic | |
| | Ischemic disease | | |
| | Cirrhosis, fatty liver | | |
| | Infiltrative/metabolic diseases | | |
| Gastrointestinal | Ischemic bowel disease | | |
| | Inflammatory bowel disease | | |
| | Necrotizing enterocolitis | | |
| Organ transplantation | Treatment of donor and recipient | | |
| Reproductive tract | Infertility | Vascular | |
| | | Autoimmune | |
| | | Uterine abnormalities | |
| | | Implantation disorders | |
| Endocrine | Glandular hyper- and hypofunction | | |
| General | Shock | Septic, hemodynamic | |
| | Parasitemia | Malaria, trypanosomiasis, Leshmaniasis | |

As mentioned above, these diseases, disorders or conditions are merely illustrative of the range of benefits provided by the tissue protective peptides of the present invention. Accordingly, this invention generally provides preventative, therapeutic, or prophylactic treatment of the consequences of mechanical trauma or of human diseases. Prevention or therapeutic or prophylactic treatment for diseases, disorders or conditions of the CNS and/or peripheral nervous system are contemplated. Prevention or therapeutic or prophylactic treatment for diseases, disorders or conditions which have a psychiatric component is provided. Prevention or therapeutic or prophylactic treatment for diseases, disorders or conditions including but not limited to those having an ophthalmic, cardiovascular, cardiopulmonary, respiratory, kidney, urinary, reproductive, gastrointestinal, endocrine, or metabolic component is provided.

In one embodiment, such a pharmaceutical composition comprising a tissue protective peptide can be administered systemically to protect or enhance the target cells, tissue or organ. Such administration may be parenterally, via inhalation, or transmucosally, e.g., orally, nasally, rectally, intravaginally, sublingually, ocularly, submucosally or transdermally. Preferably, administration is parenteral, e.g., via intravenous or intraperitoneal injection, and also including, but is not limited to, intra-arterial, intramuscular, intradermal and subcutaneous administration.

For other routes of administration, such as by use of a perfusate, injection into an organ, or other local administration, a pharmaceutical composition will be provided which results in similar levels of a tissue protective peptide as described above. A level of about 15 pM-30 nM is preferred.

The pharmaceutical compositions of the invention may comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin, hereby incorporated by reference herein in its entirety. Such compositions will contain a therapeutically effective amount of the compound, preferably in purified form, together with a suitable amount of carrier so as to provide the form for proper administration to the patient. The formulation should suit the mode of administration.

Formulations for increasing transmucosal adsorption of peptides such as long acting tissue protective peptides are also contemplated by the current invention. Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal and pulmonary administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. Alternatively, inhalation of compounds directly into the lungs may be accomplished by inhalation deeply or installation through a mouthpiece into the oropharynx. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered into the nasal cavity directly or into the lungs via the nasal cavity or oropharynx.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of a tissue protective peptide may be provided for emergency use by ambulances, emergency rooms, and battlefield situations, and even for self-administration in a domestic setting, particularly where the possibility of traumatic amputation may occur, such as by imprudent use of a lawn mower. The likelihood that cells and tissues in a severed foot or toe will survive after reattachment may be increased by administering a tissue protective peptide to multiple sites in the severed part as soon as practicable, even before the arrival of medical personnel on site, or arrival of the afflicted individual with severed toe in tow at the emergency room.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

Suppositories generally contain active ingredient in the range of 0.5% to 10% by weight; oral formulations preferably contain 10% to 95% active ingredient.

A perfusate composition may be provided for use in transplanted organ baths, for in situ perfusion, or for administration to the vasculature of an organ donor prior to organ harvesting. Such pharmaceutical compositions may comprise levels of tissue protective peptides, or a form of tissue protective peptides not suitable for acute or chronic, local or systemic administration to an individual, but will serve the functions intended herein in a cadaver, organ bath, organ perfusate, or in situ perfusate prior to removing or reducing the levels of the tissue protective peptide contained therein before exposing or returning the treated organ or tissue to regular circulation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, for example, a tissue protective peptide can be delivered in a controlled-release system. For example, the peptide may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574, each of which is incorporated by reference herein in its entirety). In another embodiment, the compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327; see generally ibid.). In another embodiment, polymeric materials can be used (see Medical Applications of Controlled Release, Langer and Wise (eds.), CRC Press: Boca Raton, Fla., 1974; Controlled Drug Bioavailability, Drug Product Design and Performance, Smolen And Ball (eds.), Wiley: New York (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105, (each of which is incorporated by reference herein in its entirety).

In yet another embodiment, a controlled release system can be placed in proximity of the therapeutic target, i.e., the target cells, tissue or organ, thus requiring only a fraction of the systemic dose (see, e.g., Goodson, pp. 115-138 in Medical Applications of Controlled Release, vol. 2, supra, 1984, which is incorporated by reference herein in its entirety). Other controlled release systems are discussed in the review by Langer (1990, Science 249:1527-1533, which is incorporated by reference herein in its entirety).

In another embodiment, tissue protective peptide, as properly formulated, can be administered by nasal, oral, rectal, vaginal, ocular, transdermal, parenteral or sublingual administration.

In a specific embodiment, it may be desirable to administer a tissue protective peptide of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. A non-limiting example of such an embodiment would be a coronary stent coated with a tissue protective peptide of the present invention.

Selection of the preferred effective dose will be readily determinable by a skilled artisan based upon considering several factors, which will be known to one of ordinary skill in the art. Such factors include the particular form of tissue protective peptide, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, and according to standard clinical techniques.

In another aspect of the present invention, a pharmaceutical composition according to the present invention may include a tissue protective peptide in a formulation with at least one small molecule that exhibits tissue protective functionality. Suitable small molecules include, but are not limited to, steroids (e.g., lazaroids and glucocorticoids), antioxidants (e.g., coenzyme $Q_{10}$, alpha lipoic acid, and NADH), anticatabolic enzymes (e.g., glutathione peroxidase, superoxide dimutase, catalase, synthetic catalytic scavengers, as well as mimetics), indole derivatives (e.g., indoleamines, carbazoles, and carbolines), nitric acid neutralizing agents, adenosine/adenosine agonists, phytochemicals (flavanoids), herbal extracts (ginko biloba and turmeric), vitamins (vitamins A, E, and C), oxidase electron acceptor inhibitors (e.g., xanthine oxidase electron inhibitors), minerals (e.g., copper, zinc, and magnesium), non-steriodal anti-inflammatory drugs (e.g., aspirin, naproxen, and ibuprofen), and combinations thereof. Additionally agents including, but not limited to, anti-inflammatory agents (e.g., corticosteroids, prednisone and hydrocortisone), glucocorticoids, steroids, non-steriodal anti-inflammatory drugs (e.g., aspirin, ibuprofen, diclofenac, and COX-2 inhibitors), beta-agonists, anticholinergic agents and methyl xanthines), immunomodulatory agents (e.g., small organic molecules, T cell receptor modulators, cytokine receptor modulators, T-cell depleting agents, cytokine antagonists, monokine antagonists, lymphocyte inhibitors, or anti-cancer agents), gold injections, sulphasalazine, penicillamine, anti-angiogenic agents (e.g., angiostatin), TNF-α antagonists (e.g., anti-TNFα antibodies), and endostatin), dapsone, psoralens (e.g., methoxalen and trioxsalen), antimalarial agents (e.g., hydroxychloroquine), anti-viral agents, and antibiotics (e.g., erythromycin and penicillin) may be used in conjunction with the current pharmaceutical compositions.

In another aspect of the invention, a perfusate or perfusion solution is provided for perfusion and storage of organs for transplant, the perfusion solution includes an amount of a tissue protective peptide effective to protect responsive cells and associated cells, tissues or organs. Transplant includes but is not limited to allotransplantation, where an organ (including cells, tissue or other bodily part) is harvested from one donor and transplanted into a different recipient, both being of the same species; autotransplantation, where the organ is taken from one part of a body and replaced at another, including bench surgical procedures, in which an organ may be removed, and while ex vivo, resected, repaired, or otherwise manipulated, such as for tumor removal, and then returned to the original location or xenotransplantation, where tissues or organs or transplanted between species. In one embodiment, the perfusion solution is the University of Wisconsin (UW) solution (U.S. Pat. No. 4,798,824, hereby incorporated by reference herein in its entirety) which contains from about 1 to about 25 U/ml (10 ng=1U) of tissue protective peptide, 5% hydroxyethyl starch (having a molecular weight of from about 200,000 to about 300,000 and substantially free of ethylene glycol, ethylene chlorohydrin, sodium chloride and acetone); 25 mM $KH_2PO_4$; 3 mM glutathione; 5 mM adenosine; 10 mM glucose; 10 mM HEPES buffer; 5 mM magnesium gluconate; 1.5 mM $CaCl_2$; 105 mM sodium gluconate; 200,000 units penicillin; 40 units insulin; 16 mg dexamethasone; 12 mg Phenol Red; and has a pH of 7.4-7.5 and an osmolality of about 320 mOsm/l. The solution is used to maintain cadaveric kidneys and pancreases prior to transplant. Using the solution, preservation can be extended beyond the 30-hour limit recommended for cadaveric kidney preservation. This particular perfusate is merely illustrative of a number of such solutions that can be adapted for the present use by inclusion of an effective amount of a tissue protective peptide. In a further embodiment, the perfusate solution contains from about 1 to about 500 ng/ml of a tissue protective peptide, or from about 40 to about 320 ng/ml tissue protective peptide. As mentioned above, any form of tissue protective peptide can be used in this aspect of the invention.

While the preferred recipient of a tissue protective peptide for the purposes herein throughout is a human, the methods herein apply equally to other mammals, particularly domesticated animals, livestock, companion, and zoo animals. However, the invention is not so limiting and the benefits can be applied to any mammal.

In further aspects of the ex-vivo invention, any tissue protective peptide such as but not limited to the ones described above may be employed.

In another aspect of the invention, methods and compositions for enhancing the viability of cells, tissues or organs which are not isolated from the vasculature by an endothelial cell barrier are provided by exposing the cells, tissue or organs directly to a pharmaceutical composition comprising a tissue protective peptide, or administering or contacting a pharmaceutical composition containing a tissue protective peptide to the vasculature of the tissue or organ. Enhanced activity of responsive cells in the treated tissue or organ is responsible for the positive effects exerted.

Similar to other tissue protective compounds based on erythropoietin, it is possible that the tissue protective peptides of the present invention may be transported from the luminal surface to the basement membrane surface of endothelial cells of the capillaries of organs with endothelial cell tight junctions, including, for example, the brain, retina, and testis. Thus, responsive cells across the barrier may be susceptible targets for the beneficial effects of tissue protective peptides, and others cell types or tissues or organs that contain and depend in whole or in part on responsive cells therein may be targets for the methods of the invention. While not wishing to be bound by any particular theory, after transcytosis of the tissue protective peptide may interact with an tissue-protective receptor on a responsive cell, for example, neuronal, eye (e.g., retinal), adipose, connective, hair, tooth, mucosal, pancreatic, endocrine, aural, epithelial, skin, muscle, heart, lung, liver, kidney, small intestine, adrenal (e.g. adrenal cortex, adrenal medulla), capillary, endothelial, testes, ovary, or endometrial cell, and receptor binding can initiate a signal transduction cascade resulting in the activation of a gene expression program within the responsive cell or tissue, resulting in the protection of the cell or tissue, or organ, from damage, such as by toxins, chemotherapeutic agents, radiation therapy, hypoxia, etc. In another embodiment, the tissue protective peptide can be cross-linked to a compound that can cross the barrier, such as carbamylated erythropoietin, to be transported across the barrier in accordance with the teaching of PCT Application No. PCT/US01/49479, U.S. patent application Ser. Nos. 10/188,905 and 10/185,841, incorporated herein by reference. Thus, methods for protecting responsive cell-containing tissue from injury or hypoxic stress, and enhancing the function of such tissue are described in detail herein below.

In the practice of one embodiment of the invention, a mammalian patient is undergoing systemic chemotherapy for cancer treatment, including radiation therapy, which commonly has adverse effects such as nerve, lung, heart, ovarian or testicular damage. Administration of a pharmaceutical composition comprising a tissue protective peptide as described above is performed prior to and during chemotherapy and/or radiation therapy, to protect various tissues and organs from damage by the chemotherapeutic agent, such as to protect the testes. Treatment may be continued until circulating levels of the chemotherapeutic agent have fallen below a level of potential danger to the mammalian body.

In the practice of another embodiment of the invention, various organs are planned to be harvested from a victim of an automobile accident for transplant into a number of recipients, some of which required transport for an extended distance and period of time. Prior to organ harvesting, the donor is infused with a pharmaceutical composition comprising tissue protective peptides as described herein. Harvested organs for shipment are perfused with a perfusate containing tissue protective peptides as described herein, and stored in a bath comprising tissue protective peptides. Certain organs are continuously perfused with a pulsatile perfusion device, utilizing a perfusate containing tissue protective peptides in accordance with the present invention. Minimal deterioration of organ function occurs during the transport and upon implant and reperfusion of the organs in situ.

In another embodiment of the present invention, a participant in a hazardous activity, one could take a dose of a pharmaceutical composition containing a tissue protective peptide sufficient to either prevent (i.e. delaying the onset of, inhibiting, or stopping), protect against, or mitigate the damage resulting from an injury to a responsive cell, tissue, or organ. In particular, this method of treatment may have application in various professions susceptible to injury such as, but not limited to, professional athletes (divers, race car drivers, football players, etc.), military personnel (soldiers, paratroopers), emergency personnel (police, fire, EMS, and disaster relief personnel), stuntmen, and construction workers.

Additionally, the prophylactic use of tissue protective peptides is contemplated in such recreational endeavors including, but not limited to, rock climbing, rappelling, sky diving, racing, bicycling, football, rugby, baseball, and diving that pose a risk of injury.

In another embodiment of the invention, a surgical procedure to repair a heart valve requires temporary cardioplegia and arterial occlusion. Prior to surgery, the patient is infused with a tissue protective peptide. Such treatment prevents hypoxic ischemic cellular damage, particularly after reperfusion. Additionally, the pharmaceutical compositions of the present invention may be used prophylactically to prepare an individual for surgery in an effort to limit the trauma associated with the surgical procedure or aide in the recovery of the individual from the surgical procedure. Although the present method of treatment using pharmaceutical compositions containing tissue protective peptides provides a prophylactic use for surgical procedures, it may be particularly useful in procedures that induce temporary ischemic events including, but not limited to, bypass procedures (coronary bypass), angioplasty procedures, amputations, and transplantations, as well as, those performed directly upon responsive cells, tissues, or organs such as brain and spinal cord surgery, and open heart procedures. Such procedures may involve the use of cardiopulmonary (heart lung) bypass.

In another embodiment of the invention, in any surgical procedure, such as in cardiopulmonary bypass surgery, a tissue protective peptide of the invention can be used. In one embodiment, administration of a pharmaceutical composition comprising tissue protective peptides as described above is performed prior to, during, and/or following the bypass procedure, to protect the function of brain, heart, and other organs.

In the foregoing examples in which a tissue protective peptide of the invention is used for ex-vivo applications, or for in vivo applications to treat responsive cells such as neuronal tissue, retinal tissue, heart, lung, liver, kidney, small intestine, adrenal cortex, adrenal medulla, capillary endothelial, testes, ovary, or endometrial cells or tissue, the invention provides a pharmaceutical composition in dosage unit form adapted for protection or enhancement of responsive cells, tissues or organs distal to the vasculature which comprises an amount within the range from about 0.01 pg to 7.5 mg, 0.5 pg to 6.5 mg, 1 pg to 5 mg, 500 pg to 5 mg, 1 ng to 5 mg, 500 ng to 5 mg, 1 µg to 5 mg, 500 µg to 5 mg, or 1 mg to 5 mg of a tissue protective peptide, and a pharmaceutically acceptable carrier. In a preferred embodiment, the amount of tissue protective peptide is within the range from about 0.5 pg to 1 mg. In a preferred embodiment, the formulation contains tissue protective peptides that are non-erythropoietic.

In a further aspect of the invention, administration of tissue protective peptides may be used to restore cognitive function in mammals having undergone brain trauma. After a delay of either 5 days or 30 days, administration of tissue protective peptides should be able to restore function as compared to placebo-treated mammals, indicating the ability of the tissue protective peptide to regenerate or restore brain activity. Thus, the invention is also directed to the use of tissue protective peptides for the preparation of a pharmaceutical composition for the treatment of brain trauma and other cognitive dysfunctions, including treatment well after the injury (e.g. three days, five days, a week, a month, or longer). The invention is also directed to a method for the treatment of cognitive dysfunction following injury by administering an effective amount of tissue protective peptides. Any tissue protective peptide as described herein may be used for this aspect of the invention.

Furthermore, this restorative aspect of the invention is directed to the use of any tissue protective peptides herein for the preparation of a pharmaceutical composition for the restoration of cellular, tissue or organ dysfunction, wherein treatment is initiated after, and well after, the initial insult responsible for the dysfunction. Moreover, treatment using tissue protective peptides of the invention can span the course of the disease or condition during the acute phase as well as a chronic phase.

A tissue protective peptide of the invention may be administered systemically at a dosage between about 1 ng and about 100 µg/kg body weight, preferably about 5-50 µg/kg-body weight, most preferably about 10-30 µg/kg-body weight, per administration. This effective dose should be sufficient to achieve serum levels of tissue protective peptides greater than about 80, 120, or 160 ng/ml of serum after administration. Such serum levels may be achieved at about 1, 2, 3, 4, 5, 6, 7, 8, 9, or 10 hours post-administration. Such dosages may be repeated as necessary. For example, administration may be repeated daily, as long as clinically necessary, or after an appropriate interval, e.g., every 1 to 12 weeks, preferably, every 1 to 3 weeks. In one embodiment, the effective amount of tissue protective peptide and a pharmaceutically acceptable carrier may be packaged in a single dose vial or other container. In another embodiment, the tissue protective peptides, which are capable of exerting the activities described herein but not causing an increase in hemoglobin concentration or hematocrit, are used. Such tissue protective peptides are preferred in instances wherein the methods of the present invention are intended to be provided chronically.

5.4 Transcytosis

Carrier Molecule and Tissue Protective Peptide. The present invention is further directed to a method for facilitating the transport of a Tissue Protective Peptide across an endothelial cell barrier in a mammal by administering a composition which comprises the tissue protective peptide in association with a carrier peptide, a peptide capable of crossing an endothelial cell barrier, such as erythropoietin, as described hereinabove. Tight junctions between endothelial cells in certain organs in the body create a barrier to the entry of certain molecules. For treatment of various conditions within the barriered organ, means for facilitating passage of the tissue protective peptide may be desired.

Tissue Protective Peptide as Carrier Molecule. Tissue protective peptides of the invention may be useful as carriers for delivering other molecules across the blood-brain and other similar barriers which they can travel across. A composition comprising a molecule desirous of crossing the barrier with a tissue protective peptide is prepared and peripheral administration of the composition results in the transcytosis of the composition across the barrier. The association between the molecule to be transported across the barrier and the tissue protective peptide may be a labile covalent bond, in which case the molecule is released from association with the tissue protective peptide after crossing the barrier. If the desired pharmacological activity of the molecule is maintained or unaffected by association with tissue protective peptides, such a complex can be administered.

The skilled artisan will be aware of various means for associating molecules with tissue protective peptides of the invention and the other agents described above, by covalent, non-covalent, and other means. Furthermore, evaluation of the efficacy of the composition can be readily determined in an experimental system. Association of molecules with tissue protective peptides may be achieved by any number of means, including labile, covalent binding, cross-linking, etc. Biotin/avidin interactions may be employed; for example, a biotinylated tissue protective peptides of the invention may be complexed with a labile conjugate of avidin and a molecule desirably transported. As mentioned above, a hybrid molecule may be prepared by recombinant or synthetic means, for example, a fusion or chimeric polypeptide which includes both the domain of the molecule with desired pharmacological activity and the domain responsible for the peptides tissue-protective receptor activity modulation. Protease cleavage sites may be included in the molecule.

A molecule may be conjugated to a tissue protective peptide of the invention through a polyfunctional molecule, i.e., a polyfunctional crosslinker. As used herein, the term "polyfunctional molecule" encompasses molecules having one functional group that can react more than one time in succession, such as formaldehyde, as well as molecules with more than one reactive group. As used herein, the term "reactive group" refers to a functional group on the crosslinker that reacts with a functional group on a molecule (e.g., peptide, protein, carbohydrate, nucleic acid, particularly a hormone, antibiotic, or anti-cancer agent to be delivered across an endothelial cell barrier) so as to form a covalent bond between the cross-linker and that molecule. The term "functional group" retains its standard meaning in organic chemistry. The polyfunctional molecules that can be used are preferably biocompatible linkers, i.e., they are noncarcinogenic, nontoxic, and substantially non-immunogenic in vivo. Polyfunctional cross-linkers such as those known in the art and described herein can be readily tested in animal models to determine their biocompatibility. The polyfunctional molecule is preferably bifunctional. As used herein, the term "bifunctional molecule" refers to a molecule with two reactive groups. The bifunctional molecule may be heterobifunctional or homobifunctional. A heterobifunctional cross-linker allows for vectorial conjugation. It is particularly preferred for the polyfunctional molecule to be sufficiently soluble in water for the cross-linking reactions to occur in aqueous solutions such as in aqueous solutions buffered at pH 6 to 8, and for the resulting conjugate to remain water soluble for more effective bio-distribution. Typically, the polyfunctional molecule covalently bonds with an amino or a sulfhydryl functional group. However, polyfunctional molecules reactive with other functional groups, such as carboxylic acids or hydroxyl groups, are contemplated in the present invention.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., Science 223, 1304-1306 (1984). Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. The reactive groups react with different functional groups, e.g., present on the peptide and the molecule. These two different functional groups that react with the reactive group on the heterobifunctional cross-linker are usually an amino group, e.g., the epsilon amino group of lysine; a sulfhydryl group, e.g., the thiol group of cysteine; a carboxylic acid, e.g., the carboxylate on aspartic acid; or a hydroxyl group, e.g., the hydroxyl group on serine.

Of course, certain of the various tissue protective peptides of the invention, may not have suitable reactive groups available for use with certain cross-linking agent; however, one of skill in the art will be amply aware of the choice of cross-linking agents based on the available groups for cross-linking in tissue protective peptides of the invention.

When a reactive group of a heterobifunctional molecule forms a covalent bond with an amino group, the covalent bond will usually be an amido or imido bond. The reactive group that forms a covalent bond with an amino group may, for example, be an activated carboxylate group, a halocarbonyl group, or an ester group. The preferred halocarbonyl group is a chlorocarbonyl group. The ester groups are preferably reactive ester groups such as, for example, an N-hydroxy-succinimide ester group.

The other functional group typically is either a thiol group, a group capable of being converted into a thiol group, or a group that forms a covalent bond with a thiol group. The covalent bond will usually be a thioether bond or a disulfide. The reactive group that forms a covalent bond with a thiol group may, for example, be a double bond that reacts with thiol groups or an activated disulfide. A reactive group containing a double bond capable of reacting with a thiol group is the maleimido group, although others, such as acrylonitrile, are also possible. A reactive disulfide group may, for example, be a 2-pyridyldithio group or a 5,5'-dithio-bis-(2-nitrobenzoic acid) group. Some examples of heterobifunctional reagents containing reactive disulfide bonds include N-succinimidyl 3-(2-pyridyl-dithio) propionate (Carlsson, et al., 1978, Biochem J., 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio) propionate is preferred. Some examples of heterobifunctional reagents comprising reactive groups having a double bond that reacts with a thiol group include succinimidyl 4-(N-maleimidomethyl)cyclohexane-1-carboxylate and succinimidyl m-maleimidobenzoate.

Other heterobifunctional molecules include succinimidyl 3-(maleimido) propionate, sulfosuccinimidyl 4-(p-maleimido-phenyl) butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce Chemical Co., Rockford, Ill. USA.

The need for the above-described conjugated to be reversible or labile may be readily determined by the skilled artisan. A conjugate may be tested in vitro for desirable pharmacological activity. If the conjugate retains both properties (the properties of the conjugated molecule and the properties of the tissue protective peptide), its suitability may then be tested in vivo. If the conjugated molecule requires separation from the tissue protective peptide for activity, a labile bond or reversible association with long acting erythropoietin or the long acting tissue protective cytokine will be preferable. The lability characteristics may also be tested using standard in vitro procedures before in vivo testing.

Additional information regarding how to make and use these as well as other polyfunctional reagents may be obtained from the following publications or others available in the art:

Carlsson, J. et al., 1978, Biochem. J. 173:723-737;
Cumber, J. A. et al., 1985, Methods in Enzymology 112:207-224;

Jue, R. et al., 1978, Biochem 17:5399-5405;
Sun, T. T. et al., 1974, Biochem. 13:2334-2340;
Blattler, W. A. et al., 1985, Biochem. 24:1517-152;
Liu, F. T. et al., 1979, Biochem. 18:690-697;
Youle, R. J. and Neville, D. M. Jr., 1980, Proc. Natl. Acad. Sci. U.S.A. 77:5483-5486;
Lerner, R. A. et al., 1981, Proc. Natl. Acad. Sci. U.S.A. 78:3403-3407;
Jung, S. M. and Moroi, M., 1983, Biochem. Biophys. Acta 761:162;
Caulfield, M. P. et al., 1984, Biochem. 81:7772-7776;
Staros, J. V., 1982, Biochem. 21:3950-3955;
Yoshitake, S. et al., 1979, Eur. J. Biochem. 101:395-399;
Yoshitake, S. et al., 1982, J. Biochem. 92:1413-1424;
Pilch, P. F. and Czech, M. P., 1979, J. Biol. Chem. 254:3375-3381;
Novick, D. et al., 1987, J. Biol. Chem. 262:8483-8487;
Lomant, A. J. and Fairbanks, G., 1976, J. Mol. Biol. 104:243-261;
Hamada, H. and Tsuruo, T., 1987, Anal. Biochem. 160:483-488; or
Hashida, S. et al., 1984, J. Applied Biochem. 6:56-63, each of which is hereby incorporated by reference in its entirety.

Additionally, methods of cross-linking are reviewed by Means and Feeney, 1990, Bioconjugate Chem. 1:2-12, hereby incorporated by reference in its entirety.

Barriers which are crossed by the above-described methods and compositions of the present invention include but are not limited to the blood-brain barrier, the blood-eye barrier, the blood-testes barrier, the blood-ovary barrier, blood-nerve barrier, blood-spinal cord barrier, and blood-placenta barrier.

Candidate molecules for transport across an endothelial cell barrier include, for example, hormones, such as growth hormone, neurotrophic factors, antibiotics, antivirals, or antifungals such as those normally excluded from the brain and other barriered organs, peptide radiopharmaceuticals, antisense drugs, antibodies and antivirals against biologically-active agents, pharmaceuticals, and anti-cancer agents. Non-limiting examples of such molecules include hormones such as growth hormone, nerve growth factor (NGF), brain-derived neurotrophic factor (BDNF), ciliary neurotrophic factor (CNTF), basic fibroblast growth factor (bFGF), transforming growth factor β1 (TGFβ1), transforming growth factor β2 (TGFβ2), transforming growth factor β3 (TGFβ3), interleukin 1, interleukin 2, interleukin 3, and interleukin 6, AZT, antibodies against tumor necrosis factor, and immunosuppressive agents such as cyclosporin. Additionally, dyes or markers may be attached to the tissue protective peptides of the present invention in order to visualize cells, tissues, or organs within the brain and other barriered organs for diagnostic purposes. As an example, a marker used to visualize plaque within the brain could be attached to a tissue protective peptide in order to determine the progression of Alzheimer's disease within a patient.

The present invention is also directed to a composition comprising a molecule to be transported via transcytosis across an endothelial cell tight junction barrier and a tissue protective peptide as described above. The invention is further directed to the use of a conjugate between a molecule and a tissue protective peptide cytokine as described above for the preparation of a pharmaceutical composition for the delivery of the molecule across a barrier as described above.

Various animal models and in-vitro tests of neuroprotection and transcytosis are provided in PCT/US01/49479 (hereby incorporated by reference in its entirety) to demonstrate the effectiveness of the tissue protective peptides of the invention. For transcytosis, model proteins conjugated to the long acting erythropoietins of the invention are evaluated for transport into the brain following parenteral administration. These tests in in-vitro models and animal models are predictive of the efficacy of the present compounds in other mammalian species including humans.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

6. EXAMPLES

Example 1

Method of Peptide Synthesis

A. Synthesis of Peptide A (SEQ ID NO:32, corresponding to EPO amino acid sequence 38-57) and Peptide B (SEQ ID NO:34, corresponding to EPO amino acid sequence 58-82).

Peptide A, SEQ ID NO:32, and Peptide B, SEQ ID NO:34, fragments of EPO (see Table 1), were synthesized using "in situ neutralization" Boc Chemistry stepwise solid-phase peptide synthesis, as described in Band, D., Chopra, N. and Kent, S., "Total Synthesis of Crambin," J. AM. CHEM. SOC. 2004, 126, 1377-1383 (incorporated by reference herein in its entirety). Briefly, two fragments corresponding to EPO amino acid sequence 38-57 (peptide C, NITVPDTKVN-FYAWKRMEVG, SEQ ID NO:29) and EPO amino acid sequence 58-82 (peptide D, QQAVEVWQGLALLSEAVL-RGQALLV, SEQ ID NO:30) were synthesized on —OCH$_2$-Pam-resins (free $^\alpha$carboxyl peptides) or on HSCH$_2$CH$_2$CO-Leu-OCH$_2$-Pam-Resin ($^\alpha$thioester peptides). During synthesis the side chains of various amino acids were protected as follows: Arg(Tos), Asn(Xan), Asp(OcHex), Cys(4-CH$_3$Bzl) or Cys(ACM), Glu(OcHex), Lys(2-Cl—Z), Ser (Bzl), Thr(Bzl), Tyr(Br—Z). After the peptide chain was assembled, the peptides were deprotected and simultaneously cleaved from the resin support by treatment with anhydrous HF containing p-cresol (90:10, v/v) for 1 hr at 0° C. After evaporation of the HF under reduced pressure, crude products were precipitated and triturated with chilled diethyl ether, and the peptides were dissolved in 50% aqueous acetonitrile containing 0.1% TFA and purified by the preparative HPLC system. Peptide compositions were confirmed using LC-MS.

Example 2

Validation of Peptide-Mediated Tissue Protection

The tissue protective peptides were tested for any tissue protective activity using a Sciatic Nerve Assay. Sprague-Dawley rats (250-300 grams) (six per group, including control) were anesthetized using isoflurane (Baxter NPC 10019-773-60) and a Table Top Laboratory Anesthesia System (flowmeter set to 2-3 liters/minute @ 55 psi) for at least 3 minutes. The rat was then placed on a homeothermic blanket to ensure that the core temperature of the rat was maintained at 35-37° C. during the operation. Core temperature was monitored via a rectal probe. The right sciatic nerve of the anesthetized rat was exposed at mid thigh through a quadriceps muscle dissection; a 2 cm incision with a 15 blade scalpel was made through the skin parallel and over the quadriceps muscle and the quadriceps muscle was cut to expose the sciatic nerve using a pair of dissecting scissors. The sciatic nerve was then freed from the surrounding membranes. A 2-0 braided silk thread (Ethicon, 685-G) was passed under the nerve and the ends of the suture passed through a guide which was maintained perpendicular to the nerve. The end of the suture was then tied to a non-elastic cord which was then draped around the pulley system (a NYL pulley bearing MTD ¼"B (PO Number 04174-01) with stabilizer) and a 100 gram weight attached to the non-elastic cord was slowly released. The weight was allowed to hang for 1 minute before the silk suture was cut to release the weight.

A 289 pmol/kg dose of carbamylated erythropoietin, a 289 pmol/kg dose of one peptide from the series A-J (see Table 1), or PBS was then injected into the caudal vein using a ½ cc insulin syringe. A 20 mer fragment (corresponding to amino acids 102-121) from pigment epithelium-derived growth factor (PEDF) which does not follow the teaching above was used as control.

The muscle and surgical incision were then closed and 5 ml of Lactated Ringers solution was injected subcutaneously into the rat. The core temperature of the rat was maintained at 35-37° C. using a heat blanket during recovery.

index was then computed in accordance with S. Erbayraktar et al., 2003, Proc Natl Acad Sci USA 100, 6741-6746 (hereby incorporated by reference in its entirety) and statistical analysis performed.

Figure 2:
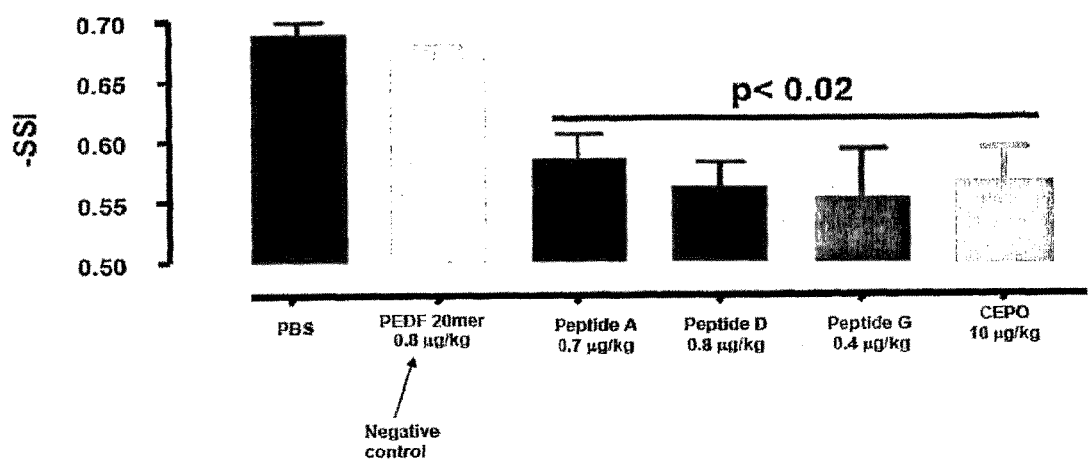

All peptides except B (SEQ ID NO:34), H (SEQ ID NO:47) and the PEDF derivative were equally protective, providing a static sciatic index ("SSI") of about −0.57 versus a SSI of about −67 to about −68 for PBS/PEDF fragment (FIG. 2). FIG. 2 also shows that the efficacy of the positive peptides was at least equivalent, if not improved, over that of the carbamylated erythropoietin.

Table 1 also presents the approximate distance between carbonyl carbons for the tested peptides. Distances were calculated using the three-dimensional coordinates provided by Cheetham et al., 1998, Nat. Struct. Biol. 5:861-866, hereby incorporated by reference. The peptides which tested positive for tissue protective activity each had a carbonyl carbon to carbonyl carbon distance/separation of between about 3 Å to about 5 Å.

TABLE 1

Tissue protective efficacy of representative peptides using an in vivo bioassay (sciatic nerve injury model).

| Peptide Class | | peptide | EPO sequence | Structure | Appprox Distance Between carbonyl Carbons (Angstrom) | Dose [nmoles/ kg-bw] | Sciatic nerve assay |
|---|---|---|---|---|---|---|---|
| A) EPO fragment | | A | 1-23 | APPRLICDSRVLERYLLEAKEAE (SEQ ID NO: 32) | 4.6 | 29, 290, | + |
| | | | | APPRLICDSRVLERYLLEAKEAE (SEQ ID NO: 32) | 4.4 | 1450 | |
| | | B | 24-37 | NITTGCAEHCSLNE (SEQ ID NO: 34) | 2.8 | 290 | − |
| | | C | 38-57 | NITVPDTKVNFYAWKRMEVG (SEQ ID NO: 29) | 4.6 | 290 | + |
| | | D | 58-82 | QQAVEVWQGLALLSEAVLRGQALLV (SEQ ID NO: 30) | 4.8 | 29, 290, 1450 | + |
| | | E | 28-47 | GCAEHCSLNENITVPDTKVN (SEQ ID NO: 31) | 4.4 | 290 | + |
| | | F | 14-29 | RYLLEAKEAENITTGC (SEQ ID NO: 33) | 3.6 | 290 | + |
| B) Helix face | | G | 58, 62, 65, 69, 72, 76, 79, 80, 83, 84, 85 | QEQLERALNSS (SEQ ID NO: 40) | 3.6 | 290 | + |
| | | H | 71, 72, 75, 76, 77 | SELRGQ (SEQ ID NO: 47) | 7.2 | 290 | − |
| C) chimera | | I | Peptide G + β-pleated sheet (33-39) | CSLNENIQEQLERALNSS (SEQ ID NO: 43) | | 290 | + |
| | | J | Peptide G + pancreatic polypeptide helix | QEQLERALNSSLRRYINMLTRTR (SEQ ID NO: 41) | | 290 | + |
| D) Type 1 cytokine motif | | K | GM-CSF helix A (13-26) | WEHVNAIQEARRLL (SEQ ID NO: 35) | 3.6 | 290 | + |
| | | | | WEHVNAIQEARRLL (SEQ ED NO: 35) | 4.6 | | |
| | | | | WEHVNAIQEARRLL (SEQ ID NO: 35) | 4.6 | | |
| | | L | CNTF helix A (26-41) | KIRSDLTALTESYVKH (SEQ ID NO: 37) | 4.7 | 290 | + |

Over the next four days the rear toe splaying of the rats was determined by placing the rat in an acrylic tube with a diameter of 30 cm on the scanning surface of a digital scanner. After waiting 5 minutes in order to permit acclimation, a scan was taken of the rat's back feet that clearly displayed all 5 toes. Three acceptable scans of each rat were taken. From the scans, the Toe Spread (the distance between the ball of the first toe and the ball of the fifth toe) and the Intermediate Toe Spread (the distance between the ball of the second toe and the ball of the fourth toe) were measured. The static sciatic Example 3

Tissue Protective Peptides are Non Erythropoietic

A. In Vitro Assessment:

UT-7epo, a human erythropoietin-dependent leukemia cell line, was used for the determination of the erythropoietic potency of the peptides. UT-7epo cells (Deutsche Sammlung von Mikroorganismen und Zellkulturen (DSMZ), Cat. No. ACC 363) were grown in a complete RPMI-1640 medium with 10% FBS and 5 ng/ml erythropoietin. The proliferation/survival (=viability increase) response of the cells exposed to erythropoietin is mediated by the classical erythrocyte-type erythropoietin receptor and is a quantitative measure of the capacity of erythropoietin-variants to stimulate the classical erythropoietin receptor.

UT-7epo cells were transferred to fresh complete RPMI 1640 medium containing 10% donor calf serum, 4 mM L-glutamine, and supplemented with 5 ng/ml of recombinant human erythropoietin. The cells were maintained in 75 cm$^2$ flasks with 20 ml of medium/flask in a humidified incubator with 5% $CO_2$ at 37° C. for 48 h. On day two of the assay, i.e., at 48 h, the cells were transferred from the flask into a 50-ml conical tube and centrifuged at 1,000 rpm for 5 minutes at room temperature. The supernatant was discarded and the cells washed two times with 10 ml of starvation media (3% donor calf serum, 4 mM L-glutamine). The cells were then re-suspended in starvation media, using up and down pipette action to obtain a single cell suspension. The re-suspended cells were diluted with starvation media to a obtain a density of $4\times10^5$ cells/ml, and plated at a total culture volume of 10 ml per 25 cm$^2$ flask. Following a 4 h incubation, the cells were again transferred to a 50-ml conical tube. Control cells were maintained throughout with 5 ng/ml of rhu-erythropoietin.

Cells were diluted to 200,000 cells/ml in starvation medium, plated at 100 µl/well in a 96 well plate and exposed to varying concentrations of erythropoietin, carbamylated erythropoietin, and Peptide D, SEQ ID NO:30. A series of 10 fold dilutions in RPMI 1640 medium containing 3% serum was used to generate concentrations of test compounds from 0.2 pM to 20 nM. Following a further for 48 h incubation, a solution of 15 ml WST-1 Cell Proliferation Reagent (Roche) was added to each well, and incubated for 1 hour at 37° C. in $CO_2$. After mixing for 1 minute, the plate was read in a plate reader (absorption at 450 nm, subtracted from background absorption at 650 nm).

Figure 3:
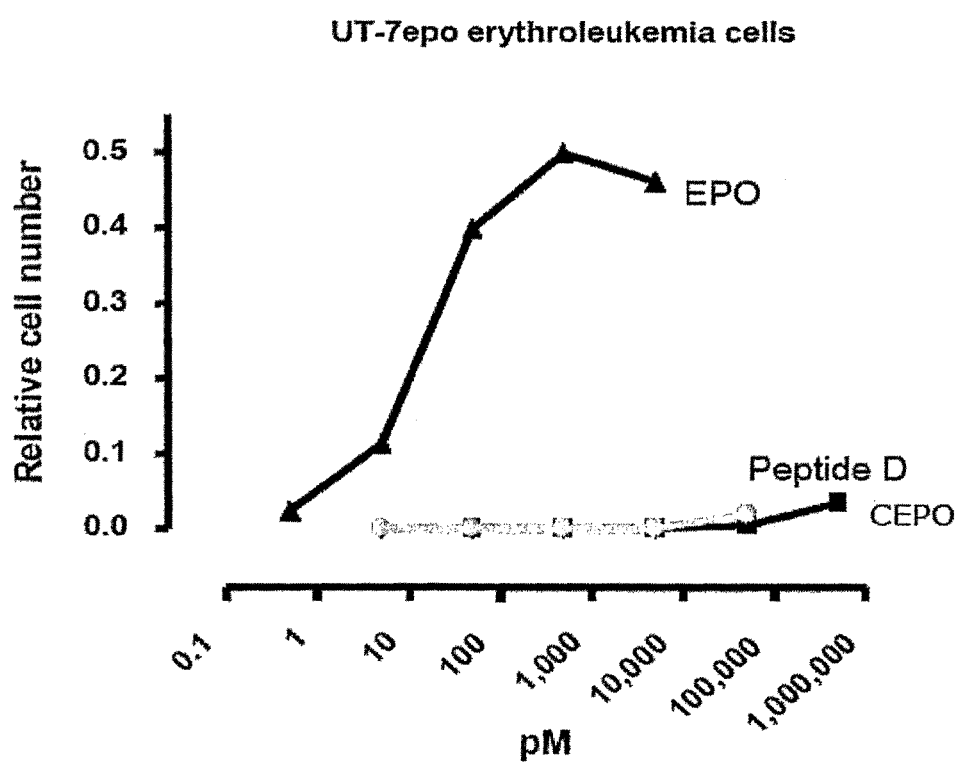

Peptide D exhibited no erythropoietic activity at doses as high as 10,000 pM (FIG. 3). Preferably, the peptide will have no erythropoietic activity for a dose lower than 1 µg/ml, and more preferably for a dose lower than 10 µg/ml.

B. In Vivo Assessment:

To evaluate the erythropoietic activity of tissue protective peptide F (SEQ ID NO:33) or peptide G (SEQ ID NO:40, as discussed supra a peptide constructed of the presenting residues of Helix B), the peptides were administered 0.8 µg/kg subcutaneously three time per week to male Sprague Dawley rats. The dosage schedule corresponded to the equivalent dose (on a molar basis) of EPO previously determined to be elicit maximum erythropoiesis. Hemoglobin concentration was determined periodically by use of an automated analyzer (Keska Corporation).

Figure 4:
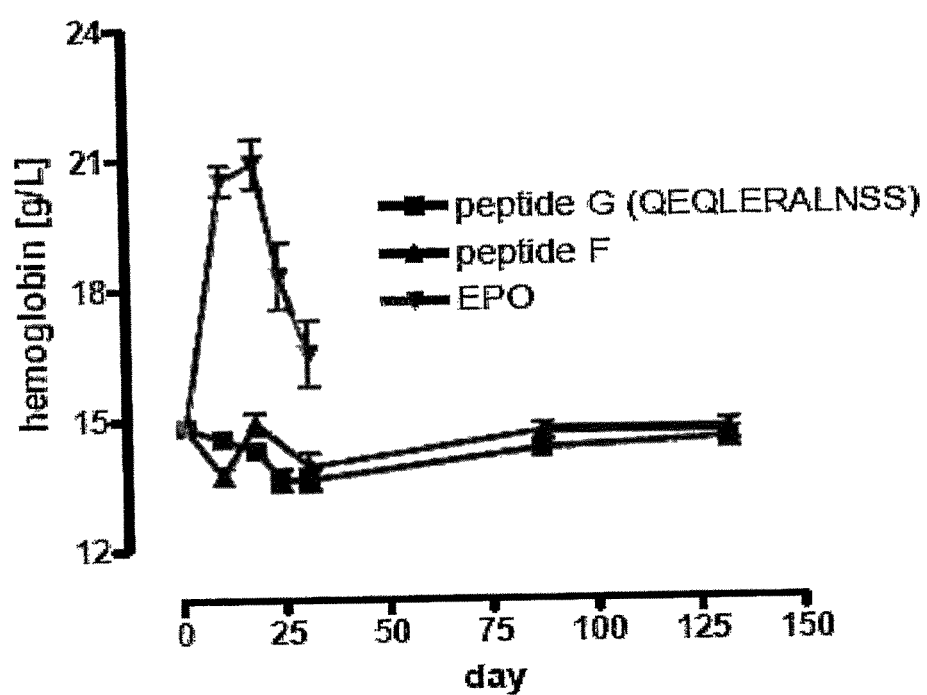

Neither Peptide B nor Peptide C showed any increase in hematocrit over the course of the study (FIG. 4; the response to an equimolar dosage of EPO is presented for comparison). The decrease in hemoglobin noted for EPO after 3 weeks is due to the production of anti-EPO neutralizing antibodies which cause pure red cell aplasia. In contrast, no neutralizing antibody response was observed for either peptide G or peptide F.

Example 4

Peptide is Tissue Protective in In Vitro Assays

Peptides can be readily assessed for tissue protection using any number of in vitro assays. For example, protection from excitoxicity can be determined using kainite-induced death of mouse motoneurons. Spinal cords were obtained from 15-day old Sprague—Dawley rat embryos as previously described (Siren et al., 2001, PNAS 98:4044, hereby incorporated by reference in its entirety). The ventral horn was trypsinized and centrifuged through a 4% BSA cushion for 10 min at 300×g. Cells (representing mixed neuron-glia culture) were seeded at a density of 2,000 cells/cm$^2$ into 24-mm well plates precoated with poly-DL ornithine and laminin. Motoneurons were further purified by immunopanning and the cells were seeded at low density (20,000 cells/cm$^2$) onto 24-mm well plates precoated with poly-DL-ornithine and laminin, and containing complete culture medium [Neurobasal/B27 (2%); 0.5 mM L-glutamine; 2% horse serum; 25 mM 2 mercaptoethanol; 25 mM glutamate; 1% penicillin and streptomycin; 1 ng/ml BDNF]. The medium (without glutamate) was re-added to cultures on days 4 and 6.

Cell death was induced on day 6 in culture by incubation for 48 h with kainic acid (5 mM for mixed neuron-glia cultures; 50 mM for purified cultures). Peptide D (5 ng/mL) or vehicle was added to the cultures 72 h before induction of cell death, and treatment continued for 48 h. The medium was then discarded and the cells fixed with 4% (vol/vol) paraformaldehyde in PBS for 40 min, permeabilized with 0.2% Triton X-100, blocked with 10% (vol/vol) FCS in PBS, incubated with antibodies against non-phosphorylated neurofilaments (SMI-32; 1:9,000) overnight, and visualized by using the avidin-biotin method with diaminobenzidine. Viability of motoneurons was assessed morphologically by counting SMI-32 positive cells across four sides of the cover slip and staining for apoptotic bodies was done by using H33258.

Figure 5:
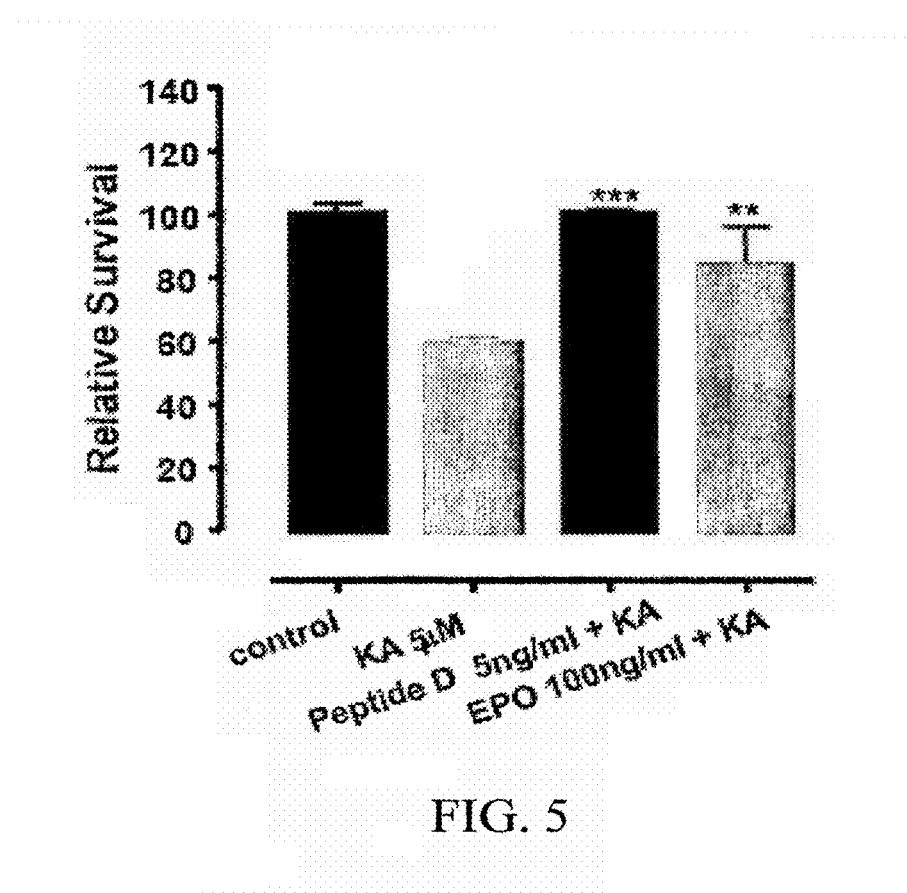
FIG. 5 depicts the results of in vitro studies that demonstrate that peptide D, SEQ ID NO:30, protects motor neurons against kainate induced death.

Peptide D (SEQ ID NO:30, corresponding to amino acids 58-82 of SEQ ID NO:1) completely protected motoneurons from injury caused by kainate (FIG. 5).

Alternatively, tissue protection afforded by peptides can be determined using an assay employing mouse P19 cells, which are neuronal-like and die via apoptosis upon withdrawal of serum. Tissue protection of peptide D (SEQ ID NO:30) was compared to that of EPO using P19 clone P19S1801A1 as previously published (Siren et al., 2001, *PNAS* 98:4044, hereby incorporated by reference in its entirety). Cells were maintained undifferentiated in DMEM supplemented with 2 mM Lglutamine; 100 units/ml penicillin G; 100 mg/ml streptomycin sulfate (GIBCO); 10% (vol/vol) FBS (HyClone), containing 1.2 g/liter $NaHCO_3$ and 10 mM Hepes buffer, hereafter referred to as complete medium. Serum-free medium contained the same components as above with the deletion of serum and the addition of 5 mg/ml of insulin; 100 mg/ml of transferrin; 20 nM progesterone; 100 mM putrescine; 30 nM $Na_2SeO_3$ (from Sigma). For the experiments, 50% confluent cells were pretreated overnight with EPO or vehicle, dissociated with trypsin, washed in serum-free medium, and plated in 25-cm$^2$ tissue culture flasks at a final density of 104 cells/cm$^2$ in serum-free medium alone or with added EPO. Cell viability and was determined by trypan blue exclusion and a hemacytometer.

Figure 6:
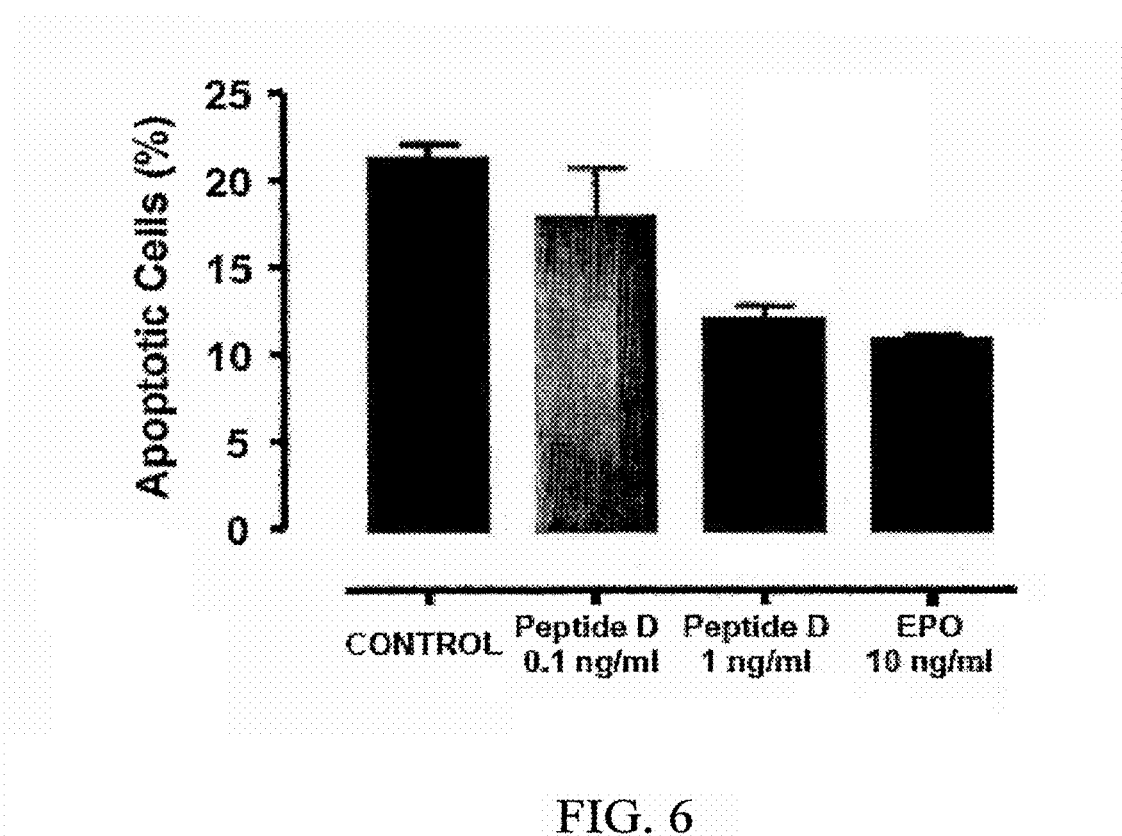
FIG. 6 shows that peptide D, SEQ ID NO:30, at doses of 0.1 ng/ml and 1 ng/ml protects P-19 cells against apoptosis associated with serum deprivation.

Peptide C, SEQ ID NO:29 (corresponding to amino acids 38-57 of SEQ ID NO:1) was at least 10 time more potent on a weight basis than EPO in preventing apoptosis of p19 cells (FIG. 6).

Example 5

Middle Cerebral Artery Occlusion Model

Male Crl:CD(SD)BR rats weighing 250-280 g were obtained from Charles River, Calco, Italy. Surgery was performed in accordance with the teachings of Brines et al., 2000, PNAS USA 97:10526-10531 (hereby incorporated by reference in its entirety. Briefly, the rats were anesthetized with chloral hydrate (400 mg/kg-bw, i.p.), the carotid arteries were visualized, and the right carotid was occluded by two sutures and severed. A burr hole adjacent and rostral to the right orbit allowed visualization of the middle cerebral artery ("MCA"), which was cauterized distal to the rhinal artery. To produce a penumbra (border zone) surrounding this fixed MCA lesion, the contralateral carotid artery was occluded for 1 hour by using traction provided by a fine forceps and then re-opened.

Sprague Dawley rats (8 per group) were subjected to the above noted MCAO protocol. The rats were administered PBS, carbamylated erythropoietin (44 ug/kg), or peptide D (aa 58-82; 4.4 ug/kg) upon release of the occlusion. Additionally, peptide D (aa 58-82; 4.4 ug/kg) was administered in four doses at 2 hour intervals following the occlusion to a separate group. For assessment of injury, rats were subjected to behavioral testing or the volume of the lesion was determined by tetrazolium staining of brain sections performed 24 hours post surgery in accordance with the previously noted protocol.

FIG. 7A presents a graph demonstrating the volume of lesions resulting from the MCAO protocol. Treatment with peptide D (SEQ ID NO:30), either as a single dose or by multiple doses, reduced the lesion volume resulting from the MCAO surgery by about two thirds: statistically equivalent to the tissue protective effects of carbamylated erythropoietin.

(b) Therapeutic Window of Tissue Protective Cytokines

The MCAO protocol as outlined above was repeated for the instant example. Following the occlusion procedure, PBS, carbamylated erythropoietin (44 ug/kg, i.v.), or peptide D (SEQ ID NO:30) (4.4 ug/kg) were administered to the rats immediately after recirculation was established in the carotid (i.e., one hour from the onset of ischemia). In addition, peptide D (SEQ ID NO:30) was administered in four doses (each 4.4 ug/kg-bw) at 2 hours intervals following the occlusion. (8 rats per group).

(c) Behavioral Testing

A separate group of rats was also tested in a foot fault behavioral protocol. Rats were tested on an elevated stainless steel grid floor 30 cm×30 cm with grid size of 30 mm according to the protocol of Markgraf et al., 1992, Brain Research 575:238-246 (hereby incorporated by reference in its entirety). When placed on the grid, rat would attempt to move around and occasionally place a foot, rather than on the grid, through a grid opening ("foot fault"). The number of foot faults was measured for a 1 minute period.

The rats treated with peptide D (SEQ ID NO:30) following reperfusion suffered from fewer foot faults than those treated with PBS (FIG. 7B). No significant additional benefit was observed following the administration of multiple doses of peptide D (SEQ ID NO:30). Although the mean number of foot faults was less in the group receiving multiple doses of peptide, the difference observed was not significantly different from the group receiving a single dose.

Example 6

Diabetic Neuropathy

Diabetes was induced in male Sprague Dawley rats (Charles River, Calco, IT) using streptozocin administered at a single dose of 60 mg/kg ip in fasting rats as previously described (Bianchi et al., 2004, Proc Natl Acad Sci USA 101, 823-828, hereby incorporated by reference in its entirety). Diabetes was confirmed by increased serum glucose levels to greater than 300 mg per deciliter (mg %) (normal levels are <100 mg %). Diabetic animals were then treated with peptide D (SEQ ID NO:30; 4 μg/kg) or vehicle 5 times a week intraperitoneally. Two weeks after induction of the diabetic state, nerve conduction velocity was determined using the caudal nerve.

As shown in FIG. 8A, the diabetic animals exhibited a reduction in caudal nerve conduction velocity from about 22 m/s (normal) to about 19 m/s. Administration of peptide D (SEQ ID NO:30) was associated with an increase in conduction velocity to about 23 m/s.

Additionally, the thermal nociceptive threshhold was quantified by measurement of the time to paw withdrawal in a "hot plate" test. Withdrawal latency was defined as the time between placement on the hot plate and the time of withdrawal and licking of hind paw. Each animal was tested twice separated by a 30 min rest interval. Hind paw thermal threshhold was measured 4 weeks after induction of diabetes. Peptide D (SEQ ID NO:30) reduced the latency time spent on the hot plate by the diabetic animal (FIG. 8B).

Example 7

Protection of Sciatic Nerve and Kidney from Cisplatinum-Induced Injury

Cisplatinum (CDDT) was administered intraperitoneally to male Sprague-Dawley rats at 2 mg/kg twice weekly for 5 weeks as described in Bianchi et al., 2006, Clin Cancer Res 12: 2607-2612, hereby incorporated by reference in its entirety. Animals were separated into groups of 6 each. During the 5 week CDDT administration, animals also received either peptide G, (SEQ ID NO:40) at 0.4 μg/kg-bw or PBS i.p. three times per week. A control group received PBS instead of CDDT. Hot plate latency was determined as described in Example 6 above.

Animals that received CDDT and only PBS exhibited an increase in latency compared to controls: i.e., CDDT was associated with impaired thermal sensitivity. In contrast, animals that received the peptide exhibited normal hot plate latency (FIG. 9A).

Treatment with peptide also prevented CDDT-induced polyuria (FIG. 9B) Specifically, animals that had received PBS exhibited a significant increase in daily urine production from about 30 mL/day to about 47 mL/day. In contrast, animals having received the tissue-protective peptide did not significantly differ from controls animals that received PBS instead of CDDT.

Example 8

Protection from Diabetes-Induced Retinal Vascular Leak

Beneficial effects of tissue-protective peptides on hyperglycemia-induced retinal vascular leakiness can be determined using a rat model of diabetic retinopathy. In this model, Evans blue is used to determine leakage from the blood vessel into tissues as described by Xu et al., 2001, Invest. Ophthal. Vis. Sci 42: 789-794 (hereby incorporated by reference in its entirety). Evans blue is tightly bound to albumin and is therefore retained within the circulation unless leakiness of the vessel wall occurs, such as caused by uncontrolled diabetes mellitus.

In this model, fasting male Sprague-Dawley rats receive a single dose of streptozotocin (60 mg.kg ip). Two days later, following verification of the development of diabetes mellitus (fasting serum glucose greater than 300 mg %, animals were divided into groups of 6 animals each as well as a control group that did not receive streptozotocin. The two diabetic groups were administered either peptide D (SEQ ID NO:30) at 4 µg.kg intraperitoneally 5 days a week or PBS on the same schedule. After three weeks of uncontrolled diabetes, animals were anesthetized and administered Evans Blue dye (30 mg/kg) intravenously, which was allowed to circulate for 2 hours. Using transcardiac puncture, the animals were then perfused with PBS until the effluent was clear followed by 4% paraformaldehyde. The eyes were then removed and the retinas carefully dissected from the globe. The retinal content of Evans Blue was determined by incubating the retinas in formamide at 80° C. for 18 hours. The supernatant was then removed and saved for analysis and the retinas completely dried and weighed. Concentration of Evans Blue in the supernatant was determined by a spectrophotometer and a standard curve of Evans Blue dissolved in formamide established.

As seen in FIG. 10, animals that received administration of peptide D (SEQ ID NO:30) experienced no increase in Evans Blue dye within the retina, compared to control. In contrast, diabetic animals that received only PBS exhibited an increase in retinal Evans blue content, indicating the vascular leakage had occurred.

Example 9

Protection from Acute Renal Failure

Tissue-protective peptides are also effective in preventing injury to the kidneys in the setting of ischemia. Adult male Wistar rats were anesthetized and an abdominal incision made to visualize both renal arteries. Using an atraumatic vascular clamp, both arteries were compressed for 60 minutes, completely arresting renal blood flow. The clamps were then removed to restore circulation and peptide F (SEQ ID NO:33) or peptide G (SEQ ID NO:40) was administered at 290 pmol/kg-bw intravenously. An additional group undergoing ischemia received only PBS intravenously.

Seventy two hours following reperfusion, the animals were anesthetized and underwent perfusion-fixation using paraformaldehyde. Fixed animals were sectioned sagittally into halves and further fixed by immersion in 10% formaldehyde at room temperature for one day. Histological evaluation of the kidneys was performed according to the protocol of Sharples et al., 2005, J Amer Soc Nephrol: 15: 2115 (hereby incorporated by reference in its entirety). Briefly, after dehydration using graded ethanol, pieces of kidney were embedded in parafin, cut into 5 micrometer sections and mounted on glass slides. Sections on slides were deparaffinized with xylene, counterstained with hematoxylin and eosin, and examined under a light microscope. One hundred fields were examined for each kidney, and a score from 0 to 3 was given for each tubular profile: 0, normal histology; 1, tubular cell swelling, brush border loss, and nuclear condensation with up to one third nuclear loss; 2, as for score 1 but greater than one third and less than two thirds tubular profiles showing nuclear loss; and 3, greater than two thirds tubular profile showing nuclear loss. The histologic score for each kidney was calculated by addition of all scores, with a maximum score of 300.

Administration of either peptide F (SEQ ID NO:33) or peptide G (SEQ ID NO:40) was associated with a significant reduction in injury score (p<0.05) compared to the controls.

Example 11

Efficacy of Tissue Protective Peptides in Cerebral Malaria

A rodent model of cerebral malaria was developed according to Kaiser et al., 2006, J. Infect. Dis. 193:987-995 (hereby incorporated by reference in its entirety. Female CBA/J mice 7 weeks old were separated into groups of 20 animals. Each group was infected with *Plasmodium berghei* Anka (PbA) administered intraperitoneally as a dose of $10^6$ PbA infected erythrocytes. Mice received either PBS or peptide F (SEQ ID NO:33) on days 4, 5, and 6 as intraperitoneal injection at a dose of 2.6 µg/kg. Clinical status and blood smear data were gathered during the follow-up (end point D30). Cumulative long-term survival was calculated according to the Kaplan-Meier method and groups were compared with the log rank test. Survival time was the dependant variable. A p-value of <0.05 was considered significant.

As shown in FIG. 12, all mice in the control group (saline) died by day 8. In contrast, mice that received peptide F (SEQ ID NO:33) exhibited prolonged survival, significantly different from the control group (p<0.005), using a log-rank test.

Example 12

Efficacy of Tissue Protective Peptides in a Murine EAE Model

Experimental autoimmune encephalomyelitis ("AEA") was induced in C57BL/6 female mice (6-8 weeks of age) according to Savino et al., 2006, J Neuroimmunol 172:27-37, hereby incorporated by reference in its entirety. EAE was induced by subcutaneous immunization in the flanks with a total of 200 µg of MOG35-55 (Multiple Peptide Systems, San Diego, Calif., USA) in incomplete Freund's adjuvant (Sigma, St Louis, Mo., USA) supplemented with 8 mg/ml of *Mycobacterium tuberculosis* (strain H37RA; Difco, Detroit, Mich., USA). Animals were housed in specific pathogen-free conditions, allowing access to food and water ad libitum. Mice received 500 ng of pertussin toxin (Sigma) i.v. at the time of immunization and 48 h later. Weight and clinical score were recorded daily (0=healthy, 1=flaccid tail, 2=ataxia, and/or hind-limbs paresis, or slow righting reflex, 28 C. 3=paralysis of hind limb and/or paresis of forelimbs, 4=paraparesis of fore limb, 5=moribund or death). Food pellets and the drinking water were placed on Petri plates on the floor of the cage to enable sick mice to eat and drink. Peptide E (SEQ ID NO:31) was administered daily subcutaneously at a dose of 4.4 micrograms/kg-bw, starting on day 4 after immunization.

Administration of peptide E (SEQ ID NO:31) significantly reduced both the time course and severity of the clinical presentation of AEA in the treated animals (p<0.01) (FIG. 13).

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed is:

1. An isolated polypeptide consisting of the amino acid sequence WEHVNAIQEARRLL (SEQ ID NO: 35).

2. The isolated polypeptide of claim 1, wherein the polypeptide is further conjugated to polyethylene glycol.

3. A pharmaceutical composition comprising the isolated polypeptide of claim 1 and a pharmaceutically acceptable carrier.

4. The pharmaceutical composition of claim 3, wherein said composition is formulated for oral, intranasal, ocular, inhalational, transdermal, rectal, sublingual, or parenteral administration.

5. The pharmaceutical composition of claim 3, wherein said composition is formulated as a perfusate solution.

6. A method for maintaining, or enhancing the viability of a responsive cell, tissue, or organ isolated from a mammalian body comprising exposing said cell, tissue, or organ to the isolated polypeptide according to claim 1 or the pharmaceutical composition according to claim 3.

7. The method of claim 6, wherein the mammalian body is a human body.

8. A method for the treatment in a subject in need thereof of a cardiovascular disease, cardiopulmonary disease, respiratory disease, kidney disease, disease of the urinary system, disease of the reproductive system, bone disease, skin disease, gastrointestinal disease, endocrine abnormality, metabolic abnormality, cognitive dysfunction, or a disease or disorder of the central or peripheral nervous system, said method comprising administering to the subject the isolated polypeptide according to claim 1 or the pharmaceutical composition according to claim 3.

9. The method of claim 8, wherein the subject is a human.

10. An isolated nucleic acid comprising a polynucleotide sequence encoding the isolated polypeptide of claim 1.

11. A vector comprising the nucleic acid of claim 10.

12. The vector of claim 11 that is an expression vector.

13. A host cell containing the expression vector of claim 12.

14. A method of recombinantly producing the isolated polypeptide comprising: (a) culturing in a medium the host cell of claim 13, under conditions suitable for the expression of said polypeptide, and (b) recovering and isolating the polypeptide from said medium.

\* \* \* \* \*